United States Patent [19]
Tsuji et al.

[11] Patent Number: 5,502,799
[45] Date of Patent: Mar. 26, 1996

[54] RENDERING APPARATUS, MULTISPECTRAL IMAGE SCANNER, AND THREE-DIMENSIONAL AUTOMATIC GONIO-SPECTROPHOTOMETER

[75] Inventors: Hiroyoshi Tsuji; Kazuhiko Suzuki; Keiko Watanabe; Atsushi Takagi; Hitoshi Takaoka, all of Aichi; Goro Baba, Saitama, all of Japan

[73] Assignees: Kabushiki Kaisha Toyoto Chuo Kenkyusho, Aichi; Toyoto Jidosha Kabushiki Kaisha, Toyota, both of Japan

[21] Appl. No.: 61,093

[22] Filed: May 14, 1993

[30] Foreign Application Priority Data

May 15, 1992 [JP] Japan ................................. 4-123603
May 15, 1992 [JP] Japan ................................. 4-123604
May 15, 1992 [JP] Japan ................................. 4-123961

[51] Int. Cl.$^6$ ................................................. G06F 15/00
[52] U.S. Cl. ........................................................ 395/131
[58] Field of Search ................................. 395/118, 140, 395/131, 155, 161, 129, 130, 132; 356/319; 345/12, 13, 114, 117

[56] References Cited

PUBLICATIONS

Computer Graphics, vol. 24, No. 4, Aug. 1990, pp. 263–272, A. Takagi, et al., "Accurate Rendering Technique Based on Colorimetric Conception".

Applied Optics, vol. 16, No. 12, Dec. 1977, S. K. Park, et al., "Estimation of Spectral Reflectance Curves From Multispectral Image Data".

Journal of Optical Society of America A, vol. 3, No. 10, 1986, pp. 1673–1683, L. T. Maloney, "Evaluation of Linear Models of Surface Spectral Reflectance with Small Numbers of Parameters".

Journal of the Color Science Association of Japan, vol. 14, No. 1, 1990, pp. 77–78, M. Nakayama, et al., "Estimation of Spectral Reflectances for Color Scanners".

Communication of the ACM, vol. 19, No. 10, 1976, pp. 542–547, J. F. Blinn, et al., "Texture and Reflection in Computer Generated Images".

*Primary Examiner*—Phu K. Nguyen
*Attorney, Agent, or Firm*—Oblon, Spivak, McClelland, Maier & Neustadt

[57] ABSTRACT

A rendering apparatus includes: a radiant-energy calculating device for determining a spectral radiance for each infinitesimal area of an object by using a spectral radiance of a light source irradiating the object, a spectral reflectance in the infinitesimal area of the object, and a spectral reflectance factor in a wide area of the object; a color-specification-value calculating device for calculating color specification values of a colorimetric system on the basis of the spectral radiance obtained for each infinitesimal area; a transforming device for transforming the color specification values into image data for displaying an image of the object; and a display device for displaying the image of the object on the basis of the image data.

14 Claims, 34 Drawing Sheets

CALCULATION OF SAMPLE

RENDERING APPARATUS, MULTISPECTRAL IMAGE SCANNER, AND THREE-DIMENSIONAL AUTOMATIC GONIO-SPECTROPHOTOMETER

BACKGROUND OF THE INVENTION

1. Field of the Invention

The present invention relates to a rendering apparatus, a multispectral image scanner, and a three-dimensional automatic gonio-spectrophotometer. More particularly, the present invention concerns a rendering apparatus for reproducing and displaying an object three-dimensionally and realistically through image processing technique such as computer graphics, a multispectral image scanner usable in the rendering apparatus to measure a spectral reflectance distribution using optical filters, and a three-dimensional automatic gonio-spectrophotometer usable in the rendering apparatus to automatically conduct three-dimensional spectrocolorimetry of an object having complicated reflection characteristics such as fabrics.

2. Description of the Related Art

Conventionally, a method is known in which, with respect to an object in which the optical properties of the surface are uniform, the color of the object is reproduced and displayed three-dimensionally and realistically by calculating coloring on the basis of a ray tracing method by using the two-dimensional spectral reflectance factor of the object surface (A. Takagi et al., Computer Graphics, Vol. 24, No. 4, 1990).

In this method, as shown in Formula (1) shown below, color specification values (tristimulus values) of the CIE (International Commission on Illumination) standard XYZ colorimetric system are first determined on the basis of a spectral reflectance factor and the like of the object surface. These tristimulus values are then transformed into color specification values peculiar to the colorimetric system through a linear combination transform shown in Formula (2) below, are subjected to γ correction, and are transformed into RGB gradients, thereby displaying a reproduced image of the object.

$$\begin{pmatrix} X \\ Y \\ Z \end{pmatrix} = \frac{1}{k} \int_\lambda \int_\Omega R(\lambda, \Phi) \cdot L(\lambda, \Theta) \cdot \cos\theta \begin{pmatrix} \bar{x}(\lambda) \\ \bar{y}(\lambda) \\ \bar{z}(\lambda) \end{pmatrix} d\omega d\lambda \quad (1)$$

Where, $R(\lambda, \Phi)$: spectral reflectance factor of an object $L(\lambda, \Theta)$: spectral radiance of an incident light source $\bar{x}(\lambda), \bar{y}(\lambda), \bar{z}(\lambda)$: CIE color matching functions $\Phi$: angular condition determined by an incident angle, a reflection angle, and an azimuth angle (e.g., an incident azimuth angle and a reflection azimuth angle)

$\Theta$: angular condition determined by an incident angle and an azimuth angle (e.g., an incident azimuth angle)

$\theta$: incident angle $\omega$: very small solid angle as viewed from the infinitesimal area of the object surface $\Omega$: total solid angle as viewed from the infinitesimal area of the object surface $\lambda$: wavelength $k$: normalization coefficient $$\begin{pmatrix} Y_R \\ Y_G \\ Y_B \end{pmatrix} = A^{-1} \begin{pmatrix} X \\ Y \\ Z \end{pmatrix} \quad A = \begin{pmatrix} a_{11} & a_{12} & a_{13} \\ a_{21} & a_{22} & a_{23} \\ a_{31} & a_{32} & a_{33} \end{pmatrix} \quad (2)$$

Where, $Y_R, Y_G, Y_B$: luminance values of the RGB colorimetric system $A$: color-matching transformation matrix consisting of $a_{ij}$ (i, j=1, 2, 3)

$a_{ij}$: coefficient of a display unit (determined by measurement of the luminance of the display screen)

According to this method, it is possible to obtain the spectral radiance per very small solid angle at a time when a spectral radiance $L(\lambda, \Theta)$, which is made incident upon the infinitesimal area of the object surface at an angle θ, is reflected by the object surface having a spectral reflectance factor $R(\lambda, \Phi)$, and is directed toward an image display position (i.e., a visual point). By integrating this spectral radiance per very small solid angle with respect to the solid angle, it is possible to obtain the total spectral radiance made incident upon the visual point from the infinitesimal area. Then this total spectral radiance is transformed into tristimulus values of the XYZ colorimetric system.

With the above-described method, however, since the spectral reflectance factor of an infinitesimal area is used, the method is applicable to an object in which the spectral reflectance distribution of the surface is uniform, but it is not applicable to an object in which the spectral reflectance distribution of the surface is nonuniform, such as an object having a fine colored pattern and texture. In addition, since the spectral reflectance differs for the object having complicated reflection characteristics, such as fabrics, depending on angular conditions for measuring the object, this method is not applicable to such an object.

In addition, to apply the above-described method to an object in which the spectral reflectance distribution of the surface is nonuniform, the spectral reflectance factor of the infinitesimal area of the object is required over the entire surface. However, since no apparatus for measuring the spectral reflectance factor for the entire surface has been available, it is impossible to obtain a desired amount of measured values. Moreover, even if such measured values were available, since it is necessary to retain the measured values for the entire object surface in accordance with the wavelengths with respect to combinations of three-dimensional angular conditions, the amount of data held becomes enormously large. Thus it is difficult to configure a practicable system.

As a method of displaying a fine colored pattern and texture on an object, a texture mapping method is known (J. F. Blinn et al., Communication of the ACM, Vol. 19, No. 10, 1976). This method enables displaying a fine pattern and texture by mapping the plane pattern onto the object surface.

As for this method, however, mapping is generally effected by using as pattern data those color specification values of the RGB colorimetric system which are measured on the basis of a three-component separation method using a color scanner or the like. Although this method is effective in displaying a colored pattern and texture on the object surface, it is impossible to display an accurately color-matched and reproduced image of the object surface. In other words, since the color specification values for mapping are values which are measured under a certain light source and are determined uniformly, the color specification values cannot be changed in accordance with a change in the spectral distribution of incident light, e.g., a change of the light source. In addition, since the RGB colorimetric system is a colorimetric system peculiar to a measuring system, transformation to another colorimetric system is complicated, and the accuracy at the time of transformation becomes low. Furthermore, since the angular conditions for measuring the color specification values are dependent on the measuring system of a measuring apparatus such as a color scanner and are therefore determined uniformly, it is impossible to obtain color specification values at arbitrary angular conditions.

In addition, in the measurement of the aforementioned spectral reflectance distribution, a method has been proposed in which an apparatus for detecting reflected light by using a scanner is provided, and the spectral reflectance in infinitesimal areas is estimated from a color-separation output system for image plane pixels by using this scanner (Mitsugu Nakayama, et al., "Estimation of spectral reflectances for color scanners", Journal of the Color Science Association of Japan, Vol. 14, No. 1, 1990).

In this method, the spectral reflectance is estimated on the basis of outputs for respective channels (hereafter referred to as channel outputs) of a scanner using interference filters for predetermined wavelength bands (hereafter referred to as channels), i.e., a limited number of narrow-bands. According to this method, overall characteristics including all the characteristics of a scanner optical system such as those of a light source, optical filters, a light-detecting element, and the like are determined by using a plurality of samples whose spectral reflectances are already known. By applying these characteristics to measured values of a sample whose reflectance is unknown, the spectral reflectance can be estimated.

In addition, as similar methods, a method proposed by Stephen K. Park et al. for determining the overall characteristics (Applied Optics, Vol. 16, No. 12, 1977) and a method proposed by Maloney (Journal of the Optical Society of America A Vol. 3, No. 10, 1986) are also known. In the method proposed by Stephen K. Park et al., the spectral reflectance is estimated by applying the Shannon's data-sampling theorem to channel outputs which are not necessarily narrow-bands. Meanwhile, in the method proposed by Maloney, it is assumed that the spectral reflectance can be expressed by the weighted linear sum of channel outputs, and the spectral reflectance is estimated by the method of least squares.

In each of the above-described methods, however, since the bandwidths of the filters used are relatively wide, the spectral reflectance is estimated from a small number of channel outputs on condition that the spectral distribution of the light source and the spectral sensitivity of the light-receiving element in the scanner optical system are smooth. In these methods, there are problems in that numerous measurements and complicated calculations are required, and that when optical conditions have changed, resetting must be carried out in a similar procedure.

In a scanner which uses a CCD line sensor as the light-detecting element, a fluorescent lamp is frequently used as a line light source. However, since a bright line spectrum corresponding to the component of a sealed gas is produced from this fluorescent lamp, the spectral distribution is not smooth. Hence, errors occur in those methods with a premise that the spectral characteristics are smooth, as described above.

Furthermore, although the measurement of colors of light, paint and the like is conventionally carried out for the quality control of paints and the like, there has been no apparatus for properly conducting the colorimetry of the surface of a sample with a complicated shape in which the quantity of light and the degree of color change depending on the light-detecting direction, such as a fiber or metallic coating, i.e., for conducting the three-dimensional measurement of the spectral reflectance factor of an object.

Meanwhile, as apparatuses which are capable of conducting the colorimetry of such an object, photometers including a colorimeter for measuring the color of an object and a color meter are known. Among these photometers, a photometer, such as a two- or three-dimensional automatic gonio-spectrophotometer, is known for determining the reflectance not merely by uniformly conducting colorimetry at a position for measuring a sample, but by changing angles such as the incident angle and the light-detecting angle, i.e., the angle of direction of light to be detected with respect to the sample.

In this two-dimensional automatic gonio-spectrophotometer, as shown in FIG. 35A, the changing of the incident angle $\theta$ from the light source and the light-detecting angle $\phi$ to the light-detecting element, which are determined by angles formed with respect to the normal line of the surface of a sample F, is controlled by a personal computer having a central processing unit (CPU) so as to measure the spectral reflectance factor of the sample.

However, in the angle change control of such a two-dimensional automatic gonio-spectrophotometer, since the measurement is performed by fixing a detector unit (not shown) and by changing the incident angle $\theta$ and the light-detecting angle $\phi$ by rotating a light source unit 600 and a sample base 604, it is impossible to determine the spectral reflectance factor three-dimensionally.

In contrast, as shown in FIG. 35B, in a three-dimensional automatic gonio-photometer, which is provided with a three-dimensional angle-changing mechanism for manually rotating the sample F, the light source unit (not shown) is fixed, and the luminous intensity is measured three-dimensionally by changing the angles by rotating the sample F, a detecting unit 602, and the sample base 604.

However, with this three-dimensional automatic gonio-photometer, since only the reflection intensity of the sample F is determined, it is impossible to conduct spectrophotometric colorimetry through the measurement of the spectral reflectance. To conduct this spectrophotometric colorimetry, it is sufficient to dispose a spectroscope or the like. Yet, since a movable section of the three-dimensional automatic gonio-photometer is located in the detecting unit 602 for measuring the quantity of light, it is difficult to dispose a large-size optical instrument such as the spectroscope in this movable section.

Accordingly, the three-dimensional spectral reflectance factor of the sample F has been determined by estimating on the basis of measured data obtained by a two-dimensional automatic gonio-spectrophotometer and measured data obtained by a three-dimensional automatic gonio-photometer.

However, in determining the three-dimensional measured data of the spectral reflectance factor from the aforementioned measured data obtained by the two-dimensional automatic gonio-spectrophotometer and measured data obtained by the three-dimensional automatic gonio-photometer, there have been problems in that much time and labor are required, and that error is unavoidable since the resultant data are based on the estimation.

In addition, the spectral reflectance factor $R(\lambda)$ is determined from a ratio between a spectral radiant flux with a wavelength $\lambda$ reflected from an object and a spectral radiant flux with the wavelength $\lambda$ reflected from a perfect reflecting diffuser (JIS-Z8105, Z8722). To determine the spectral reflectance factor in a shorter period of time, a double beam method is known in which, by using a reference white plate S such as a glass plate coated with barium sulfate, the spectral reflectance factor is determined on the basis of measured values of reflected light from the reference white plate S and reflected light from the sample F. In this double beam method, light emitting from the same light source can be radiated to both the reference white plate S and the sample F under the same conditions, i.e., with an identical incident angle and an identical light-detecting angle, and the spectral reflectance factor can be determined on the basis of the following Formula (a):

$$R(\lambda) = R_w(\lambda) \cdot r(\lambda)/r_w(\lambda) \quad (a)$$

Where, $R(\lambda)$: spectral reflectance factor of the sample F $R_w(\lambda)$: spectral reflectance factor of a working standard white plate C $r(\lambda)$: relative spectral reflectance factor of the sample F relative to the reference white plate S $r_w(\lambda)$: relative spectral reflectance factor of the working standard white plate C relative to the reference white plate S However, a phenomenon (sheen) is known in which, if the reference white plate S is used, even though a surface may be uniformly diffusive in an area with a small incident angle, a peak of strong reflected light appears in the direction of regular reflection (in which the incident angle $\theta$ and the light-detecting angle $\phi$ are substantially identical) when the incident angle becomes large. In this area of sheen, uniform diffusion becomes nonuniform, so that a method for accurately determining the spectral reflectance factor in such an area of sheen has not been established.

SUMMARY OF THE INVENTION

Accordingly, it is a primary object of the present invention to provide a rendering apparatus capable of reproducing the color of an object surface as a color which matches the visual sense irrespective of the configuration of the object and the condition of its surface, thereby overcoming the above-described drawbacks.

A second object of the present invention is to provide a multispectral image scanner capable of being used in a rendering apparatus and of determining the spectral reflectance with simple calculation processing irrespective of the spectral characteristics of an optical system.

A third object of the present invention is to provide a three-dimensional automatic gonio-spectrophotometer capable of being used in a rendering apparatus and of speedily and automatically conducting three-dimensional spectrocolorimetry of an object to be measured despite an effect of sheen.

To attain the above-described objects, in accordance with a first aspect of the invention, there is provided a rendering apparatus comprising: radiant-energy calculating means for determining a spectral radiance for each infinitesimal area of an object by using a spectral radiance of a light source irradiating the object, a spectral reflectance in the infinitesimal area of the object, and a spectral reflectance factor in a wide area of the object; color-specification-value calculating means for calculating color specification values of a colorimetric system on the basis of the spectral radiance obtained for each infinitesimal area; transforming means for transforming the color specification values into image data for displaying an image of the object; and display means for displaying the image of the object on the basis of the image data.

When an object is viewed by the eye, the light reaching the position of a visual point from the object surface is related to the spectral radiance of the light source irradiating the object and the surface reflectance distribution of the object surface. Namely, the light emitted from the light source reaches the position of the visual point as the light having a color affected as a result that the light reaches the object surface and is diffused by or transmitted through the object surface. Accordingly, to display an image of the object in such a manner as to allow the image to agree with the viewing condition, it suffices if the image data are formed by taking into account the spectral radiance of the light source irradiating the object and the surface reflectance distribution of the object surface.

Accordingly, the rendering apparatus in accordance with the present invention is provided with the radiant-energy calculating means for determining a spectral radiance for each infinitesimal area of an object by using a spectral radiance of a light source irradiating the object, a spectral reflectance in the infinitesimal area of the object, and a spectral reflectance factor in a wide area of the object. As this spectral reflectance factor distribution, it suffices if values of a wide area of the object are used, and it is unnecessary to use a large volume of values. The color-specification-value calculating means calculates color specification values of a colorimetric system on the basis of the spectral radiance energy distribution thus obtained. The color specification values are transformed into image data for displaying an image of the object by the transforming means. The display means displays the image of the object on the basis of this image data.

Thus, by synthesizing the relationship between the wavelength dependence of an infinitesimal area of the object and the angular dependence of a wide area, it is possible to determine the spectral radiance of the infinitesimal area for reproducing the brightness which is angle dependent and the color which is wavelength dependent. By displaying the image on the basis of spectral radiances determined for all the infinitesimal areas of the object surface, it is possible to display an image of the object with a colored pattern and texture which are faithful to the actual object surface without using a large amount of data.

As described above, in accordance with the first aspect of the present invention, the color of the infinitesimal area can be changed on the basis of the characteristics of the light radiated to the object surface and the reflectance characteristic (distribution) of the object surface, and the image whose brightness changes in accordance with the three-dimensional angular condition can be formed on the screen on the basis of the three-dimensional spectral reflectance factors of the object. Accordingly, there is an advantage in that the image of the object which matches the viewing condition can be reproduced and displayed.

In addition, since only a small amount of data on the reflectances is required as the data, there are advantages in that there is no need to store a large amount of data or to spend a long period of time in reading it, and that the apparatus for reproducing and displaying an image of the object can be constructed easily.

To attain the above-described objects, in accordance with a second aspect of the present invention, there is provided a multispectral image scanner comprising: optical means including an incident light source, light-detecting means for detecting a quantity of the light reflected from the object caused by the light radiated from the incident light source, and a plurality of optical filters for allowing the light in predetermined wavelength bands which do not overlap to be transmitted therethrough and for shielding the light other than that in the wavelength bands, so as to measure the amount of the reflected light by measuring the light transmitted through the optical filter; correcting means for determining for each predetermined wavelength band a central wavelength corrected on the basis of a spectral distribution obtained through a combination of at least a spectral distribution of the incident light source, a spectral transmittance of each of the optical filters, and the sensitivity of the light-detecting means; calibrating means for calibrating a measurement value of a sample for each central wavelength of each of the predetermined wavelength bands in such a manner that the measurement value becomes the spectral reflectance of a reference plate; and estimating means for estimating a spectral reflectance on the basis of the value calibrated for each central wavelength.

For each central wavelength of each of the predetermined wavelength bands, the calibrating means of the multispectral image scanner is capable of determining the correction value on the basis of reference spectral reflectances of a plurality of color chips of mutually different colors and measurement values and capable of calibrating a measurement value of the sample on the basis of the correction value in such a manner that the measurement value becomes a spectral reflectance of the reference plate.

The optical means of the present invention includes an incident light source, light-detecting means for detecting the quantity of the light reflected by the object to which the light is radiated from the light source, and a plurality of optical filters for allowing the light in predetermined wavelength bands which do not overlap to be transmitted therethrough and for shielding the light other than that in the wavelength bands. The optical means measures the quantity of light reflected by the object by measuring the light transmitted through the optical filter. Accordingly, by changing the optical filters, it is possible to obtain a color-separated output in the wavelength band of the light transmitted through the optical filter, i.e., a channel output. The correcting means determines for each predetermined wavelength band a central wavelength corrected on the basis of a spectral distribution obtained through a combination of at least a spectral distribution of the light source, a spectral transmittance of each of the optical filters, and a spectral sensitivity of the light-detecting means. Accordingly, various calculations effected through the channel output of each channel can be based on the central wavelength determined. The calibrating means calibrates a measurement value of the sample for each central wavelength of the predetermined wavelength bands in such a manner that the measurement value becomes the spectral reflectance of the reference plate. The estimating means estimates a spectral reflectance on the basis of the value calibrated for each central wavelength. Thus, a channel output is obtained by the optical means including the incident light source, optical filters, and the light-detecting means, the central wavelength of the channel output is determined, the calibration of the spectral reflectance of the sample is effected, and the spectral reflectance of the sample is estimated. Accordingly, since the light of predetermined wavelength bands that do not overlap can be transmitted and the light other than that of those wavelength bands can be shielded by means of a plurality of optical filters, it is possible to determine the spectral reflectance independently for each independent channel, thereby facilitating the estimation of the spectral reflectance of the sample.

In addition, an arrangement may be provided such that the correction value is determined on the basis of a reference value and a measurement value of each spectral reflectance of a plurality of color chips of mutually different colors, and the measurement value of the sample is calibrated on the basis of the correction value in such a manner that the measurement value becomes a spectral reflectance of the reference plate. Thus, by measuring a plurality of color chips of mutually different colors (i.e., different hues, lightness, and saturations) serving as a reference at the time of calibration, the calibration can be simplified.

As described above, in accordance with the second aspect of the present invention, the two-dimensional distribution characteristic of the spectral reflectance of the sample can be obtained irrespective of the spectral characteristics which vary in a complex manner owing to elements constituting the optical system, and the spectral reflectance distribution can be obtained through simple calculation processing. Accordingly, there is an advantage in that the two-dimensional distribution of the spectral reflectance can be obtained without making the apparatus large or increasing the processing time.

To attain the above-described objects, in accordance with a third aspect of the present invention, there is provided a three-dimensional automatic gonio-spectrophotometer for measuring a spectral reflectance factor of the wide area, comprising: disposing means for disposing a sample and a reference plate in such a manner as to allow the sample and the reference plate to form a predetermined angle; radiating means for radiating the light from a single light source to the sample and the reference plate; measuring means for measuring respective quantities of the light reflected from the sample and the reference plate for each of predetermined wavelengths or predetermined wavelength bands; angle-changing means for changing angles including the incident angle at which the light from the single light source is radiated to the sample, a light-detecting angle at which the measuring means detects the light from the sample, a rotational angle of the sample rotated about a normal line of the sample, and an azimuth angle formed by a light-detecting plane including the normal line of the sample and a light-detecting optical axis leading to the measuring means, with respect to an incident plane including the normal line of the sample and the incident optical axis leading to the sample; correction-value calculating means in which a plate having a diffusively reflecting surface is disposed at a position where the sample is disposed, for determining a correction value in an angular range other than a regular reflection range on the basis of a reference value measured under a reference angular condition of the plate, and a measurement value of the plate measured under a predetermined angular condition different from the reference angular condition, and for determining a correction value of the regular reflection range by interpolation on the basis of a measurement value of a vicinity of the regular reflection range of the plate under the predetermined angular condition or a correction value of the vicinity of the regular reflection range; and spectral-reflectance-factor calculating means for calculating the spectral reflectance factor of the sample on the basis of the measurement values of the sample and the reference plate measured by the measuring means and the correction value determined by the correction-value calculating means.

In the three-dimensional automatic gonio-spectrophotometer, the light from a single light source is radiated by the radiating means to the sample and the reference plate in such a manner as to allow the sample and the reference plate to form a predetermined angle. Respective quantities of the light reflected from the sample and the reference plate are measured by the measuring means by spectrally separating the light into predetermined wavelengths or predetermined wavelength bands. The spectral reflectance factor of the sample is determined on the basis of each measurement value. A working standard white plate or a reference white plate may be used as this reference plate.

The angle-changing means changes angles including the incident angle of the light radiated to the sample, the light-detecting angle at which the measuring means detects the light from the sample, the rotational angle of the sample rotated about a normal line of the sample, and the azimuth angle formed by a light-detecting plane including the normal line of the sample and a light-detecting optical axis leading to the measuring means, with respect to an incident plane including the normal line of the sample and the incident optical axis leading to the sample. Thus, by changing the respective angles, the positions of the radiating means, the measuring means, the sample, and the like can be changed three-dimensionally, i.e., the aforementioned angles can be changed, so that it becomes possible to obtain the three-dimensional spectral reflectance factor through these measurement values.

Here, in a case where the incident angle is fixed and the light-detecting angle is changed to determine the spectral reflectance factor, if the light is sufficiently radiated to the overall area of the sample (a light-detecting visual field) corresponding to the light-detecting area of the measuring means, the luminance is measured, and the angular distribution of the reflected light has no directionality and becomes a fixed value. However, in a case where the light-detecting angle is large and the light-detecting visual field expands, the light is radiated to an area within this light-detecting visual field, so that a partially reflected flux of light is measured. On the other hand, in a case where the relationship of the various angles concerning the sample is changed three-dimensionally, illuminance sometimes varies in the sample and the reference plate, e.g., a reference white plate. Accordingly, if the spectral reflectance factor is determined three-dimensionally, there are cases where the spectral reflectance factor determined is not appropriate depending on the angular condition. Furthermore, if the incident angle with respect to the sample and a reflecting plate such as a standard plate becomes large, sheen occurs in the direction of regular reflection, i.e., when, for instance, the incident plane and the detecting plane are identical and the incident angle and the light-detecting angle are substantially equal. In such a case, the spectral reflectance factor determined may not be appropriate.

Accordingly, the correction-value calculating means has a plate having a diffusively reflecting surface and disposed at the position where the sample is disposed. With respect to an angular range other than the regular reflection range, the correction-value calculating means determines a correction value of such a range on the basis of a reference value measured under a reference angular condition of the plate and a measurement value of the plate measured under a predetermined angular condition different from the reference angular condition, e.g., on the basis of a ratio. As the plate having the diffusively reflecting surface, it is possible to use a white-coated plate. Meanwhile, with respect to the regular reflection range, the correction-value calculating means determines a correction value of that range by interpolation on the basis of a measurement value of a vicinity of the regular reflection range of the plate under the predetermined angular condition or a correction value of the vicinity of the regular reflection range. The spectral-reflectance-factor calculating means calculates the spectral reflectance factor on the basis of the measurement value of the sample under a predetermined angular condition and a correction value determined by the correction-value calculating means under that angular condition.

Accordingly, if the measurement value of the sample is multiplied by the correction value, the reference luminance characteristics and the light-detecting characteristics, i.e., the measured value can be converted to a spectral reflectance factor measured under the condition at the time of the calibration of the reference plate, e.g., the working standard white plate. As a result, even when the relationship of the various angles concerning the sample is changed three-dimensionally, it is possible to appropriately determine the spectral reflectance factor. Furthermore, even with respect to an angular range for which an appropriate measurement is impossible due to the occurrence of the sheen, it is possible to obtain a spectral reflectance factor corrected optimally.

As described above, in accordance with the present invention, there are advantages in that the three-dimensional spectral reflectance factor can be measured automatically, and that the three-dimensional spectrocolorimetry of an object having a complicated reflection characteristic such as a fabric can be effected easily.

Furthermore, there is an advantage in that even with respect to an angular range where accurate measurement of the reflectance is impossible due to the occurrence of the sheen in the direction of regular reflection, an optimum spectral reflectance factor can be obtained since interpolation is performed by using measurement values or a correction value of a surrounding area.

The other objects, features and advantages of the present invention will become more apparent from the following detailed description of the invention when read in conjunction with the accompanying drawings.

DESCRIPTION OF THE PREFERRED EMBODIMENTS

Figure 1:
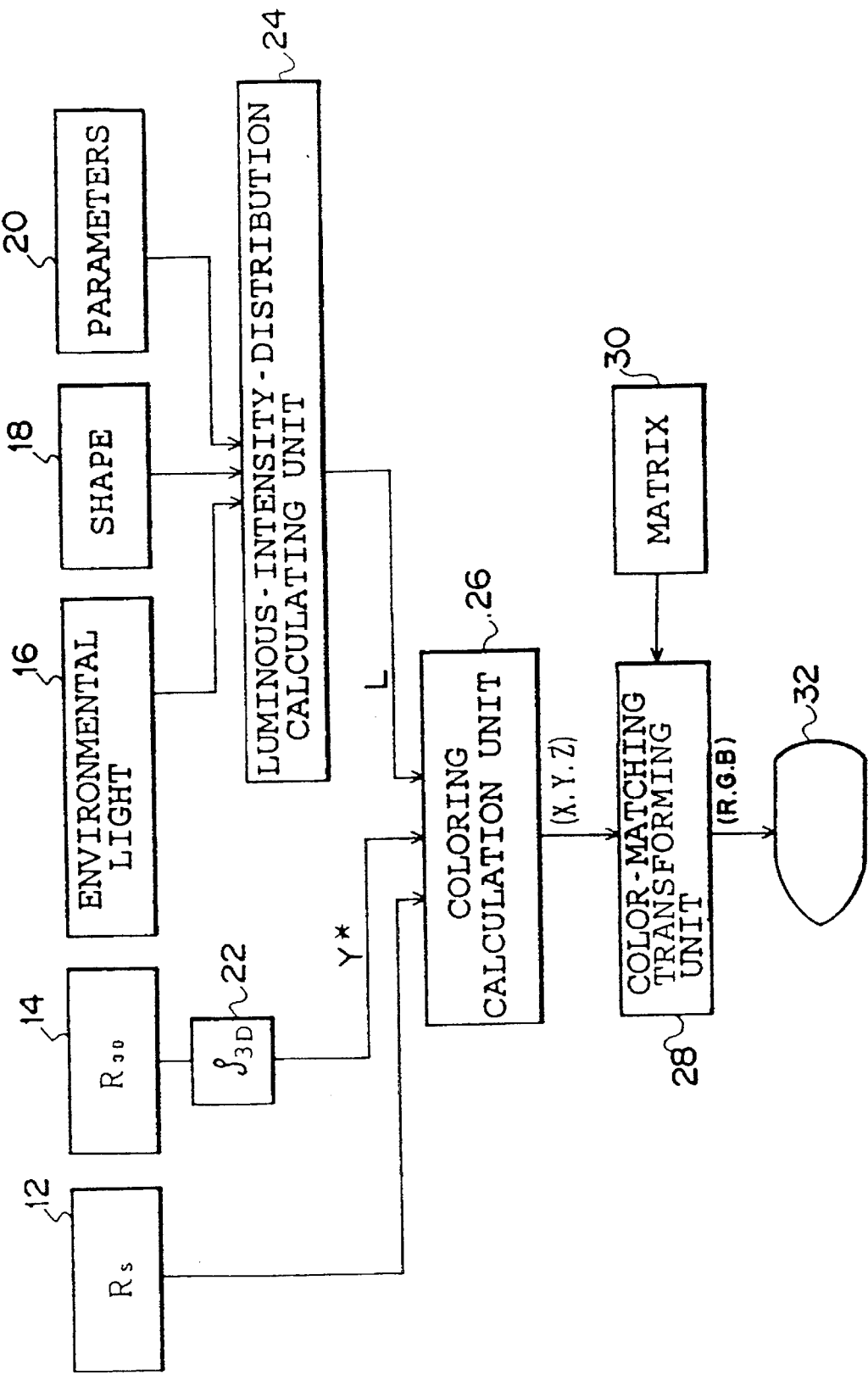
FIG. 1 is a block diagram illustrating a schematic configuration of an embodiment of a rendering apparatus in accordance with the present invention.

Referring now to the accompanying drawings, a detailed description will be given of embodiments of the present invention. FIG. 1 shows an embodiment of a rendering apparatus of the present invention. In this embodiment, the present invention is applied to computer graphics for realistically displaying an object by coloring an image based on a surface model of CAD or the like with the colors of a real object and by displaying the same on the screen.

As shown in FIG. 1, the rendering apparatus of this embodiment has a coloring calculation unit 26. Connected to this coloring calculation unit 26 are a data storage unit 12 for storing spectral reflectances of infinitesimal areas and a data storage unit 14 for storing three-dimensional spectral reflectance factors of a wide area. Although details will be described later, the data stored in the data storage unit 14 are normalized by the spectral reflectance factor under a reference angular condition stored in a data storage unit 22, and are used in the coloring calculation unit 26. In addition, the coloring calculation unit 26 is connected to a luminous-intensity-distribution calculating unit 24.

The luminous-intensity-distribution calculating unit 24 calculates the spectral radiance of the environmental light made incident upon an infinitesimal area, i.e., a spectral radiant energy distribution per unit area and per unit solid angle. Connected to the luminous-intensity-distribution calculating unit 24 are an environmental-light-data storage unit 16 for storing the spectral radiance of the light serving as a light source; a shape data storage unit 18 for storing line data of CAD or the like describing the object surface; and a parameter storage unit 20 for storing a plurality of parameters for designating a pixel and a direction on the screen which respectively correspond to a visual point and a line of sight.

The coloring calculation unit 26 determines the spectral radiance directed from the infinitesimal area of the object surface toward pixels constituting the screen on the basis of the spectral reflectance of the infinitesimal area and the three-dimensional spectral reflectance factor of a wide area which are inputted thereto, and the spectral radiance of the environmental light calculated by the luminous-intensity-distribution calculating unit 24. Then the coloring calculation unit 26 outputs color specification values of the XYZ colorimetric system, i.e., tristimulus values.

Also, the coloring calculation unit 26 is connected to a color-matching transforming unit 28. The color-matching transforming unit 28 transforms the inputted color specification values of the XYZ colorimetric system, i.e., tristimulus values, into color specification values of the RGB colorimetric system in correspondence with coefficient data for color-matching transformation stored in a transformation matrix storage unit 30, and outputs the transformed data to a display unit 32. The display unit 32 displays a color image in accordance with the inputted RGB color specification values.

Next, a description will be given of the principle of outputting tristimulus values of the XYZ colorimetric system (coloring model) in the coloring calculation unit 26.

To reproduce and display a colored pattern and texture of the object surface as an image, i.e., to match the pattern and texture of the viewed object surface with the pattern and texture of the displayed object, it is essential to accurately ascertain the optical properties of the object surface. In other words, the light at a time when the object is viewed becomes the light which is based on the brightness and color affected as a result that the light radiated to the object is diffused on the object surface or transmitted therethrough. Accordingly, the light which reaches the position of the visual point from the object surface is related to the spectral radiance of the light source irradiating the object and the spectral reflectance of the object surface.

Accordingly, in displaying the image of this object, the light of a predetermined spectral radiance is radiated to the object, and the light reflected from the object is specified by being weighted by the spectral reflectance in the infinitesimal area of the object with respect to the colored pattern and texture of the object and by the spectral reflectance factor of a wide area with respect to a change in the brightness due to angular conditions of the object, so as to determine the spectral radiance directed toward the position of the visual point corresponding to the pixel on the screen. The tristimulus values are determined from this spectral radiance. This can be expressed by the following Formula (3):

$$\begin{pmatrix} X \\ Y \\ Z \end{pmatrix} = \frac{1}{k} \int_\lambda \int_\Omega Y_{3D}^*(\lambda, \Phi) \cdot R_S(\lambda, \Phi_o) \cdot L(\lambda, \Theta) \cdot \cos\theta \begin{pmatrix} \bar{x}(\lambda) \\ \bar{y}(\lambda) \\ \bar{z}(\lambda) \end{pmatrix} d\omega d\lambda \quad (3)$$

Where, $R_S(\lambda, \Phi_o)$: spectral reflectance of a very small area at an angular condition $\Phi_o$ $\Phi_o$: angular condition in which an incident angle, a reflection angle, and an azimuth angle are at predetermined values For instance, in scanner measurement, this angular condition include angles formed by the light source on the one hand, and the object and the light-detecting portion on the other (e.g., an incident angle of 45°, a reflection angle of 0°, an azimuth angle of 0°, etc.)

In addition, $Y_{3D}^*$ denotes a normalized reflection ratio which is angle dependent at a wavelength $\lambda$, as shown in the following Formula (4):

$$Y_{3D}^*(\lambda, \Phi) = R_{3D}(\lambda, \Phi)/R_{3D}(\lambda, \Phi^*) \quad (4)$$

Where, $R_{3D}(\lambda, \Phi)$: three-dimensional spectral reflectance factor of a wide area $\Phi^*$: reference angular condition For instance, an angular condition exhibiting the mean value of $R_{3D}(\lambda, \Phi)$ at a time when the angular condition $\Phi$ is changed.

Thus, the light made incident upon an infinitesimal area of the object is reflected in accordance with the spectral reflectance $R_S(\lambda, \Phi_o)$ of this infinitesimal area. This reflected light is weighted by the angular conditions by using the reflection ratio $Y_{3D}^*(\lambda, \Phi)$ normalized by the three-dimensional spectral reflectance factor of a wide area, so as to adjust the brightness. As a result, the relationship between the wavelength dependence of the infinitesimal area and the angular dependence of the wide area can be synthesized, and the brightness which is angle dependent and the color which is dependent on the wavelength in the infinitesimal area can be reproduced. Accordingly, by displaying the reproduced colors of infinitesimal areas with respect to the overall object surface, it is possible to form screen displaying the object with colored patterns and texture which are faithful to the actual object surface.

Hereafter, a description will be given of the operation of this embodiment together with the procedure of rendering.

Figure 4:
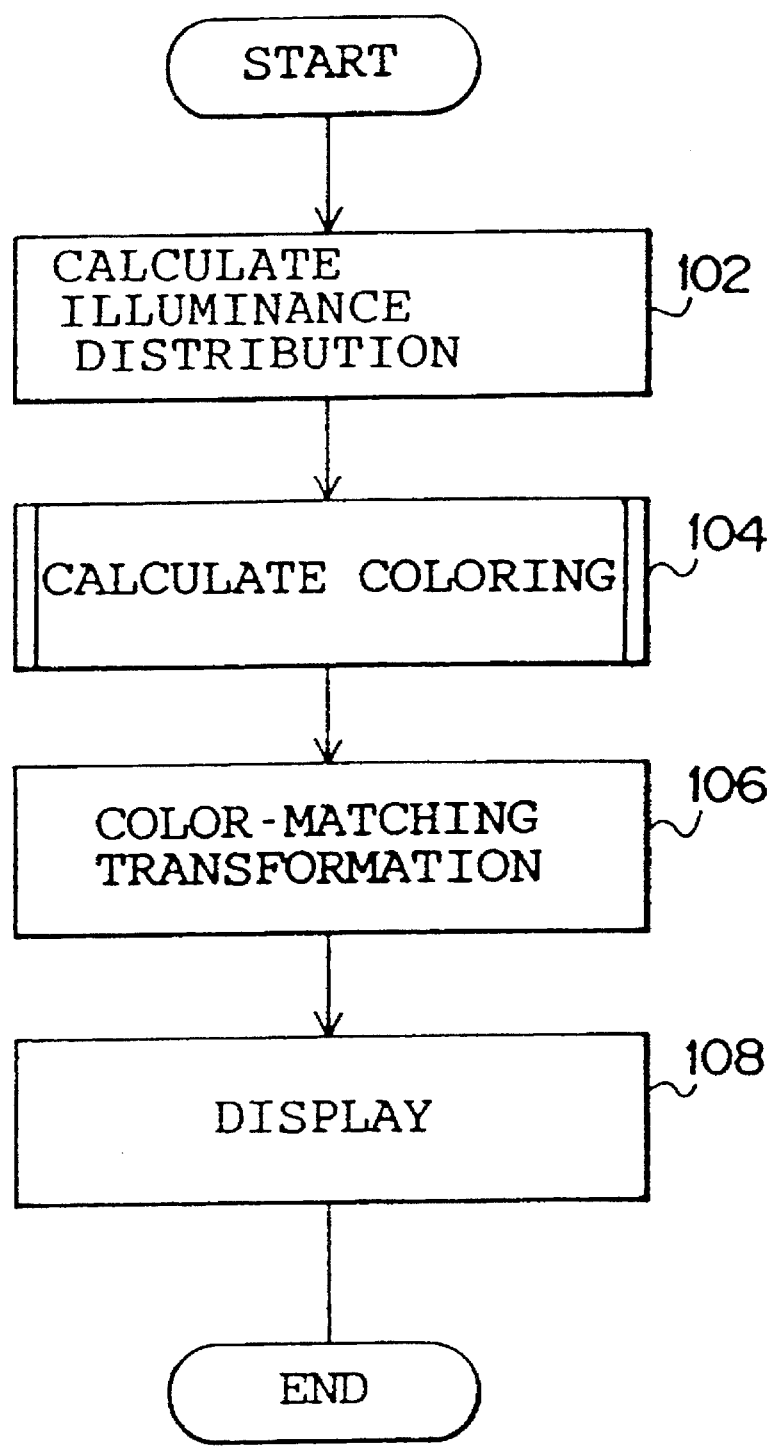
FIG. 4 is a flowchart illustrating the procedure of rendering which includes coloring calculation processing in accordance with the embodiment.

As shown in FIG. 4, in Step 102, the calculation of a luminous intensity distribution is first performed. In this calculation of the luminous intensity distribution, the spectral radiance of the environmental light made incident upon a infinitesimal area of the object surface is determined by the luminous-intensity-distribution calculating unit 24 in accordance with the position of the visual point (a pixel on the screen) designated by the parameter storage unit 20 and the line of sight from the visual point toward the object.

In this embodiment, a three-dimensional ray tracing method is used in this calculation of the luminous intensity distribution. In this ray tracing method, rays of light reaching the visual point from the light source via the infinitesimal area of the object are determined by tracing the rays of light in the opposite direction to that of light, i.e., from the visual point toward the light source. In a case where one or a plurality of other objects, in addition to the object to be irradiated, are present in the optical path during the tracing of the rays of light, reflection or transmission processing is performed in accordance with the optical properties of the other objects.

This ray tracing is carried out by determining the presence or absence of an intersection between the rays of light and the object during tracing. In this embodiment, the shape data stored in the shape data storage unit 18 are used for this determination. It should be noted that it is sufficient if the shape data are stated in terms of a surface model using a polygon or an arbitrary curved surface, and the determination of the presence or absence of the intersection can be made by the presence or absence of a point of intersection determined by the numerical calculation of an algebraic polynomial. In addition, during this processing of ray tracing, a determination is also made as to whether or not the rays of light intersect the light source during tracing.

Accordingly, from the intersection processing for determining the intersection by ray tracing, the spectral radiance L per very small solid angle made incident upon the infinitesimal area of the object surface can be obtained on the basis of the spectral radiance and the like stored in the environmental-light-data storage unit 16 of the light source for irradiating the object. In addition, the ray tracing is conducted not only between the object and the other object or the light source but also between the visual point and the object. As a result, the incident angle with respect to the normal of the object surface can be determined.

In an ensuing Step 104, although details will be described later, a determination is made of the spectral radiance directed from the infinitesimal area of the object surface toward the position (visual point) corresponding to the pixel constituting a part of the screen. Namely, the coloring calculation unit 26 determines a spectral radiance $I(\lambda, \Phi)$ directed from the infinitesimal area of the object surface based on a coloring model shown in Formula (3) above toward a pixel on the screen. At this time, for the purpose of calculation of reflection on the infinitesimal area of the object area, the spectral reflectance of the infinitesimal area stored in the data storage unit 12 is related to the position of a pattern and texture surface constituting the color of the infinitesimal area. In addition, in accordance with the condition of the angle between the incident rays of light and the pixel, the three-dimensional spectral reflectance factor of a wide area stored in the data storage unit 14 is used. Then, the spectral radiance $I(\lambda, \Phi)$ thus determined is transformed into color specification values of the XYZ colorimetric system by using the CIE standard color matching functions.

In an ensuing Step 106, the XYZ color specification values (tristimulus values) obtained are transformed into color specification values of the RGB colorimetric system. That is, the XYZ color specification values obtained in the coloring calculation unit 26 are transformed into the RGB colorimetric system by the RGB color-matching transforming unit 28 by using a transformation matrix stored in the transformation matrix storage unit 30. These transformed color specification values are further subjected to correction transformation into RGB gradients by using respective $\gamma$ correction curves of RGB. One pixel transformed into these RGB gradients is displayed in the display unit 32, i.e., on the screen (Step 108).

The image data of one screen are formed by repeating the above-described procedure with respect to all the pixels on the screen of the display unit 32. Accordingly, a realistic three-dimensional image is formed in the display unit 32 displaying the image based on the image data of one screen.

Figure 2:
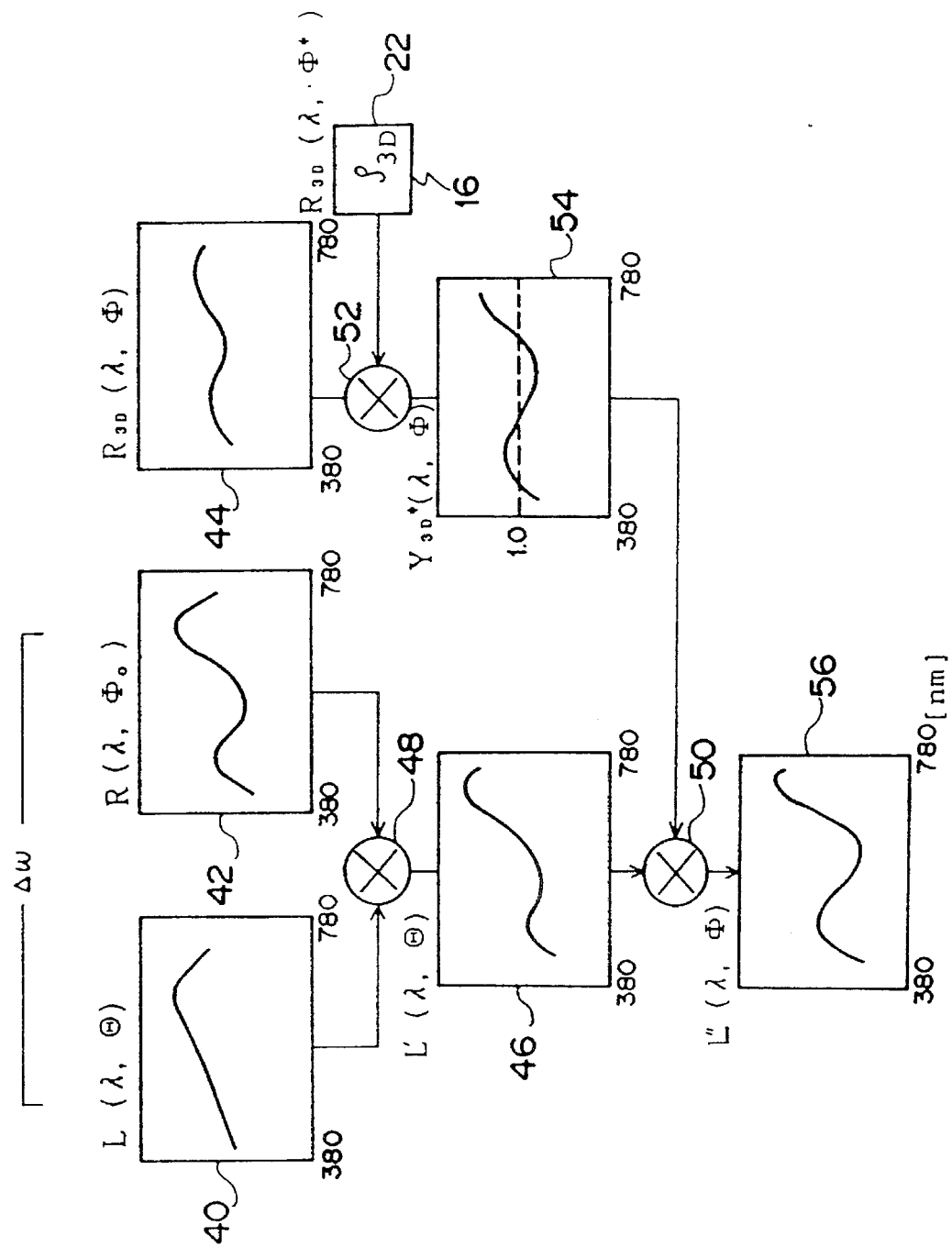
FIG. 2 is an image diagram illustrating a process for determining the spectral radiance of the light directed toward a visual point.
Figure 3:
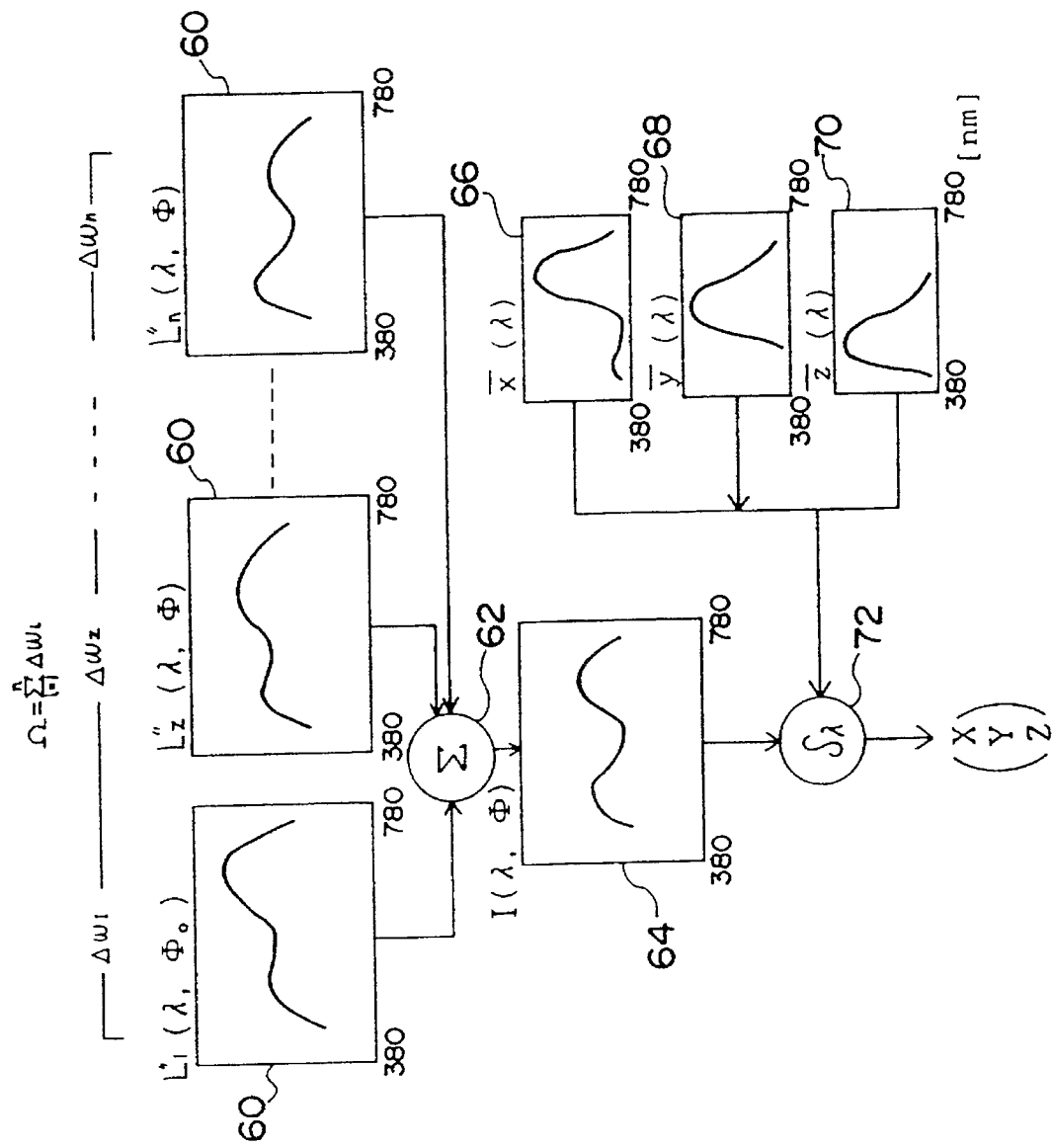
FIG. 3 is an image diagram illustrating a process for determining color specification values of the XYZ colorimetric system from the spectral radiance of the light directed toward the visual point of a total solid angle.
Figure 5:
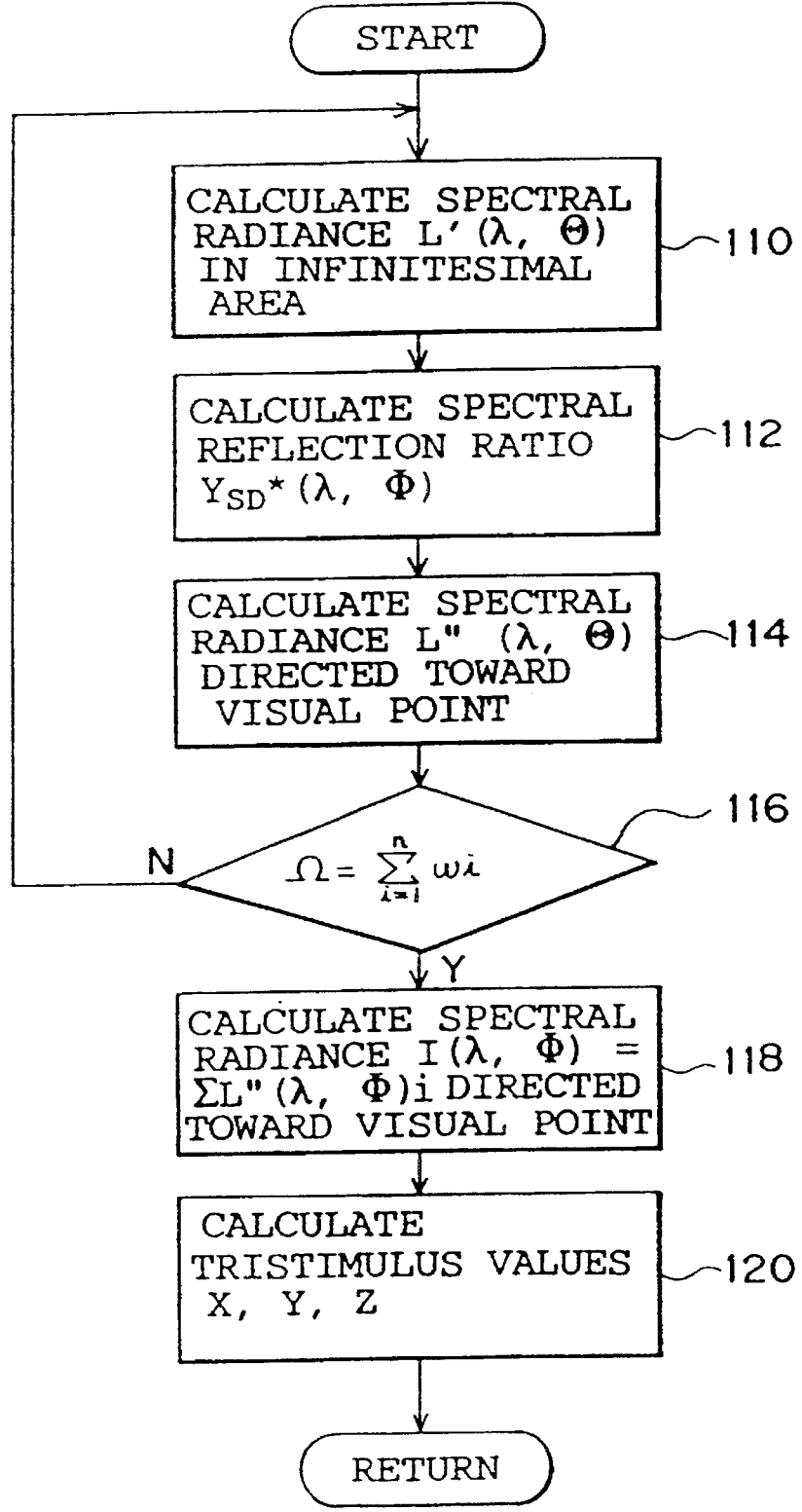
FIG. 5 is a flowchart illustrating the coloring calculation processing in accordance with the embodiment.

Referring now to FIGS. 2, 3 and 5, a detailed description will be given of the coloring calculation processing in the above-described Step 104.

First, the light having a spectral radiance 40 and made incident upon the infinitesimal area becomes the light which radiates a spectral radiance L' shown by a characteristic 46 in accordance with a spectral reflectance 42 of this infinitesimal area. In this embodiment, the spectral radiance $L(\lambda, \Theta)$ made incident upon the infinitesimal area of the object surface at a very small solid angle $\Delta\omega$ determined in the luminous-intensity-distribution calculating unit 24, and the spectral reflectance $R(\lambda, \Phi)$ in the infinitesimal area stored in the data storage unit 12 are synthesized (e.g., multiplied), so as to determine the spectral radiance $L'(\lambda, \Theta)$ in the infinitesimal area (Step 110).

Next, the angle-dependent spectral reflection ratio $Y_{3D}^*(\lambda, \Phi)$ at the wavelength $\lambda$ is determined in which the three-dimensional spectral reflectance factor $R_{3D}(\lambda, \Phi)$ of the wide area of the object stored in the data storage unit 14 is normalized by a coefficient $\rho_{3D}$ which is the three-dimensional spectral reflectance factor $R_{3D}(\lambda, \Phi^*)$ under the reference angular condition $\Phi^*$ stored in the data storage unit 22 (Step 112). This spectral reflection ratio $Y_{3D}^*$ has a characteristic 54 in which a three-dimensional spectral reflectance factor $R_{3D}$ with a characteristic 44 is synthesized by synthesizing calculation processing 52 by using the coefficient $\rho_{3D}$. The brightness of the object can be adjusted by means of this reflection ratio $Y_{3D}^*$.

The spectral radiance $L''(\lambda, \Theta)$ directed toward the visual point is determined by using the spectral radiance L' in these infinitesimal areas and the spectral reflection ratio $Y_{3D}^*$ (Step 114). In this case, the spectral radiance L'' has a characteristic 56 which is obtained by synthesizing (e.g., multiplying) the spectral radiance L' with the characteristic 46 and the reflection ratio $Y_{3D}^*$ with the characteristic 54 by synthesizing calculation processing 50.

Accordingly, the light made incident upon the infinitesimal area of the object area at the very small solid angle $\Delta\omega$ has the spectral radiance $L''(\lambda, \Phi)$, which is reflected with the wavelength-dependent reflectance, is conditioned by an angle-dependent reflection ratio to satisfy the angular condition for orientation toward the visual point, and is directed toward the visual point.

Next, since the total solid angle $\Omega$ as viewed from the infinitesimal area is formed by the sum ($\Omega=\Sigma\omega i$) of very small solid angles $\Delta\omega i$ (i=1, 2, . . . , n), the above-described processing is effected for each very small solid angle $\Delta\omega i$. Then, the spectral radiance $L''i$ for each very small solid angle $\Delta\omega i$ is determined, and the sum of the spectral radiances $L''i$ is determined by summing calculation processing 62, so as to determine the spectral radiance $I(\lambda, \Phi)$ in which the light made incident at the total solid angle $\Omega$ is reflected by the infinitesimal area and is directed toward the visual point (Steps 116, 118).

With respect to the spectral radiance I thus determined, three color-matching functions having spectral characteristics 66, 68, 70 are synthesized and are integrated by integrating calculation processing 72, to determine tristimulus values XYZ of the XYZ colorimetric system (Step 120), and the coloring calculation processing ends.

It should be noted that the aforementioned spectral radiance I can also be obtained by performing reflection/transmission processing while reversely tracing the optical path as in the above-described ray tracing method, and by finally effecting totalization in units of pixels.

As described above, in this embodiment, the colors of infinitesimal areas can be changed by determining the light radiated from the object surface by using the characteristics of the light source and the spectral reflectances of the object area. In addition, by using the three-dimensional spectral reflectance factors of the object, an image in which the brightness changes in accordance with three-dimensional angular conditions can be formed on the screen. Accordingly, even if the angle at which the object is viewed, i.e., the position of the visual point, and the type of light source for irradiating the object are changed freely, an image which is correspondingly faithful thereto can be formed on the screen.

Although, in the above-described embodiment, a description has been given of the case where an object having a fine colored pattern and texture on its surface is rendered, a description will next be given of a case where a solid-color object is rendered as another embodiment.

This embodiment is based on the fact that since the change in the colored pattern and texture of a solid-color object is very small, even if the spectral reflectances are averaged, no large effect is exerted on the image formed in the display unit.

That is, the role of the spectral reflectance $R_S(\lambda, \Phi_o)$ of a infinitesimal area at a reference angular condition $\Phi_o$ in the coloring model in Formula (3) above, and the role of the three-dimensional spectral reflectance factor $R_{3D}(\lambda, \Phi)$ under the angular condition $\Phi$ are exchanged. Furthermore, as for the reflection ratio, the mean value of spectral reflectances in a predetermined area which is on the fundamental plane of pattern data is determined, and the spectral reflectance is normalized by that mean value. This can be expressed by the following Formula (5):

$$\begin{pmatrix} X \\ Y \\ Z \end{pmatrix} = \frac{1}{k} \int_\lambda \int_\Omega Y_s^*(\lambda, \Phi_o) \cdot R_{3D}(\lambda, \Phi) \cdot L(\lambda, \Theta) \cdot \cos\theta \begin{pmatrix} \bar{x}(\lambda) \\ \bar{y}(\lambda) \\ \bar{z}(\lambda) \end{pmatrix} d\omega d\lambda \quad (5)$$

where Ys* denotes a spectral reflection ratio normalized by the mean spectral reflectance of a predetermined area, as shown in the following Formula (6):

$$Y_s^*(\lambda,\Phi_o) = R_s(\lambda,\Phi_o) / \int R_s(\lambda,\Phi_o)ds / \int ds \qquad (6)$$

In this case, the light made incident upon the infinitesimal area of the object is normalized by the mean spectral reflectance of this infinitesimal area, and reflects the brightness based on the angular condition concerning the three-dimensional spectral reflectance factor of a wide area. Hence, it is possible to reproduce the brightness which is angle dependent. Accordingly, it is possible to display an image of the object which exhibits subtle changes in brightness.

It should be noted that an angle-dependent, normalized luminance ratio can be imparted instead of the angle-dependent, normalized reflection ratio, which has been described in connection with Formula (4) in the above-described embodiment. Namely, in this case, an angle-dependent, normalized luminance ratio which is shown in Formula (7) below is imparted by replacing the angle-dependent, normalized reflection ratio $Y_{3D}^*(\lambda, \Phi)$ shown in Formula (4) above. Accordingly, Formula (4) above imparts a change in brightness at a normalized reflection ratio, whereas this Formula (7) is capable of imparting the change in brightness at a luminance ratio which incorporates the visual sensitivity, so that it is possible to obtain a value close to the brightness viewed by the eye. Nevertheless, since the spectral distribution of the light source which serves as a reference in determining the luminance is used, this method does not directly reflect the spectral radiance of the incident light at the time of calculation.

$$Y_{3D}^*(\Phi) = Y_{3D}(\Phi)/Y_{3D}(\Phi^*) \qquad (7)$$

where, $$Y_{3D}(\Phi) = 1/k' \int C(\lambda) \cdot R_{3D}(\lambda, \Phi) \cdot \bar{y}(\lambda) d\lambda \qquad (8)$$

where, $C(\lambda)$: spectral distribution of the light source serving as a standard $k'$: normalization coefficient In addition, the normalized luminance ratio shown in Formula (9) below may be imparted by replacing the spectral reflection ratio $Y_s^*(\lambda,\Phi_o)$ normalized by the mean spectral reflectance shown in Formula (6) in the above-described embodiment.

$$Y_S^*(\Phi_o) = Y_S(\Phi_o) / \bar{Y}_S(\Phi_o) \qquad (9)$$

where, $$Y_S(\Phi_o) = 1/k' \int C(\lambda) \cdot R_S(\lambda,\Phi_o) \cdot \bar{y}(\lambda) d\lambda \qquad (10)$$

$$\bar{Y}_S(\Phi_o) = \int Y_S(\Phi_o) ds / \int ds \qquad (11)$$

It should be noted that Formula (7) or (9) above can be calculated in advance since the spectral distribution $C(\lambda)$ of the light source serving as a standard is already known.

As described above, if the rendering apparatus of this embodiment is used, it is possible to display a realistic object image three-dimensionally with a small amount of data, so that the rendering apparatus of this embodiment can be used suitably and easily for designing in industrial design, the evaluation of the colors or texture of a material, interior illumination design, and the like.

Next, with reference to the drawings, a detailed description will be given of an embodiment of a multispectral image scanner for measuring the spectral reflectance in the rendering apparatus of the above-described embodiment.

Figure 6:
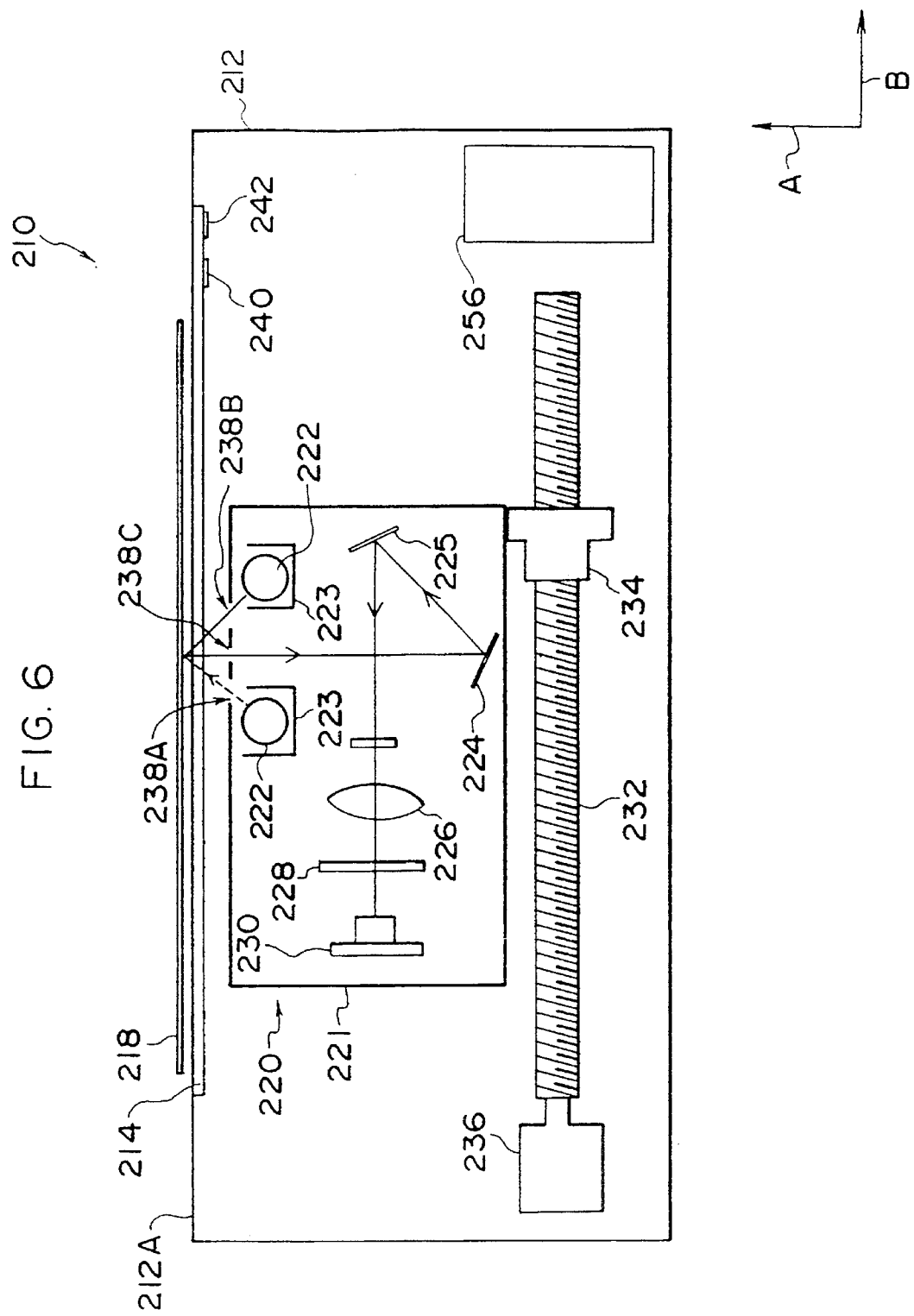
FIG. 6 schematic diagram illustrating an outline of a multispectral image scanner to which the present invention is applied.

As shown in FIG. 6, in a multispectral image scanner 210 of this embodiment, a sample base 214 made of transparent glass is disposed on an upper surface 212A of a casing 212. A sample 218 to be colorimetrically measured can be mounted on this sample base 214.

Figure 7:
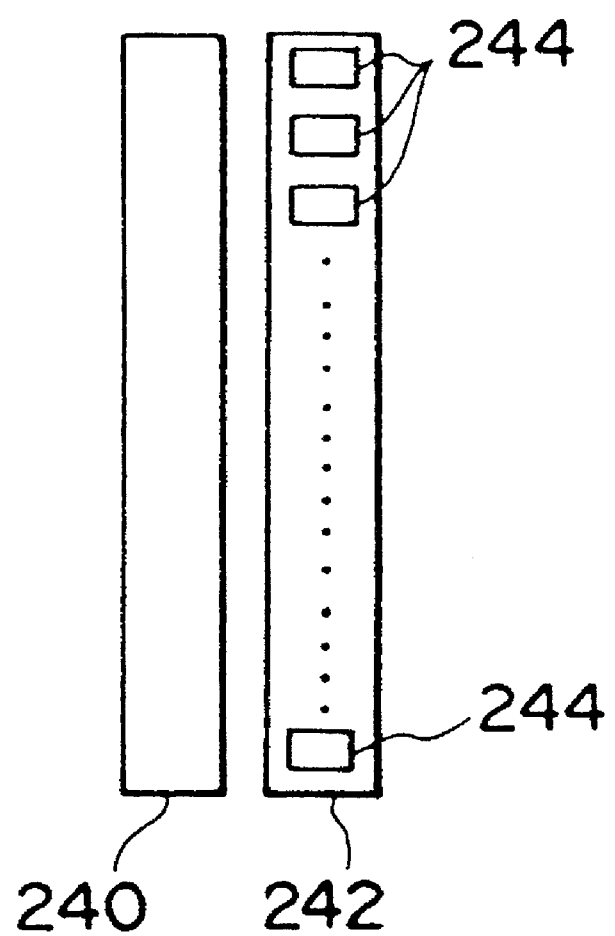
FIG. 7 is an image diagram illustrating the layout of standard luminous white paper and a strip of color chips.

Standard luminous white paper 240 and a color-chip strip 242 which is arranged in the form of a belt and has a plurality of color chips serving as standards are disposed side by side in the vicinity of one end (on the side indicated by arrow B in FIG. 6) of this sample base 214. In this color-chip strip 242, about 50 color chips whose hue, saturation, and lightness differ are arranged in a row so that the light of two light sources 222 is radiated simultaneously (see FIG. 7).

A scanner optical system 220 is disposed in the casing 212 below the sample base 214. The scanner optical system 220 is accommodated in a scanner casing 221, and is comprised of mirrors 224 and 225, a lens 226, a filter turret 228, and a CCD sensor 230.

In this embodiment, a fluorescent lamp having the function as a line light source is used as the light source 222 so as to be able to simultaneously radiate one-line light to the sample 218. The light sources 222 are disposed substantially in parallel with a measurement surface of the sample 218 (in a direction perpendicular to the plane of FIG. 6). It should be noted that this light source 222 may also be a white light source such as a halogen lamp. The two light sources 222 are disposed in an upper position inside the scanner casing 221 so as to irradiate the sample uniformly from the left and the right and to increase the quantity of light. A cover 223 having a U-shaped cross section is disposed around each of the light sources 222 so as to direct the light emitted from the light source 222 only in the upward direction (in the direction of arrow A in FIG. 6). Three slots 238A, 238B, and 238C are formed on an upper surface of the scanner casing 221 at substantially equal intervals and substantially in parallel, and the two light sources 222 are respectively located in accordance with the slots 238A and 238B which are located on the outer sides among the three slots 238A, 238B, and 238C. In addition, the light sources 222 are located such that the optical axes of the light emitted from the light sources 222 and passing through the slots 238A and 238B form about 45° as the incident angle with respect to the sample 218, and that the light emitted from the two light sources 222 irradiates an identical portion of the sample 218 above the slot 238C. The mirror 224 is disposed vertically below the portion of the sample irradiated by the light sources 222 (in the opposite direction to the direction of arrow A in FIG. 6). The light reflected by the sample 218 is guided to this mirror 224, and the light reflected by the mirror 224 is guided to the lens 226 via the mirror 225. The filter turret 228 and the CCD sensor 230, which will be described later, are disposed in that order on the emergent side of the lens 226, and the light made incident upon the lens 226 is focused on the CCD sensor 230 via the filter turret 228. This CCD sensor 230 is connected to a controller 256.

A screw 232 is disposed below this scanner optical system 220, and a rotating shaft of the screw 232 and the sample base 214 are set in parallel with each other. A nut 234 is threadedly engaged on this screw 232, and the scanner optical system 220 is secured to this nut 234. In addition, a rotating shaft of a motor 236 fixed to the casing 212 by means of an unillustrated mounting member is secured to the screw 232. As the motor 236 rotates, the nut 234 moves in a direction along the rotating shaft (in the direction of arrow B and in the opposite direction thereto in FIG. 6). This motor 236 is connected to the controller 256, and rotates in response to a control signal from the controller. Accordingly, the scanner optical system 220 moves in parallel along the sample base 214 in response to the control signal from the controller. It should be noted that, instead of the aforementioned screw, a pinion gear, a belt, or the like may be used as the moving mechanism for the scanner optical system to transmit the rotation of the motor.

Figure 8:
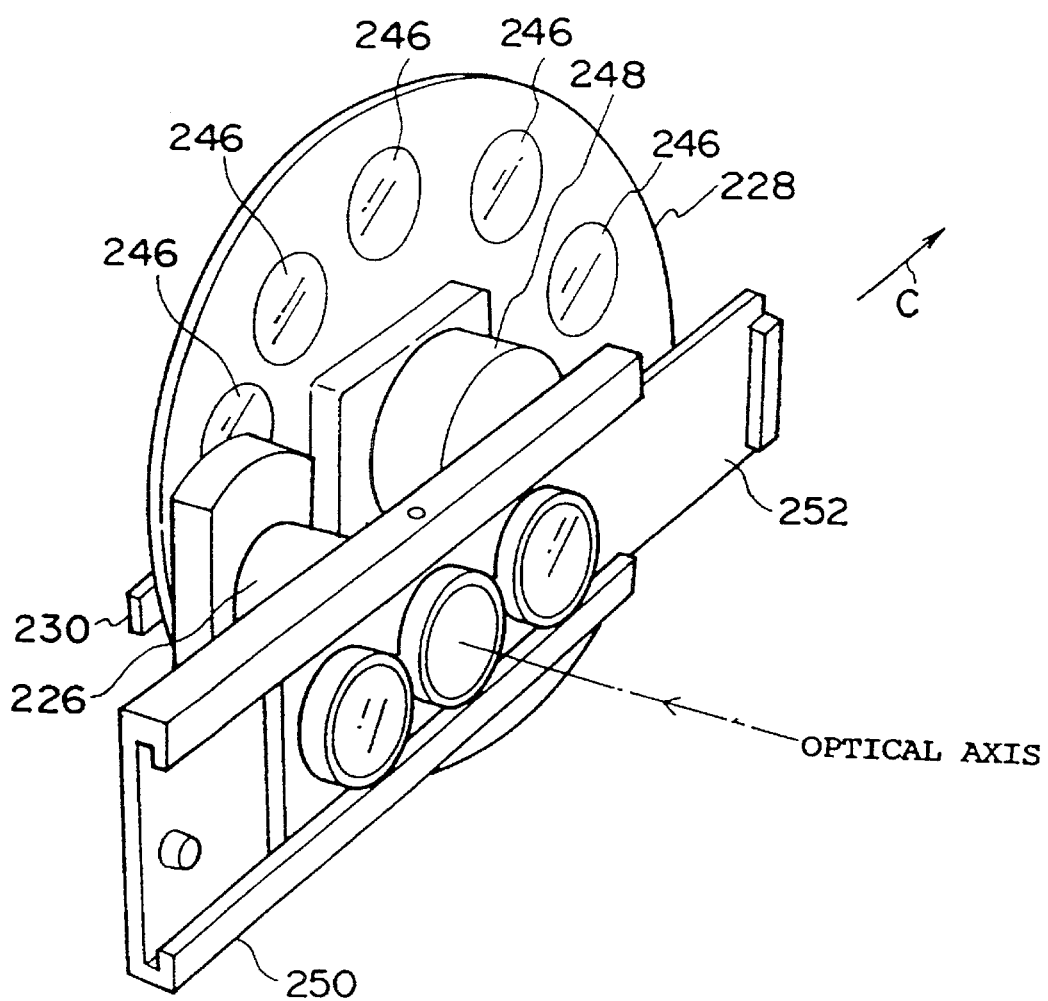
FIG. 8 is a perspective view illustrating the structure surrounding a filter turret in accordance with this embodiment.
Figure 9:
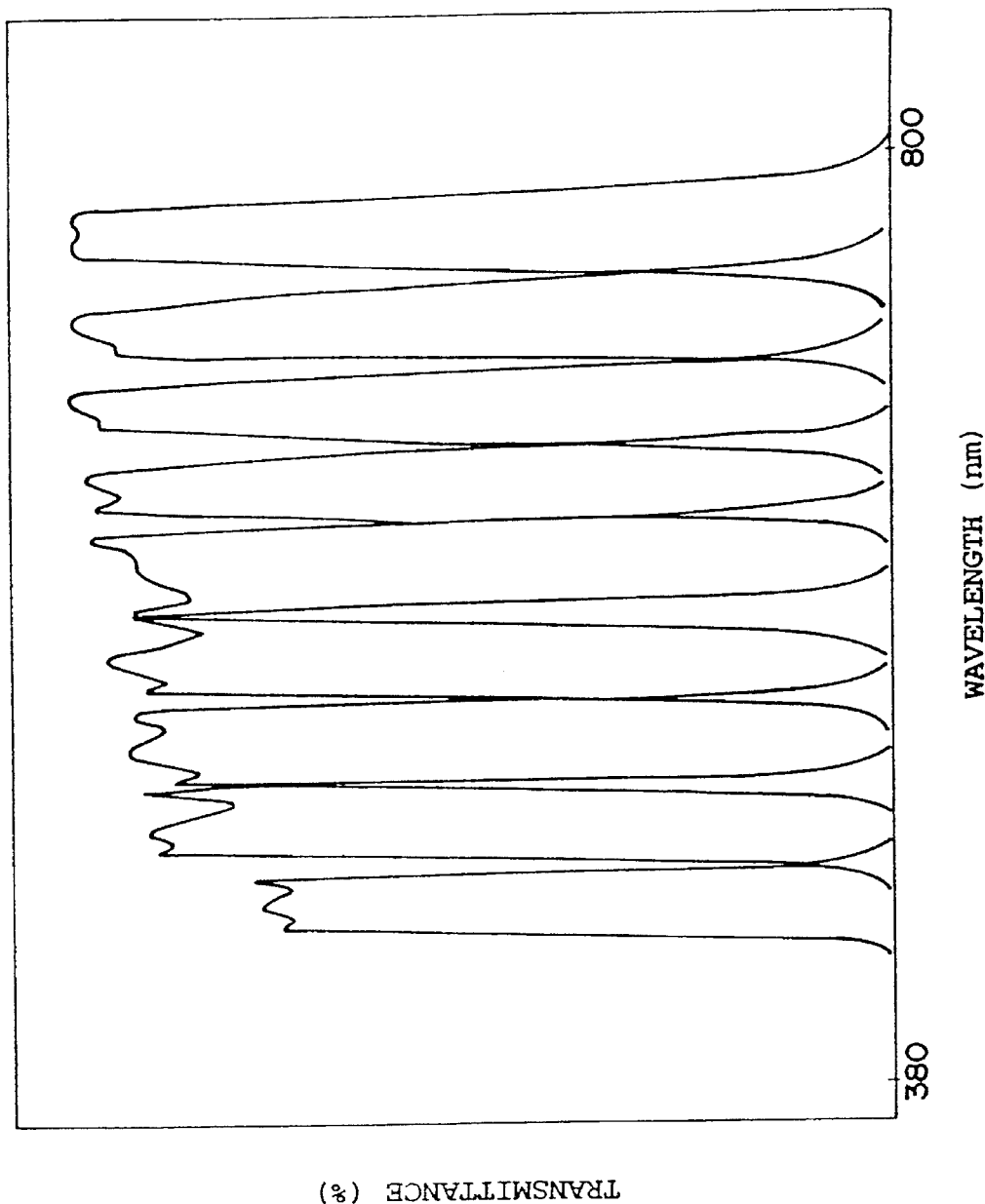
FIG. 9 is a diagram illustrating a characteristic curve of the spectral transmittance of interference filters used in this embodiment.

As shown in FIG. 8, a plurality of (in this embodiment, nine) interference filters 246 are arranged in the aforementioned filter turret 228 on a circumference having a motor 248 as a center. Each of the interference filters 246 has a spectral transmittance characteristic exhibiting a substantially rectangular transmittance distribution with a substantially fixed transmittance in a narrow band, as shown in FIG. 9. The filter turret 228 is disposed between the lens 226 and the CCD sensor 230 and is rotatable in such a manner that the optical axis is located in the vicinity of the center of the interference filter 246. The rotating shaft of the motor 248 constituted by a stepping motor or the like is secured at the rotational axis of this filter turret 228. This motor 248 is connected to the controller 256, and rotates to an angle of rotation corresponding to a control signal from the controller. Accordingly, the interference filters 246 each having a predetermined wavelength band can be consecutively selected as the motor 248 rotates in response to the control signal from the controller.

A filter unit comprised of a filter guide 250 and a filter plate 252 is disposed on the incident side of the lens 226. A plurality of (in this embodiment, three) optical filters are disposed in this filter plate 252, and as the filter plate 252 is moved (in the direction of arrow C in FIG. 8), the filters can be fixedly disposed in the optical axis. Sharp cut filters or light-attenuating filters (neutral density (ND) filters or the like) can be used as these optical filters. By the insertion of the sharp cut filters, it is possible to further narrow the wavelength bands of the predetermined interference filters, and by the insertion of the light-attenuating filters, it is possible to absorb disturbing light when the reflectance of the sample 218 is high.

Figure 10:
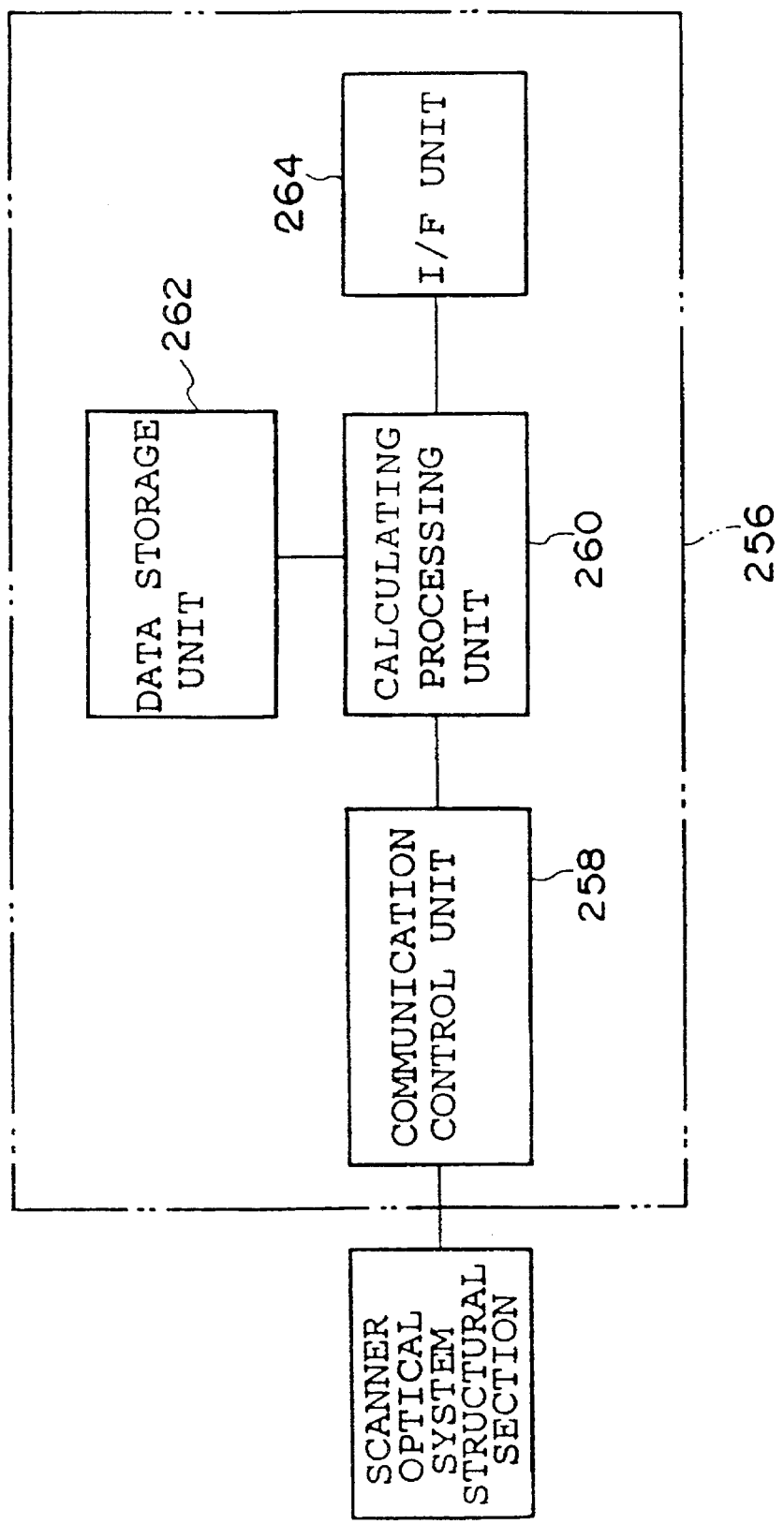
FIG. 10 is a block diagram illustrating a schematic configuration of a controller in accordance with this embodiment.

As shown in FIG. 10, the controller 256 is comprised of a communication control unit 258, a calculating and processing unit 260, a data storage unit 262, and an interface unit 264. The communication control unit 258 has one end connected to structural portions of the scanner optical system 220, i.e., the motor 248 for rotating the filter turret 228, the CCD sensor 230, and the motor 236 (see FIG. 6), and the other end connected to the calculating and processing unit 260. Accordingly, the communication control unit 258 controls the driving of the scanner optical system 220, and effects the transmission and reception of measured data. The calculating and processing unit 260 performs calculation for controlling the scanner optical system 220 and processes the measured data which has been measured by the scanner optical system 220. This calculating and processing unit 260 is connected to the data storage unit 262 and the interface unit 264. It should be noted that the central wavelength of each channel, which is set on the basis of measurement (details will be described later), and a correction value C for calibration are stored in the data storage unit 262. Also stored in the data storage unit 262 are the spectral reflectances of the color chips 244 corresponding to the respective channels measured in advance by a reference device or the like for measuring spectral reflectances. A host computer and output units such as a CRT and a printer are connected to the interface unit 264, and the transmission and reception of commands and data are performed by this interface unit 264 so as to output the calculated values determined by the calculating and processing unit 260.

Here, a description will be given of the spectral measurement of a infinitesimal area, as an area to be measured, and the surface in accordance with this embodiment.

Figure 11:
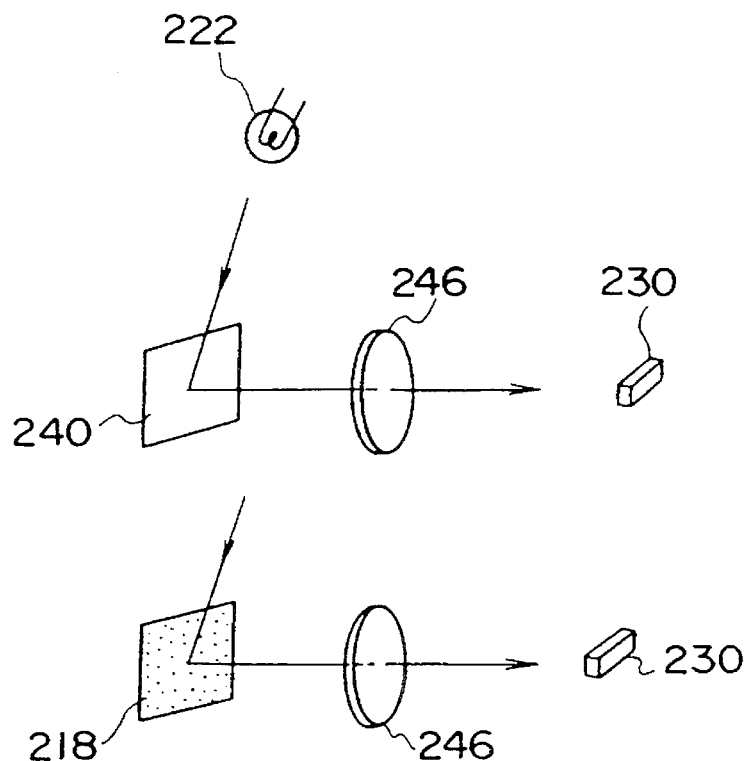
FIG. 11 is a perspective view illustrating a calibration principle in accordance with this embodiment.

As shown in FIG. 11, the quantity of light emitted from the light sources 222 and reflected from the standard luminous white paper 240 is measured by the CCD sensor 230 with respect to all of the plurality of interference filters 246, and calibration is conducted such that the output values of the multispectral image scanner 210 becomes a maximum value (e.g. 255) with respect to each of the interference filters 246.

Then, the sample 218 is placed on the sample base 214, and the amount of reflected light Pi (i=1, 2, . . . , n; n is the number of elements of the CCD sensor 230) of the sample 218 due to the light sources 222 is measured for all of the interference filters 246. During this measurement, measurement is carried out for each element of the CCD sensor 230. From this amount of reflected light Pi, the spectral reflectance ri (i=1, 2, . . . , n) is determined on the basis of the following Formula (12):

$$ri = Pi/256 \qquad (12)$$

As a result, it is possible to obtain the spectral reflectance with respect to the interference filter 246, i.e., for each channel, with respect to each element of the CCD sensor 230. Accordingly, the spectral reflectance of the infinitesimal area, which constitutes one element of the CCD sensor 230, can be determined. At the same time, by determining the spectral reflectance for each element of the CCD sensor 230 that corresponds to all the pixels of one screen, it is possible to obtain a two-dimensional distribution of the spectral reflectances for each channel, i.e., for each wavelength band. By using the spectral reflectances corresponding to the respective pixels in the two-dimensional distribution of the spectral reflectances for each channel, a distribution profile of the spectral reflectances of the pixels is determined by interpolation. By determining the distribution profile of the spectral reflectances with respect to all the pixels, a two-dimensional distribution of the distribution profiles of the spectral reflectances of the sample is obtained.

A description will be given hereafter of the operation of this embodiment.

Figure 15:
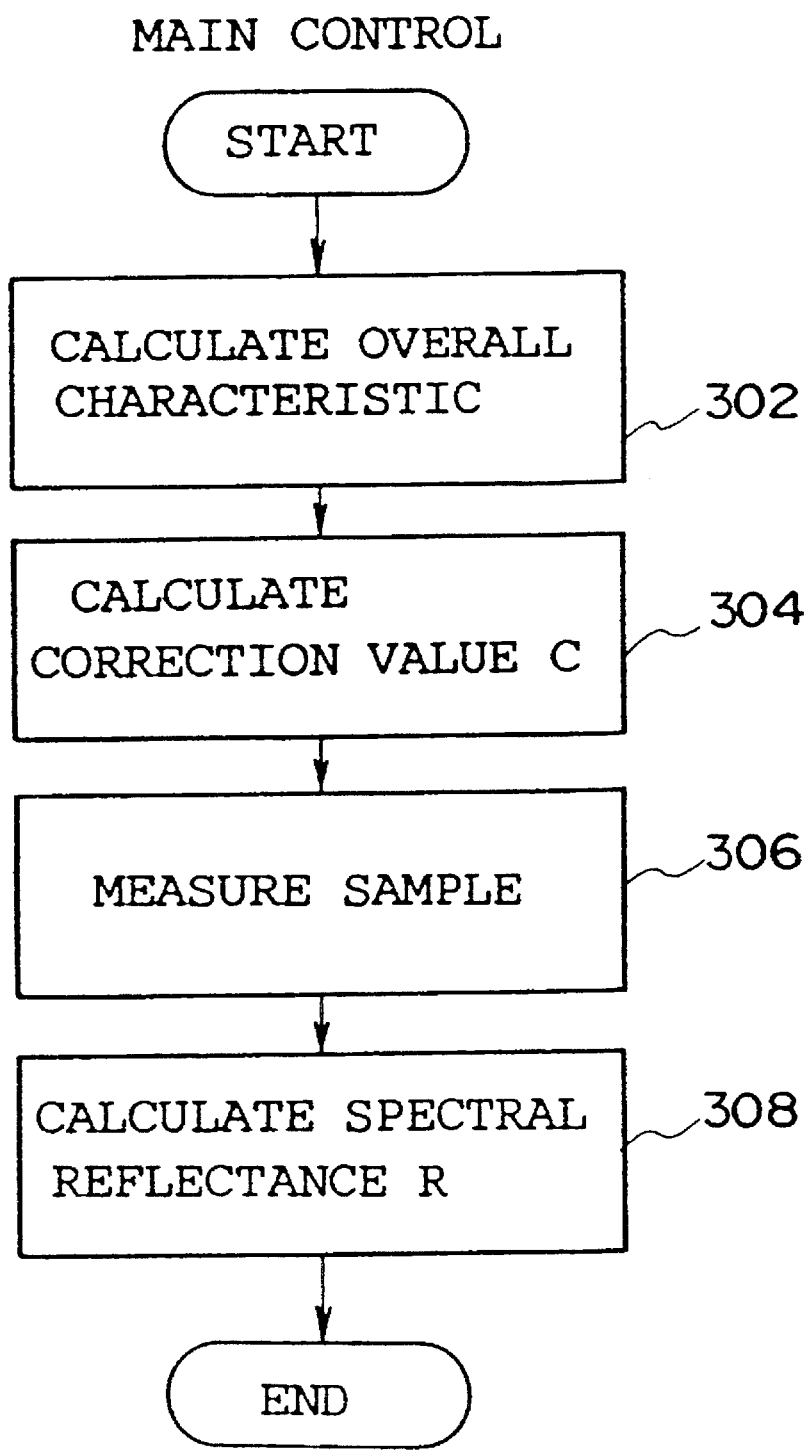
FIG. 15 is a flowchart illustrating a main routine of this embodiment.

First, by referring to a control routine of the multispectral image scanner 210 shown in FIG. 15, a description will be given of an outline of calibration and measurement. In Step 302, a determination is made of the central wavelength for each channel due to each interference filter 246 and an overall characteristic by comprehensively taking into account the spectral distribution of the light sources 222, the spectral transmittance characteristic of each interference filter 246, and the spectral sensitivity characteristic of the CCD sensor 230, and the data thus obtained are stored in the data storage unit 262. In an ensuing Step 304, a determination is made of the correction value C for calibrating the measured values, obtained by measuring the sample 218, with the color chips 244, and the data thus obtained are stored in the data storage unit 262. This correction value C can be obtained by determining the spectral reflectances by measuring the color chips 244 for the respective channels, then by performing regression processing with respect to a plurality of measured values for the respective central wavelengths on the basis of the reference spectral reflectances of the color chips 244 stored in advance, and by determining a regression coefficient of that processing.

In an ensuing Step 306, the sample 218 is measured for each channel corresponding to the wavelength band of each interference filter 246. The measured values of the sample 218 are normalized by values obtained by measuring the standard luminous white paper 240 by using the scanner optical system 220, and are transmitted from the communication control unit 258 to the calculating and processing unit 260 as gradients. The measured values of this sample 218 are calibrated by the correction value C in the calculating and processing unit 260. Each of these values is stored in the data storage unit 262 as the spectral reflectance of the pixel by being made to correspond to the central wavelength. On the basis of the discrete spectral reflectances thus obtained, in an ensuing Step 308, a distribution profile of continuous spectral reflectances is estimated. The distribution profiles of the spectral reflectances, together with the central wavelengths, are stored in the data storage unit 262, and are outputted to the output units such as the CRT and the printer by the interface unit 264. The processing for determining the spectral reflectances is carried out repeatedly for each pixel, i.e., for each element of the CCD sensor 230, and the spectral reflectances of the pixels of the overall screen are finally obtained.

The changing of the aforementioned channel, i.e., the changing of the interference filter 246, is effected by rotating the filter turret 228. Namely, as the motor 248 is rotated to a predetermined angle in response to a control signal outputted from the communication control unit 258, the interference filter 246 is changed to one having a predetermined transmission wavelength band.

In addition, the measurement of the sample 218 placed on the sample base 214 is effected by the scanning of the scanner optical system 220. That is, as the motor 236 is rotated in response to the control signal outputted from the communication control unit 258, the scanner optical system 220 is moved along the surface of the sample 218 (in the direction of arrow B and in the opposite direction thereto in FIG. 6). Accordingly, the light sources 222 move along the surface of the sample 218, and through this movement the light from the light sources 222 is consecutively radiated to the overall surface of the sample 218.

Figure 16:
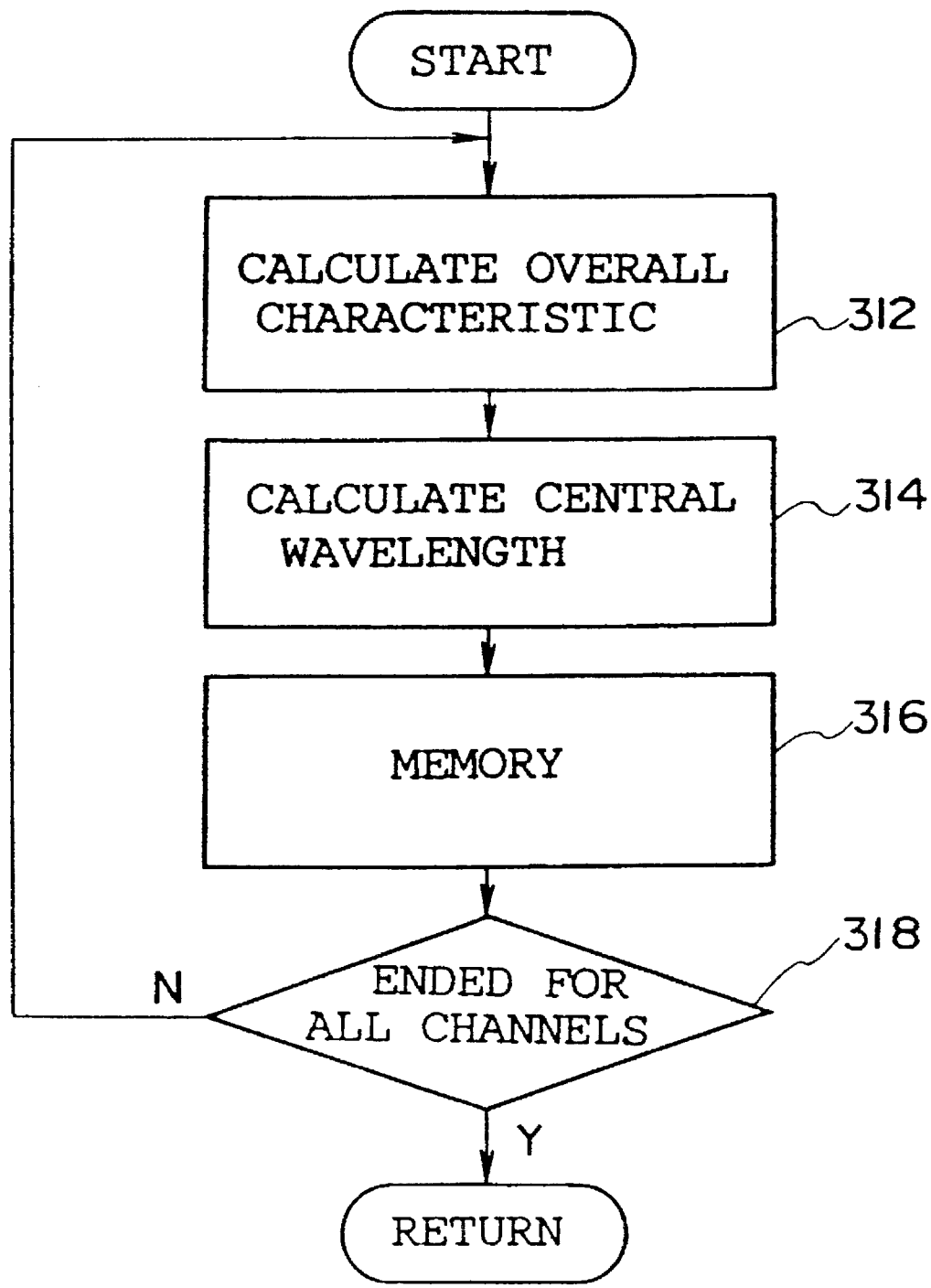
FIG. 16 is a flowchart illustrating a routine for calculating the overall characteristic in accordance with this embodiment.

Referring now to FIG. 16, a detailed description will be given of Step 302.

Figure 13:
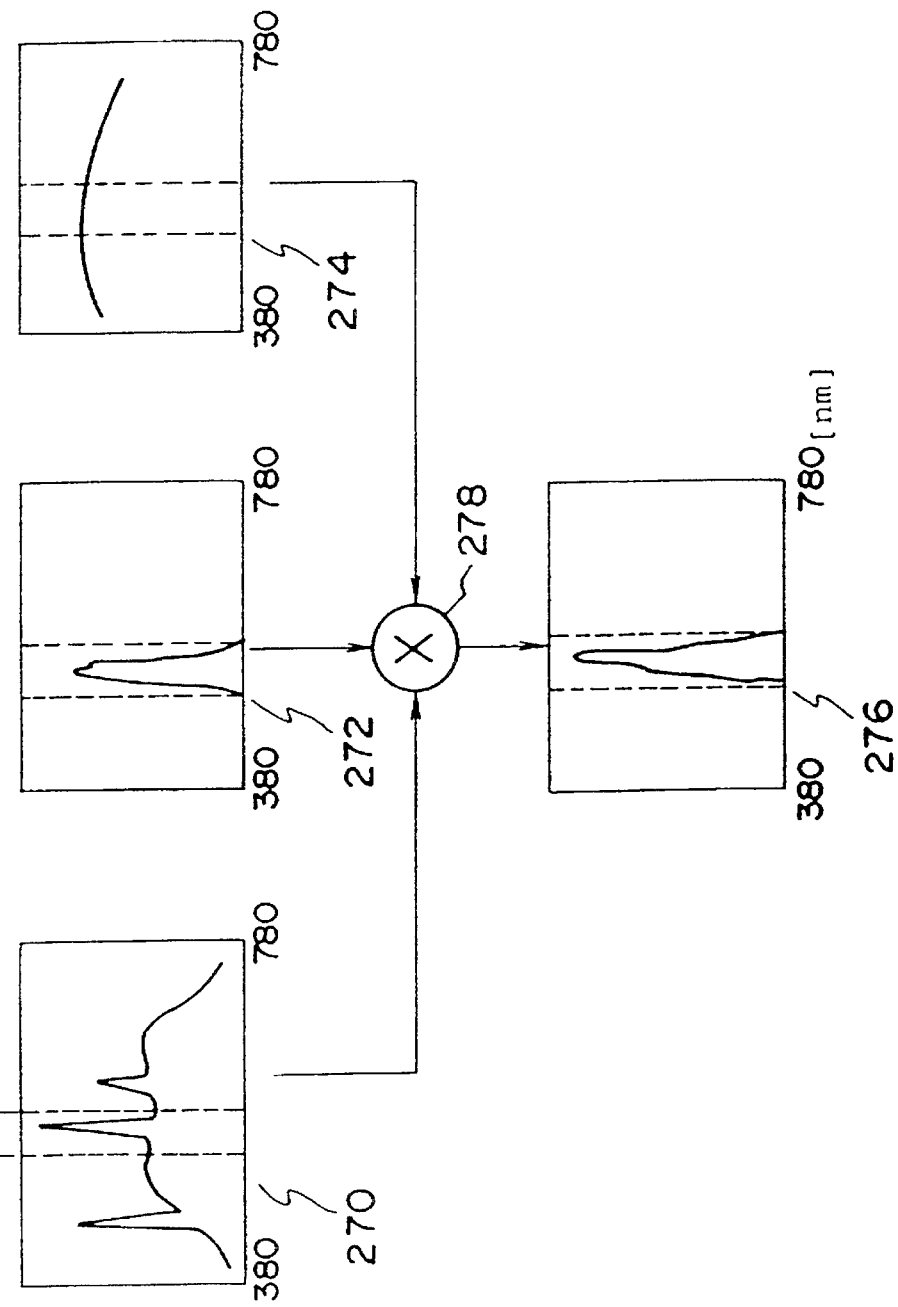
FIG. 13 is an image diagram illustrating the process of determining an overall spectral characteristic of the scanner optical system from the spectral characteristics of a light source, filters, and a light-detecting element.

When this routine is started, the operation proceeds to Step 312 to determine the overall characteristic for each channel corresponding to the wavelength band of each interference filter 246. Namely, the multispectral image scanner 210 of this embodiment is a self-illuminating type scanner, and is capable of measuring each of the spectral distribution 270 of the light sources 222, the spectral transmittance characteristic 272 of the interference filter 246, and the spectral sensitivity characteristic 274 of the CCD sensor 230, as shown in FIG. 13. An overall characteristic 276 is determined for each channel by synthesizing the spectral distribution 270, the spectral transmittance characteristic 272, and the spectral sensitivity characteristic 274 through synthesizing calculation processing 278.

In an ensuing Step 314, the central wavelength $\lambda_0$ for each channel is determined through calculation in which the primary moment S, which will be described later, is reduced to a minimum. Then, the central wavelength $\lambda_0$ determined in Step 316 is stored in the data storage unit 262 by being made to correspond to each channel. The above-described processing is performed with respect to all the channels (Step 318), and this routine ends.

Figure 17:
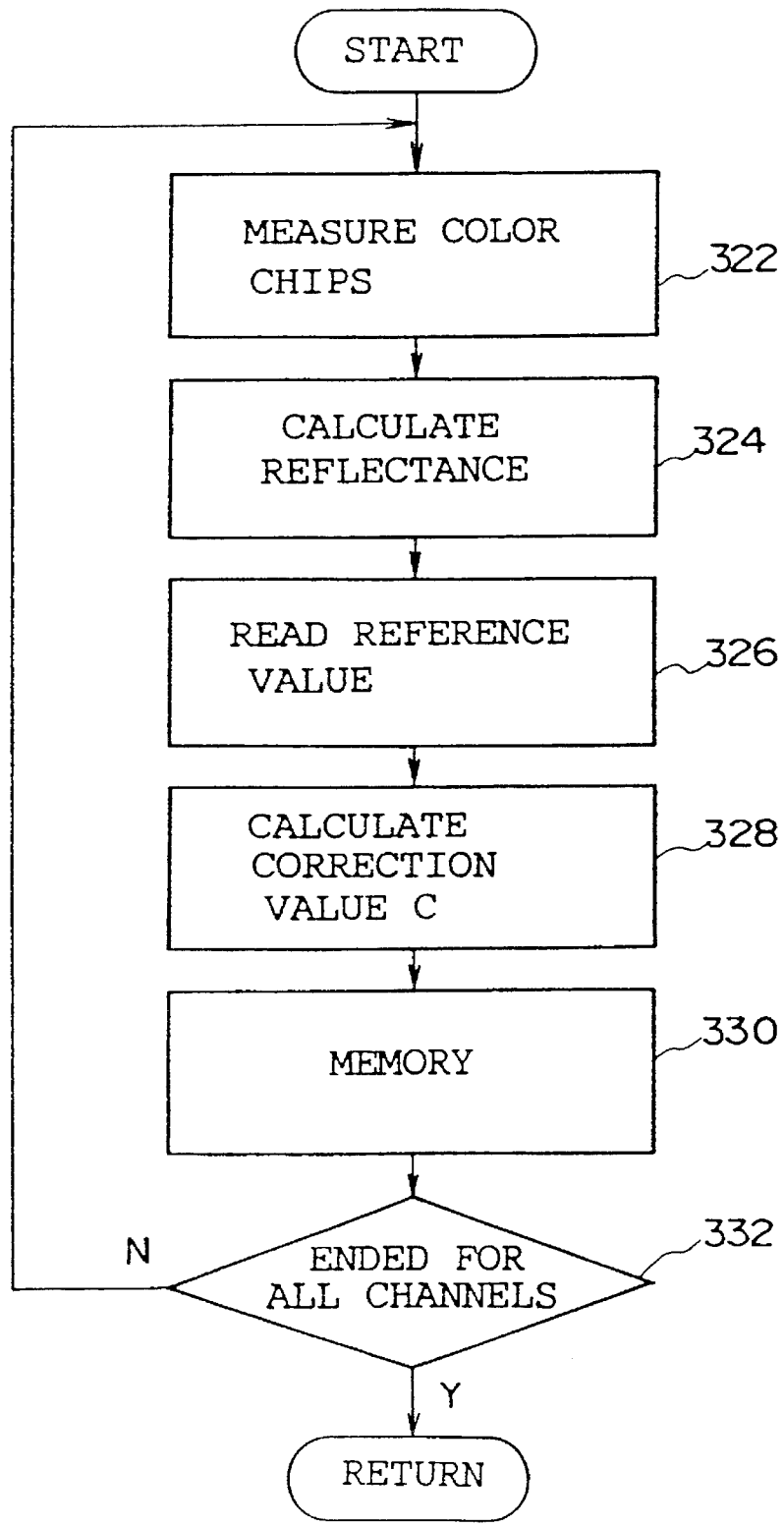
FIG. 17 is a flowchart illustrating a routine for calculating the correction value in accordance with this embodiment.

Since the wavelength band (the band width of the so-called band-pass filter) of the transmitted light in each channel is not very wide, the central wavelength is obtained as the position of the center of gravity corrected with respect to the unsmooth distribution, by calculation for minimizing the primary moment S of the profile of the overall characteristic 276 on the basis of Formula (13) below. That is, $\lambda_0$ for minimizing the primary moment S becomes the wavelength at the position of the center of gravity, and this can be set as the central wavelength.

$$S = \frac{\int_0^\infty (\lambda - \lambda_0) \cdot f(\lambda) d\lambda}{\int_0^\infty f(\lambda) d\lambda} \quad (13)$$

where, $f(\lambda)$: magnitude of the amplitude of the overall characteristic profile of each channel with respect to the wavelength $\lambda$ Referring now to FIG. 17, a detailed description will be given of the calculation of the correction value C in Step 304.

When this routine is practiced, the operation proceeds to Step 322 to measure a plurality of color chips 244 incorporated in the main body serving as standards. In Step 324, the spectral reflectance r is determined for each channel and for each element of the CCD sensor 230. The spectral reflectance r in this case can be determined from the following Formula (14):

$$r = (n_c/n_w) \cdot 100 \ (\%) \quad (14)$$

where, $n_c$: output of the CCD sensor 230 when the color chip 244 is measured $n_w$: output of the CCD sensor 230 when the standard luminous white paper 240 is measured In an ensuing Step 326, a spectral reflectance $r_o$ serving as a reference for the color chip 244 measured in advance by a spectrometer used as a reference is read from the data storage unit 262. The operation then proceeds to Step 328 to determine the correction value C by comparing the reflectances r and $r_o$ of the same color chip, as will be described later. The correction value C thus determined is stored in the data storage unit 262 in Step 330. The above-described processing is performed for each channel, and after the correction value C is determined for all the channels (Step 332), this routine ends.

The aforementioned correction value C can be obtained by determining a coefficient which is obtained by statistical processing, such as by a method in which the spectral reflectance obtained by the spectrophotometer used as a reference for the wavelength band corresponding to the central wavelength determined in Step 302 above is compared with the spectral reflectance of the color chip obtained by the multispectral image scanner 210 of this embodiment, and a regression coefficient is obtained by performing linear regression. In the case where the method based on linear regression is used, the regression line and the regression coefficient can be expressed by the following Formulae (15) and (16), respectively:

$$y = \frac{S_{xy}}{S_{xx}} \cdot (x - \bar{x}) + \bar{y} \quad (15)$$

$$\hat{a} = \frac{S_{xy}}{S_{xx}} \quad (= C) \quad (16)$$

where, x: spectral reflectance r $y$: reference spectral reflectance $r_o$
$\bar{x} = (1/n)\Sigma xi$: mean
$\bar{y} = (1/n)\Sigma yi$: mean
$S_{xx} = (1/n)\Sigma(xi - \bar{x})^2$: variance
$S_{xy} = (1/n)\Sigma(xi - \bar{x})(yi - \bar{y})$: covariance The correction value C obtained by the above-described procedure can be used for measuring other samples repeatedly in a case where the change over time of the optical system of the apparatus is small. In that case, the procedure for obtaining the correction value C can be omitted.

Figure 18:
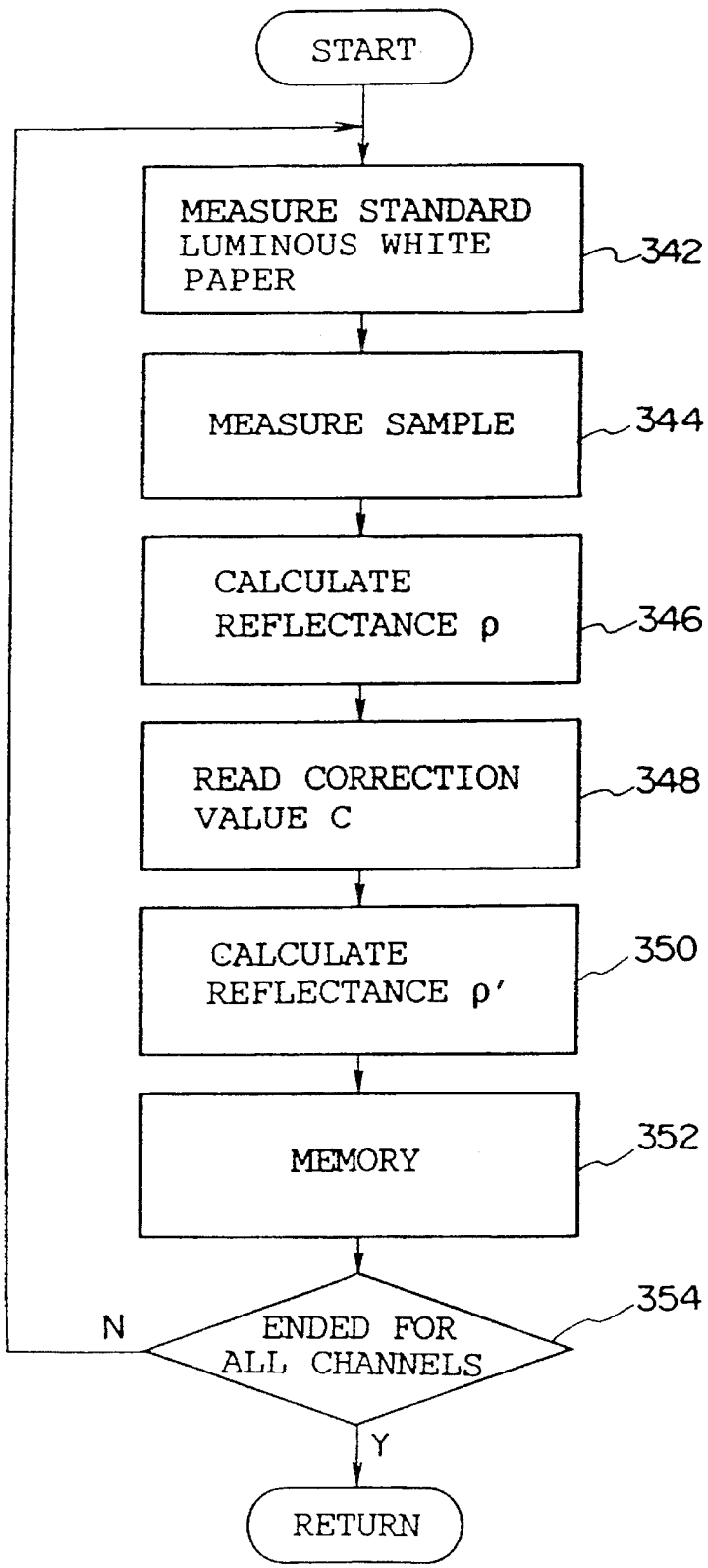
FIG. 18 is a flowchart illustrating a routine for measuring a sample in accordance with this embodiment.

Referring now to FIG. 18, a detailed description will be given of the calculation of the spectral reflectance of the sample 218 in Step 306.

First, in Step 342, the standard luminous white paper 240 is measured by the scanner optical system 220. In an ensuing Step 344, the quantity of light reflected from the sample 218 is measured. In an ensuing Step 346, the spectral reflectance ρ is determined for each channel on the basis of the measured values of the standard luminous white paper 240 and the sample 218. The spectral reflectance ρ in this case can be determined by the following Formula (17) in the same way as Formula (14) above:

$$\rho = (n_s/n_w) \cdot 100 \ (\%) \qquad (17)$$

where, $n_s$: output of the CCD sensor 230 when the sample 218 is measured $n_w$: output of the CCD sensor 230 when the standard luminous white paper 240 is measured Accordingly, the light reflected by the sample 218 is fetched as an output which is proportional to the quantity of light detected by the CCD sensor 230. This value is normalized by an output value obtained by measuring the standard luminous white paper 240, and is transmitted from the communication control unit 258 to the calculating and processing unit 260 as the spectral reflectance ρ corresponding to a gradient.

In an ensuing Step 348, a calibrated spectral reflectance ρ' is determined on the basis of Formula (18) below by using the correction value C stored in Step 304 above. In Step 352, this value is stored in the data storage unit 262 as the spectral reflectance of the pixel by being made to correspond to the central wavelength. The above-described processing is performed for each channel, and after the sample 218 is measured for all the channels (Step 354), this routine ends.

$$\rho' = \rho \cdot C \qquad (18)$$

Figure 14:
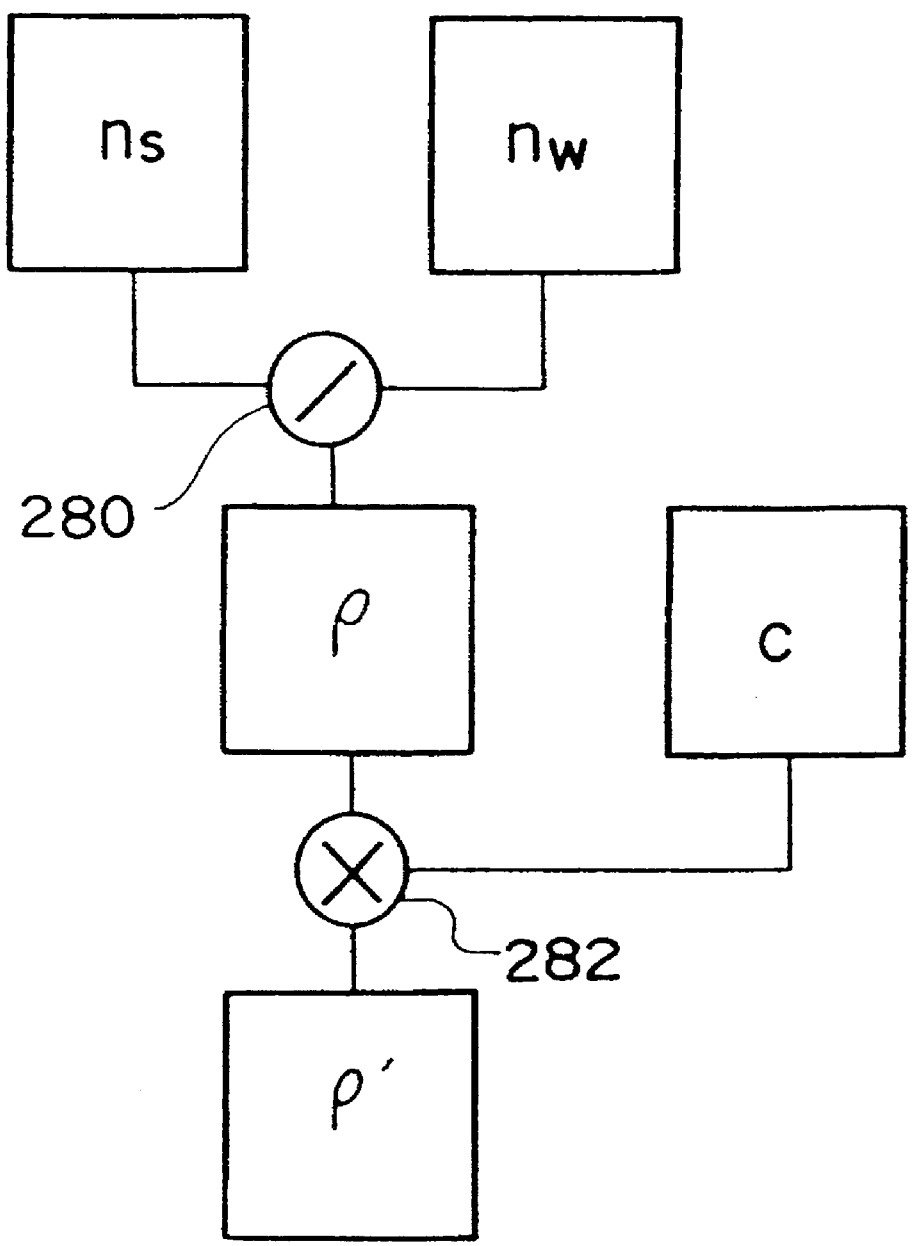
FIG. 14 is an image diagram illustrating the process of determining the spectral reflectance on the basis of measurement values of the standard luminous white paper and correction values.

Accordingly, as shown in FIG. 14, the spectral reflectance ρ is determined through division processing 280 on the basis of the output $n_s$ obtained when the sample 218 was measured and the output $n_w$ obtained when the standard luminous white paper 240 was measured. The calibrated spectral reflectance ρ' calibrated by multiplication processing 282 can be obtained on the basis of this spectral reflectance ρ and the stored correction value C.

Figure 19:
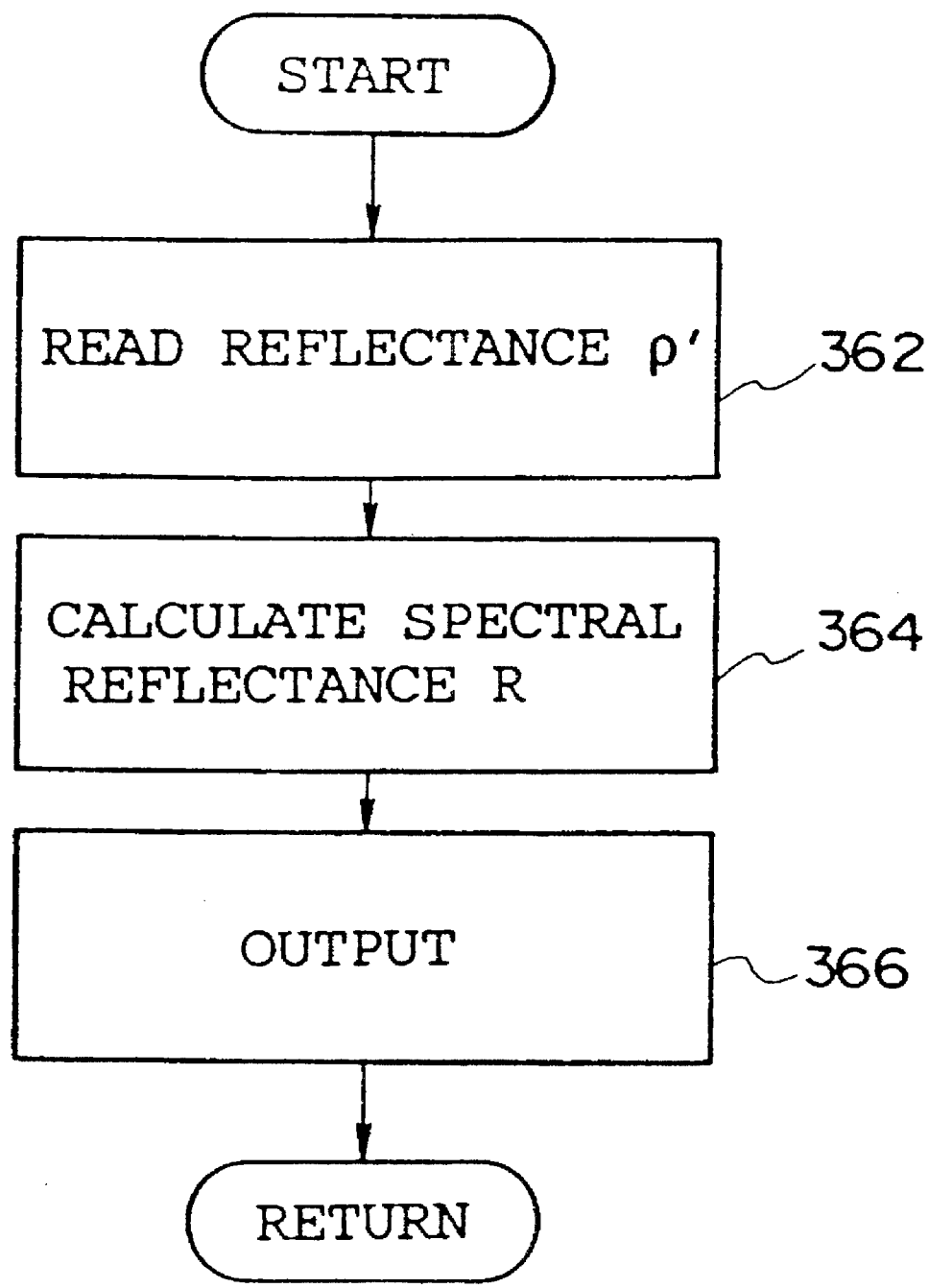
FIG. 19 is a flowchart illustrating a routine for calculating a spectral reflectance in accordance with this embodiment.

Referring now to FIG. 19, a detailed description will be given of Step 308.

Figure 12:
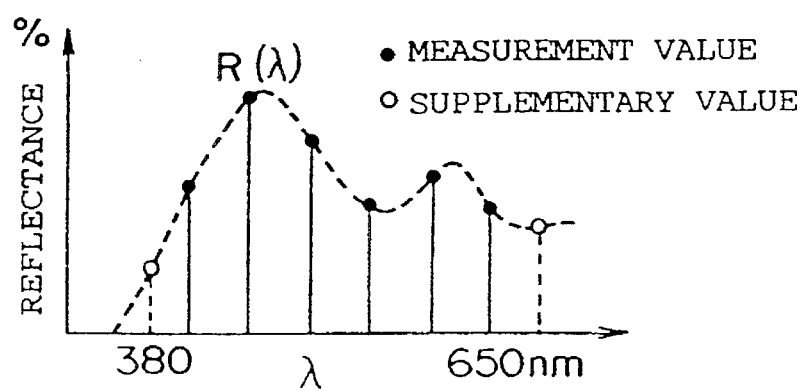
FIG. 12 is an image diagram illustrating the process of estimating the spectral reflectance in accordance with this embodiment.

First, in Step 362, the spectral reflectance ρ' stored in the data storage unit 262 by being made to correspond to the central wavelength of each channel is read. In an ensuing Step 364, a determination is made of spectral reflectances R(λ) in which spectral reflectances at supplementary points are added to the discrete spectral reflectances for each channel on the basis of experiential rules with respect to wavelength bands (in this embodiment, 380 nm and 750 nm) located on the outer sides of the wavelength region of the channel at long and short wavelength ends thereof in the calculating processing unit 260 (as shown in FIG. 12). These experiential rules are based on the following rules (a), (b), (c), and (d):

(a) $R(\lambda)=0$ ($\lambda<350$ nm)

(b) $R(380)=\rho'_1/2$ ($\lambda=400$ nm)

(c) $R(\lambda)=\rho'_i$ ($\lambda_1 \leq \lambda_i < \lambda_n$)

(d) $R(\lambda)=\rho'_n$ ($\lambda>650$ nm)

where, i=1, 2, ..., n (n is the total number of channels)

λ: wavelength $\rho'_i$: spectral reflectance ρ' in the case of a channel i $\lambda_i$: central wavelength of the channel i With respect to discrete spectral reflectances R(λ) including the added supplementary points, interpolation using algebraic polynomials of higher degree, such as cubic spline interpolation and Lagrange's interpolation, is performed so as to obtain a continuous spectral reflectance characteristic. The spectral reflectances obtained, together with the central wavelength, are stored in the data storage unit 262, and are outputted from the interface unit 264 to the output units such as the CRT and the printer (Step 366). The processing for determining the aforementioned spectral reflectances is carried out repeatedly for each pixel, and spectral reflectances of the pixels of the overall screen are finally obtained.

Thus, in this embodiment, the spectral characteristic is improved by increasing the number of channels, and since the calibration and correction of the spectral distribution are conducted independently for each channel, the overall spectral characteristic of the scanner optical system need not be a smooth characteristic. Moreover, the spectral reflectances can be obtained with simple calculation processing.

In the scanner optical system of a colorimeter using a conventional scanner, it is possible to colorimetrically measure the RGB color specification values of the sample by conducting three-component separation and colorimetry by using RGB filters and the like. However, since spectral reflectances cannot be measured, it is impossible to measure the tristimulus values of the XYZ colorimetric system which is a standard colorimetric system. Accordingly, this conventional method cannot be applied to an arbitrary light source tinged with a light-source color.

In this embodiment, channels covering the wavelength bands of the visible light are formed by a plurality of (nine) interference filters 246 (see FIG. 9). As a result, it is possible to obtain the tristimulus values of the XYZ colorimetric system which is the standard colorimetric system, and this embodiment enables an arbitrary light source to be applied to a light source for colorimetrically measuring irrespective of the spectral distribution of the light source.

In this embodiment, by simply disposing or placing the standard color chips on the sample base, it is possible to automatically measure the spectral reflectances of the color chips serving as standards, and correction values can be easily obtained by the measured values and the reference values.

Furthermore, in this embodiment, by simply placing the sample on the sample base, the reference values are automatically measured, and the spectral reflectances are automatically measured. At this time, it is possible to measure the spectral reflectance of a infinitesimal area by performing the above-described processing for each element of the CCD of the CCD sensor 230. At the same time, as the scanner optical system is moved to effect scanning, the sample surface, e.g., an A3-size surface, can be measured by using all the CCD elements of the CCD sensor 230 as pixels for the sample surface of that size. Hence, it is possible to determine spectral reflectances of the sample surface and determine spectral reflectances of infinitesimal areas and the surface.

Although in the above embodiments a description has been given of an example in which transmission-type filters are used, the present invention is not limited to the same, and reflection-type mirrors such as dichroic mirrors may be used. In this case, it suffices if spectral reflectances are used instead of spectral transmittances.

Although a description has been given of an example in which spectral reflectances are determined for a plurality of wavelength bands which do not overlap, an arrangement may be provided such that spectral reflectances are determined for a plurality of wavelengths or a plurality of wavelength bands which overlap. It should be noted that, in order to spectrally separate the light for each wavelength or wavelength band, it is possible to use optical elements such as a prism and a diffraction grating instead of the filters.

Referring to the drawings, a detailed description will be given of an embodiment of a three-dimensional automatic gonio-spectrophotometer for measuring spectral reflectance factors in the rendering apparatus of the above-described embodiment.

Figure 20:
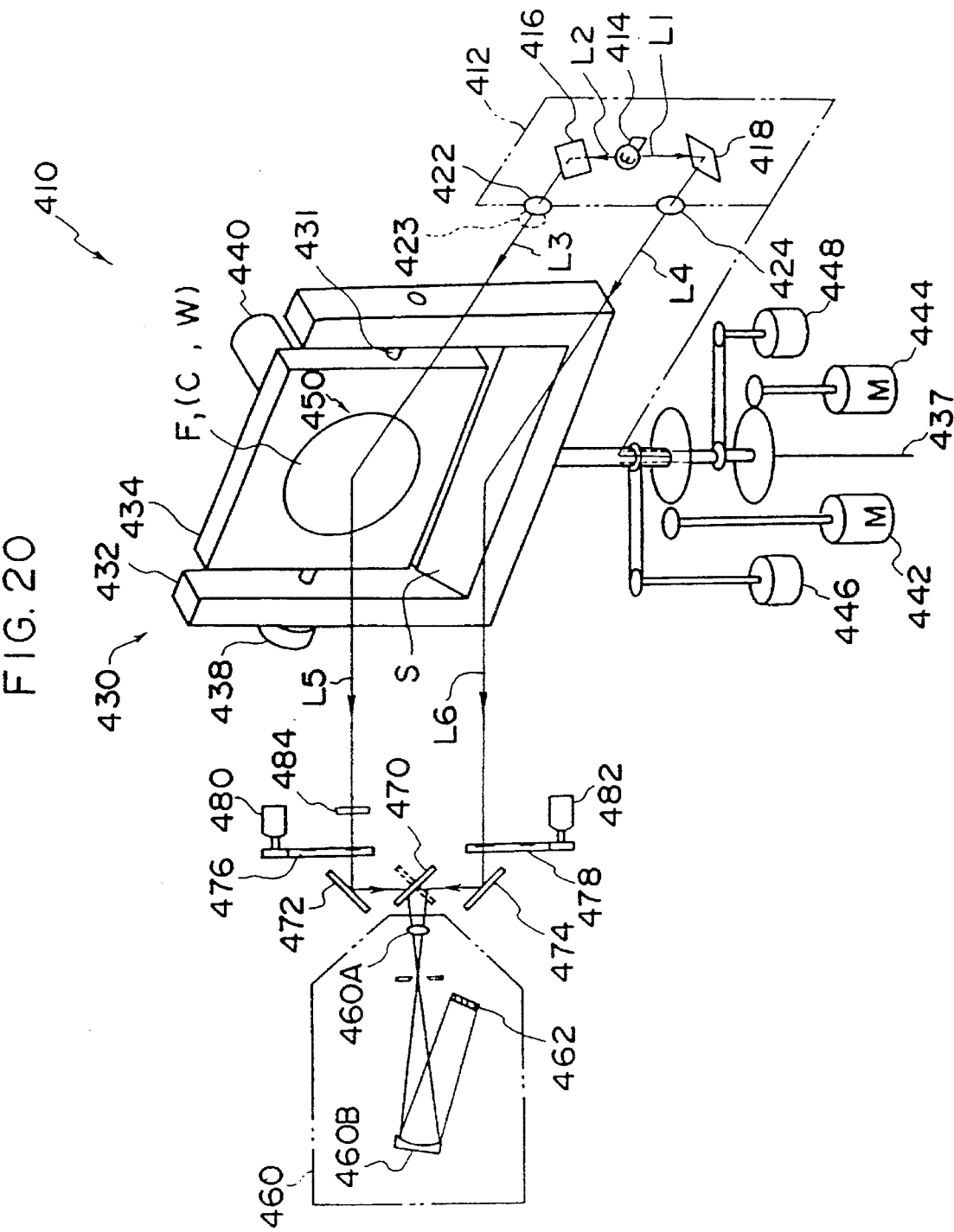
FIG. 20 is a perspective view illustrating a schematic configuration of an embodiment of a three-dimensional automatic gonio-spectrophotometer in accordance with the present invention.
Figure 21:
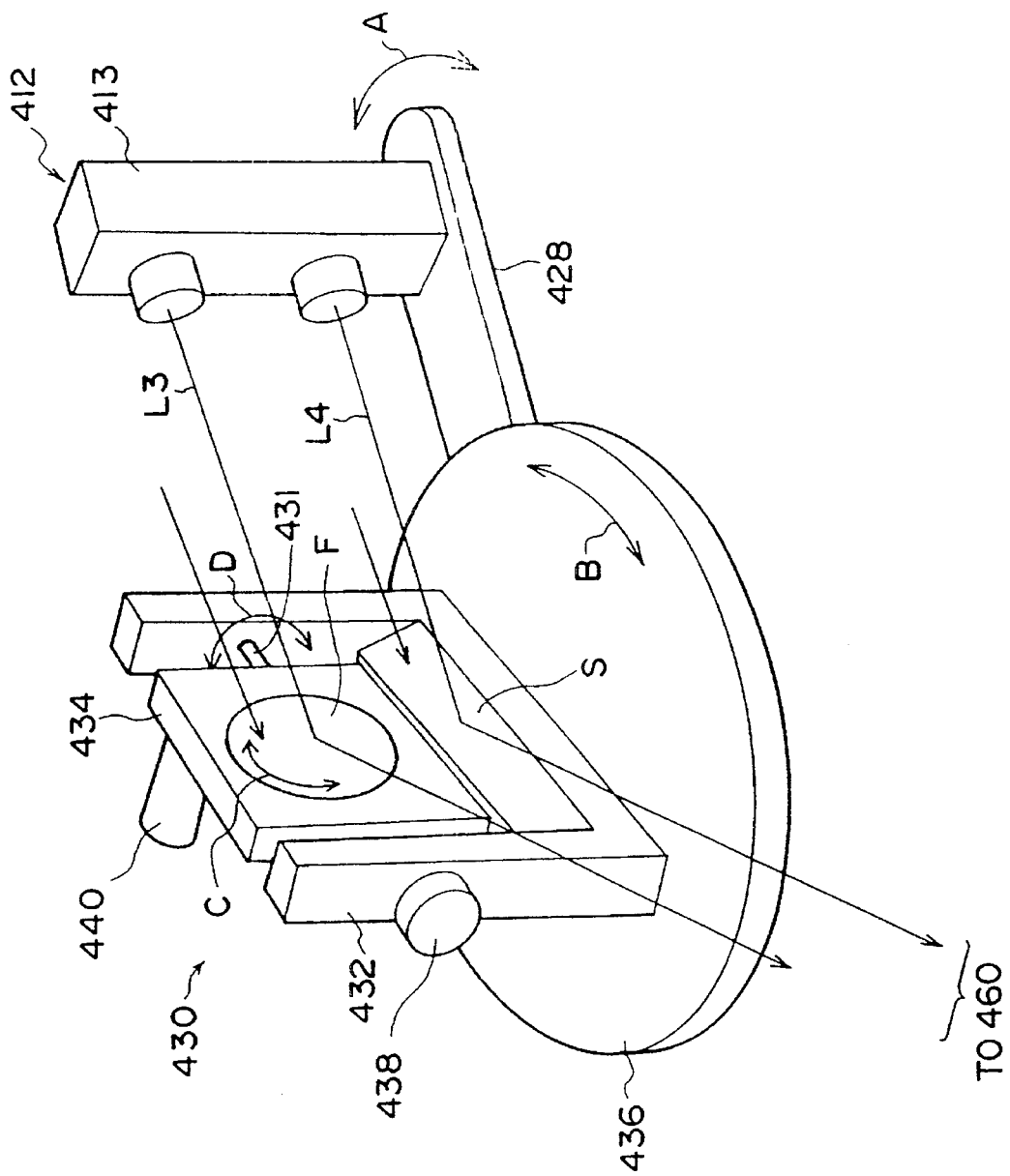
FIG. 21 is a perspective view illustrating a light source unit and a sample rotating unit in accordance with this embodiment.

As shown in FIG. 20, a three-dimensional gonio-spectrophotometer 410 of this embodiment has a light source unit 412, and this light source unit 412 has a lamp 414 in a lamphouse 413 (see FIG. 21). This lamp 414 lights up when the power supply is turned on. Lenses 422 and 424 for converting the incident light into a parallel beam of light are disposed above and below the lamp 414, respectively. The light emitted from the lamp 414 is reflected toward the lenses 422 and 424 by mirrors 416 and 418 in such a manner that optical axes L3 and L4 of the light made emergent from the lenses 422 and 424 become parallel in an identical plane including a vertical axis. A filter holder 423 is disposed on the emergent side of the lens 422, and a filter can be inserted such that the quantities of light made emergent from the respective lenses 422 and 424 and the wavelength distributions thereof coincide with each other.

The lamphouse 413 is fixed to one end of an elongated lamp base 428 (see FIG. 21), and the other end of the lamp base 428 is axially secured to a vertical shaft 437.

A sample rotating unit 430 is disposed on the emergent side of the light source unit 412. The sample rotating unit 30 has a sample base 436 (see FIG. 21) which is rotatable about the vertical shaft 437. A U-shaped fixed member 432 is fixed to the upper surface of the sample base 436 such that its upper side is open. The reference white plate S for comparison of the reflectance distribution between the same and the sample F is mounted on an upper surface of a base portion of the U-shaped fixed member 432 by being inclined at a predetermined angle. Thus, since the reference white plate is inclined, it is possible to avoid the sheen in the direction of regular reflection. It should be noted that if this angle is too small (several degrees), it is impossible to avoid the effect of the sheen, while if it is too large (several tens of degrees), the illuminance of the reference white plate declines, possibly resulting in measurement error. Therefore, this angle needs to be set within an appropriate range of angle (e.g., 5° to 30°) in accordance with the optical system including the reference white plate. Furthermore, this angle is preferably set to a minimum angle at which the sheen can be avoided.

A flap plate 434 having a shaft 431 is disposed in an intermediate portion of the fixed member 432 in such a manner as to be rotatable about its shaft perpendicular to the vertical shaft 437 (in the directions of double-headed arrow D in FIG. 21). A portion of this flap plate 434 in the vicinity of a center thereof is set as a measurement area 450, and the sample F attached to the flap plate 434 is flapped as a motor 438 rotates. This motor 438 is constituted by a stepping motor, is connected to a controller 490 (see FIG. 22), and rotates through a predetermined angle when a predetermined pulse signal is inputted thereto. It should be noted that a working standard white plate C and a white-coated plate W can be disposed in the measurement area 450. In addition, a motor 440 is attached to the flap plate 434. This motor 440 is constituted by a stepping motor, is connected to the controller 490 (see FIG. 22), and rotates through a predetermined angle when a predetermined pulse signal is inputted thereto. Accordingly, as the motor 440 rotates, the sample F and the like attached to the flap plate 434 rotate in the same plane, i.e., about a line normal to the sample F (in the directions of double-headed arrow C in FIG. 21).

The sample base 436 is fixed to one side of a so-called rotating stage (not shown), and the other side of this rotating stage is secured to an unillustrated apparatus main body of the three-dimensional gonio-spectrophotometer 410. Similarly, the lamp base 428 is also secured to a moving side of the rotating stage secured to the main body. The rotational axes of these members are formed to be identical with that of the vertical shaft 37.

A motor 442 for rotating the sample base 436, i.e., for rotating the sample rotating unit 430 about the vertical shaft 437 (in the directions of double-headed arrow B in FIG. 21), and a motor 444 for rotating the lamp base 428 about the vertical shaft 437, i.e., for rotating the light source unit 412 (in the directions of double-headed arrow A in FIG. 21), are disposed below the sample base 436. The angles at which the sample base 436 and the lamp base 428 are rotated by these motors 442 and 444 are detected by encoders 446 and 448, and the encoders 446 and 448 output electrical signals corresponding to the rotational angles, respectively. These encoders 446 and 448 are connected to the controller 490 (see FIG. 22).

Mirrors 472 and 474 are disposed on the opposite side of the sample rotating unit 430 in accordance with the measurement area 450 of the sample rotating unit 430 and the reference white plate S, respectively. The optical paths L5 and L6 leading to these mirrors 472 and 474 are so adjusted as to be substantially parallel with each other. The mirror 472 reflects the light which has passed the optical path L5 in such a manner that the light reaches a sector unit 470. Similarly, the mirror 474 reflects the light which has passed the optical path L6 in such a manner that the light also reaches the sector unit 470.

The sector unit 470 for selecting the light to be radiated to a spectroscope 460 is disposed on the emergent side of the mirrors 472 and 474. Namely, the sector unit 470 is rotated (see FIG. 22) by an unillustrated driving means connected to the controller 490, and radiates the light diffusively reflected from an object to be measured (e.g., the sample F) disposed on the sample rotating unit 430 and from the reference white plate S alternately to the spectroscope 460.

The spectroscope 460 is provided with a photodiode array 462 having a plurality of photoelectric conversion devices. The light made incident upon the spectroscope 460 is radiated to the photodiode array 462 via a lens 460A and a concave diffraction grating 460B. Accordingly, the light guided by the spectroscope 460 is dispersed by the diffraction grating for each wavelength or wavelength band, and is subjected to photoelectric conversion by the devices corresponding to the respective wavelengths or wavelength bands of the photodiode array 462. This photodiode array 462 is connected to the controller 490 (see FIG. 22).

Light-attenuating devices such as ND filters disposed in a light-attenuating plate unit 476 are arranged on the optical path L5 in such a manner as to be capable of being inserted into the optical path L5. As a motor 480 rotates, the light-attenuating rate can be altered. Similarly, light-attenuating devices such as ND filters disposed in a light-attenuating plate unit 478 are so arranged as to be insertable into the optical path L6 as well. As a motor 482 rotates, the light-attenuating rate can be altered. In addition, a filter holder 484 is disposed in the optical path L5 to allow filters or the like to be constantly provided therein.

Figure 22:
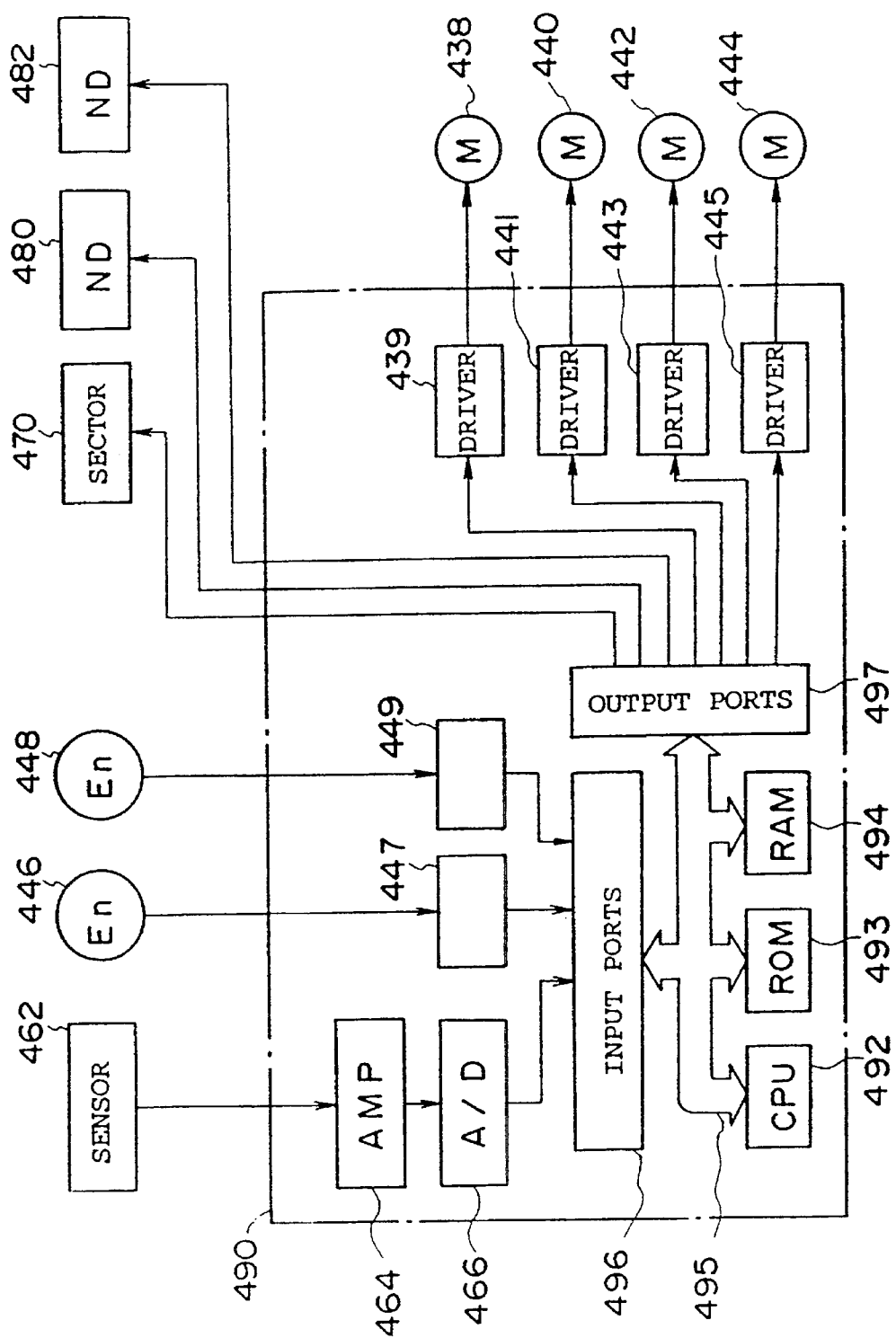
FIG. 22 is a block diagram illustrating a configuration of a controller in accordance with this embodiment.

As shown in FIG. 22, the controller 490 is comprised of a microcomputer in which a CPU 492, a ROM 493, a RAM 494, input ports 496, and output ports 497 are connected to each other via buses 495, and are capable of mutually transmitting or receiving data and commands.

An AD converter 466 connected to an amplifier (AMP) 464 of a predetermined amplification factor for converting analog signals into digital signals is connected to the input ports 496. Also connected to the input ports 496 are detection circuits 447 and 449 for converting detection signals (angles) of the encoder 446 for detecting the angle of the sample base 436 and the encoder 448 for detecting the angle of the lamp base 428 into digital signals.

Connected to the output ports 497 are a driving means 421, the sector unit 470, a motor 480, and a motor 482, as well as the motors 438, 440, 442, and 444 via drivers 439, 441, 443, and 445.

A display unit (not shown) for notifying measurement results and measurement procedures and status to the operator is connected to the controller 490. Also, an output device by which measurement results and the like are outputted is also connected to the controller 490.

Hereafter, a description will be given of the operation of this embodiment together with measurement procedures.

Figure 23:
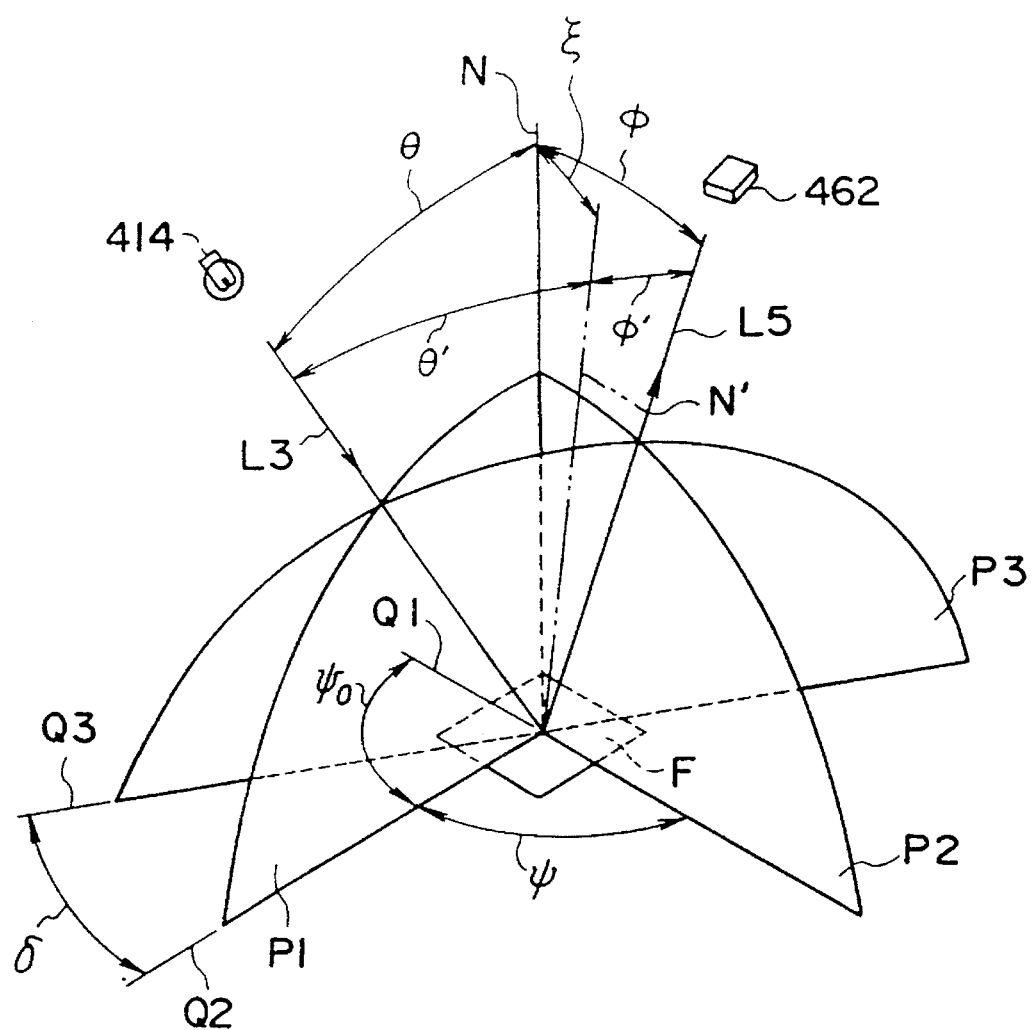
FIG. 23 is a perspective view illustrating the angular relationship of the light with respect to the sample.

First, prior to a description of measurement of the spectral reflectance factor distribution R(λ), with reference to FIG. 23 a description will be given of the angle transformation for angle-changing control of the three-dimensional gonio-spectrophotometer 410 constructed as described above.

It is assumed that, in a case where the sample F is fixed and the light source 414 and the photo diode array 462 are moved relative to the sample F by a rectangular coordinate system, an angle formed by the normal line N of the sample F and the optical axis L3 of the incident light is an incident angle θ, that an angle formed by the normal line N and the optical path L5 of the light reflected toward the photodiode array 462 is a light-detecting angle φ, that a plane including the normal line N and the optical axis L3 of the incident light is an incident plane P1, that a plane including the normal line N and the optical path L5 of the reflected light is a light-detecting plane P2, that an angle formed by the incident plane P1 and the light-detecting plane P2 is an azimuth angle Ψ, and that an angle formed by a reference azimuth line Q1 serving as a positional reference for the rotation of the sample F and a line Q2 of intersection between the sample surface and the incident plane P1 is a sample azimuth angle $\Psi_o$. In the three-dimensional measurement, it is possible to perform three-dimensional measurement by changing these angles (θ, φ, Ψ, $\Psi_o$)

In the three-dimensional gonio-spectrophotometer 410 of this embodiment, the optical axis L3 of the incident light and the optical path L5 of the emergent light with respect to the sample F are formed in an identical plane (see FIG. 21). Accordingly, it suffices if the sample F, the light source 414, and the photodiode array 462 are moved to form such a plane that a plane P3 whose luminous intensity is to be measured includes the optical axis L3 of the incident light and the optical path L5 of the reflected light. Namely, the angle formed by a normal line N' of the sample F at a time when the luminous-intensity measurement plane P3 and the sample F intersect each other on the one hand, and the aforementioned normal line N on the other, becomes a flap angle ξ, and the incident angle and the light-detecting angle respectively become an incident angle θ' and a light-detecting angle φ' based on the normal line N' as a reference. In addition, the angle formed by a line Q3 of intersection between the luminous-intensity measurement plane P3 and the sample surface on the one hand, and the aforementioned line Q2 on the other, becomes an in-plane rotational angle δ. This relation can be expressed as the following Formula (19):

$$G(\theta', \phi', \xi, \delta)=F(\theta, \phi, \Psi, \Psi_o) \quad (19)$$

where,

G(θ', φ', ξ, δ): angular condition in the three-dimensional gonio-spectrophotometer 410 of this embodiment F(θ, φ, Ψ, $\Psi_o$): angular condition when the sample is fixed Accordingly, the angles (θ, φ, Ψ, $\Psi_o$) defined by the rectangular coordinate system with respect to the sample F can be converted to the angles (θ', φ', ξ, δ) which are changeable in the three-dimensional spectrophotometer of this embodiment.

Figure 24:
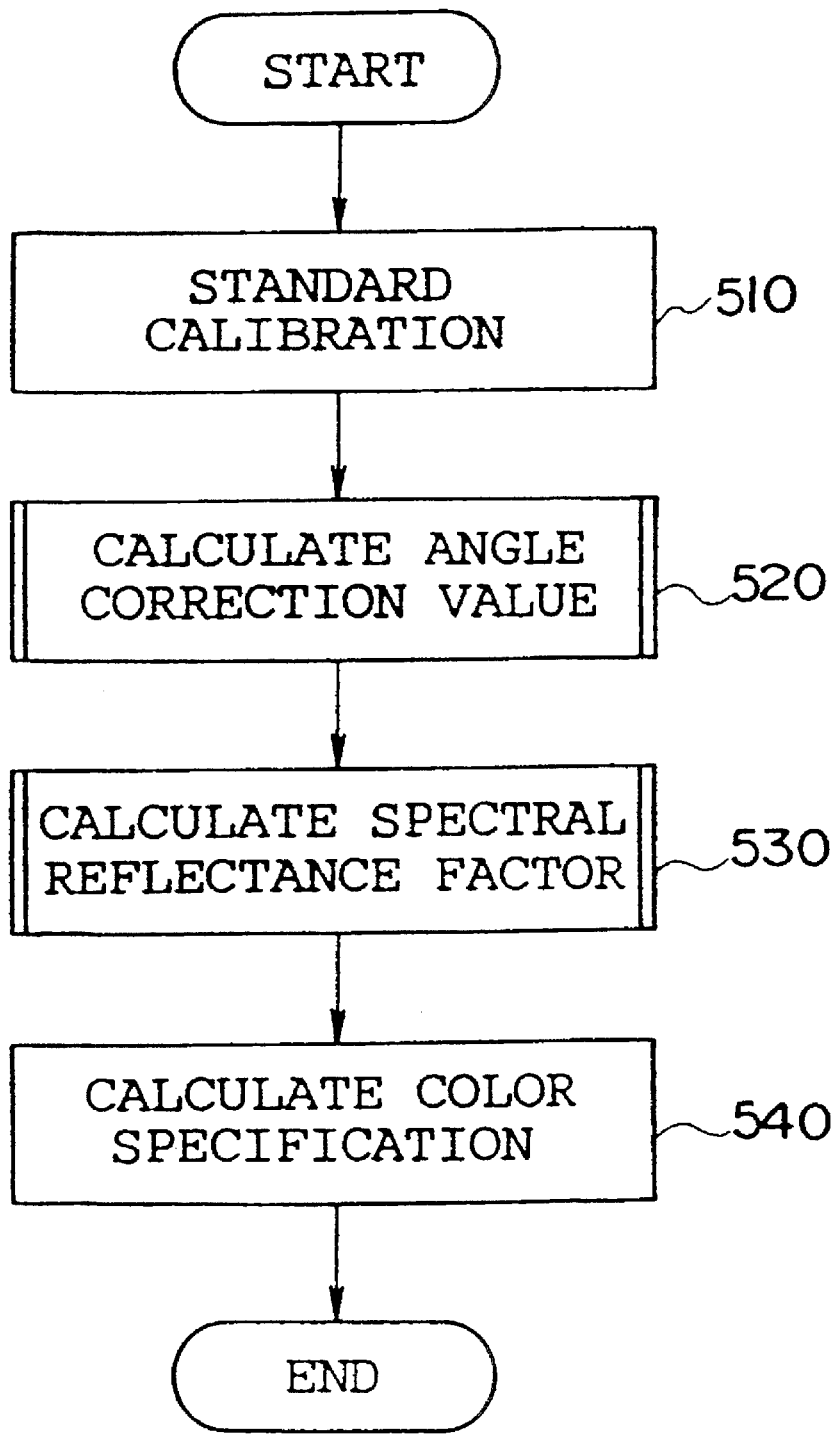
FIG. 24 is a flowchart illustrating the control process by a controller of the three-dimensional gonio-spectrophotometer.

Next, referring to the flowchart shown in FIG. 24, a description will be given of the measurement procedures. When the power supply of the three-dimensional spectrophotometer is turned on, the operation proceeds to Step 510 to effect standard calibration. This standard calibration is effected to calibrate the measurement data of the three-dimensional gonio-spectrophotometer 410 by using the working standard white plate C in such a manner that the spectral reflectance factor Rw(λ) of the working standard white plate C whose values are known will be outputted. As for the angular condition (reference angular condition) at this time, the working standard white plate is set on the sample base, such that the incident angle θ' of the three-dimensional gonio-spectrophotometer 410 is 45°, the light-detecting angle φ' of the three-dimensional gonio-spectrophotometer 410 is 0°, and the flap angle ξ is 0°. As the spectral reflectance factor, a value determined by the aforementioned Formula (a) is outputted. Accordingly, a measured value outputted after completion of this calibration becomes a spectral reflectance factor.

Upon completion of the standard calibration, the operation proceeds to Step 520 to effect the measurement and calculation for an angle correction value K. Namely, as for this angle correction value, the high-luster white-coated plate W is set in the measurement area 450 of the sample rotating unit 430, the light reflected from the white-coated plate W is measured under a plurality of angular conditions equivalent to those when the sample F is measured, and respective angle correction values K are calculated on the basis of Formula (20) below. It should be noted that each angle in this angular condition is one in which the angles of the three-dimensional rectangular coordinate system are converted to the angles of the three-dimensional gonio-spectrophotometer 410 of this embodiment in accordance with Formula (19) above.

$$K(\theta', \phi', \xi, \delta, \lambda)=M(\theta', \phi', \xi, \delta, \lambda)/C(\lambda) \quad (20)$$

where,

K(θ', φ', ξ, δ, λ): angle correction value

M(θ', φ', ξ, δ, λ): measured value of the white-coated plate (spectral reflectance factor)

C(λ): measured value of the white-coated plate (spectral reflectance factor) when the three-dimensional spectrophotometer is set at:
incident angle 45°, light-detecting angle 0°, flap angle 0°, and in-plane rotational angle 0°

θ': incident angle of the three-dimensional spectrophotometer

φ': light-detecting angle of the three-dimensional spectrophotometer

ξ: flap angle

δ: in-plane rotational angle

λ: wavelength

Accordingly, this angle correction value K becomes a correction coefficient for converting the spectral reflectance factor measured under an angular condition different from the standard angular condition persisting at the time of calibration, into a spectral reflectance factor R(λ) measured under the angular condition (illuminance characteristic and light detection characteristic) at a time when the light-detecting angle φ' of the three-dimensional gonio-spectrophotometer 410 is 0°, the flap angle ξ is 0°, and the in-plane rotational angle δ is 0°. Thus, by determining the angle correction values, it is possible to correct a change in the angular distribution of the light reflected owing to the partially reflected flux of light when light-detecting angle is changed.

Figure 25A:
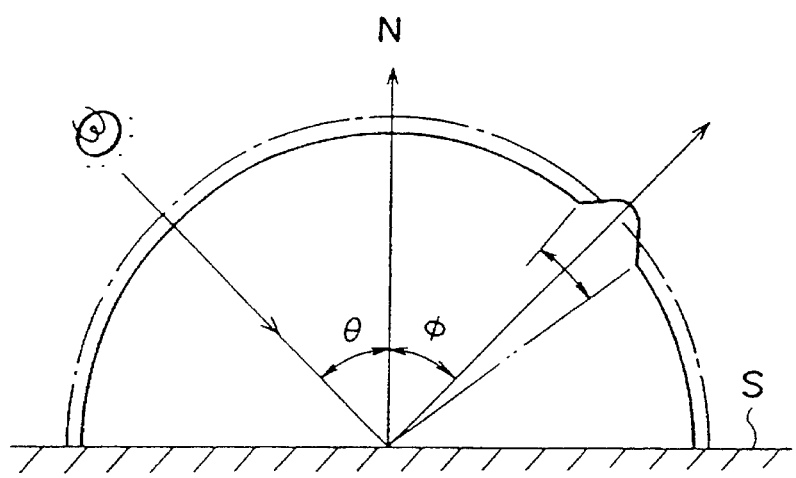
FIG. 25A is a diagram illustrating the state of diffusive reflection of a reference white plate.
Figure 25B:
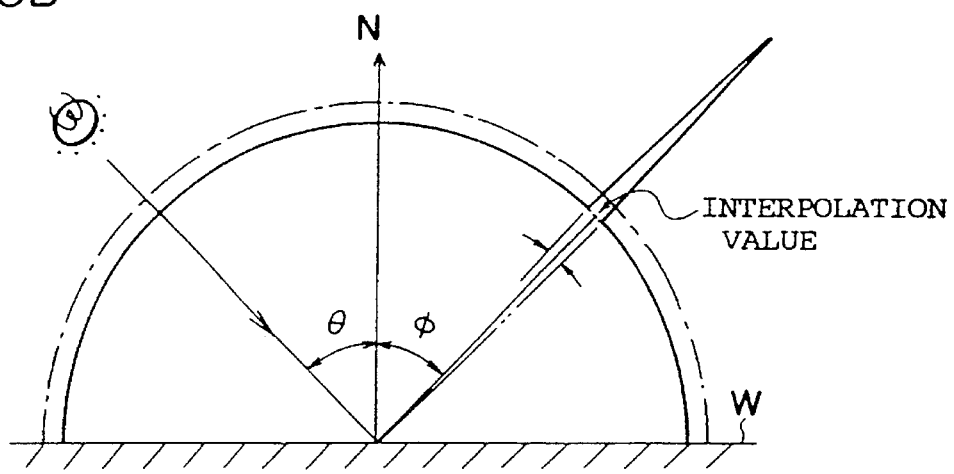
FIG. 25B is a diagram illustrating the state of diffusive reflection of a white-coated plate used in this embodiment.

Here, the reference white plate S is generally used as the white plate for referencing at the time of measurement by the spectrophotometer. This reference white plate S excels in the uniformity in the reflectance distribution, but a regular reflection range where the uniformity of the reflectance distribution is undermined and an angle range where the sheen occurs are large (see FIG. 25A). For this reason, in this embodiment, the white-coated plate W in which the angle range where this uniformity is undermined is smaller than the reference white plate S is used as the white plate for angle correction (see FIG. 25B).

As for the angle correction value in the regular reflection range, i.e., the angle range where the uniform diffusion in the white-coated plate W is undermined (in this embodiment, θ'−7°≦φ'≦θ'+7°), an interpolated value obtained by using the measurement data of the diffusively reflected range (φ'<θ'−7°, φ'>θ'+7°) of the white-coated plate W is used as the angle correction value. As a result, the measurement data is prevented from varying and the resultant spectral reflectance factor from varying due to the strong reflected light in the direction of regular reflection in the angle range tinged with the sheen. Accordingly, it is possible to conduct the measurement of optimum spectral reflectance factor even in an angle range which is not a uniformly diffusive angle range (see the broken line in FIG. 25B). It should be noted that the angle correction value for the regular reflection range may be obtained by interpolating the angle correction value for a diffusive reflection range.

Upon completion of the calculation of the angle correction value, the operation proceeds to Step 530, the sample F, e.g., a fabric, is disposed in the measurement area 450 of the sample rotating unit 430, the sample F is measured, and the spectral reflectance factor R(λ) is determined in accordance with the following Formula (21):

$$R(\theta', \phi', \xi, \delta, \lambda) = D(\theta', \phi', \xi, \delta, \lambda)/K(\theta', \phi', \xi, \delta, \lambda) \quad (21)$$

where,

R(θ', φ', ξ, δ, λ): spectral reflectance factor of the sample F

D(θ', φ', ξ, δ, λ): measured value of the sample

Accordingly, the spectral reflectance factor R(λ) thus measured becomes a reflectance distribution in which the measured value D of the sample is transformed by the angle correction value K into a spectral reflectance factor R(λ) measured under the angular condition (illuminance characteristic and light reception characteristic) at a time when the light-detecting angle φ' of the three-dimensional gonio-spectrophotometer 410 is 0°, the flap angle ξ is 0°, and the in-plane rotational angle δ is 0°.

Figure 26:
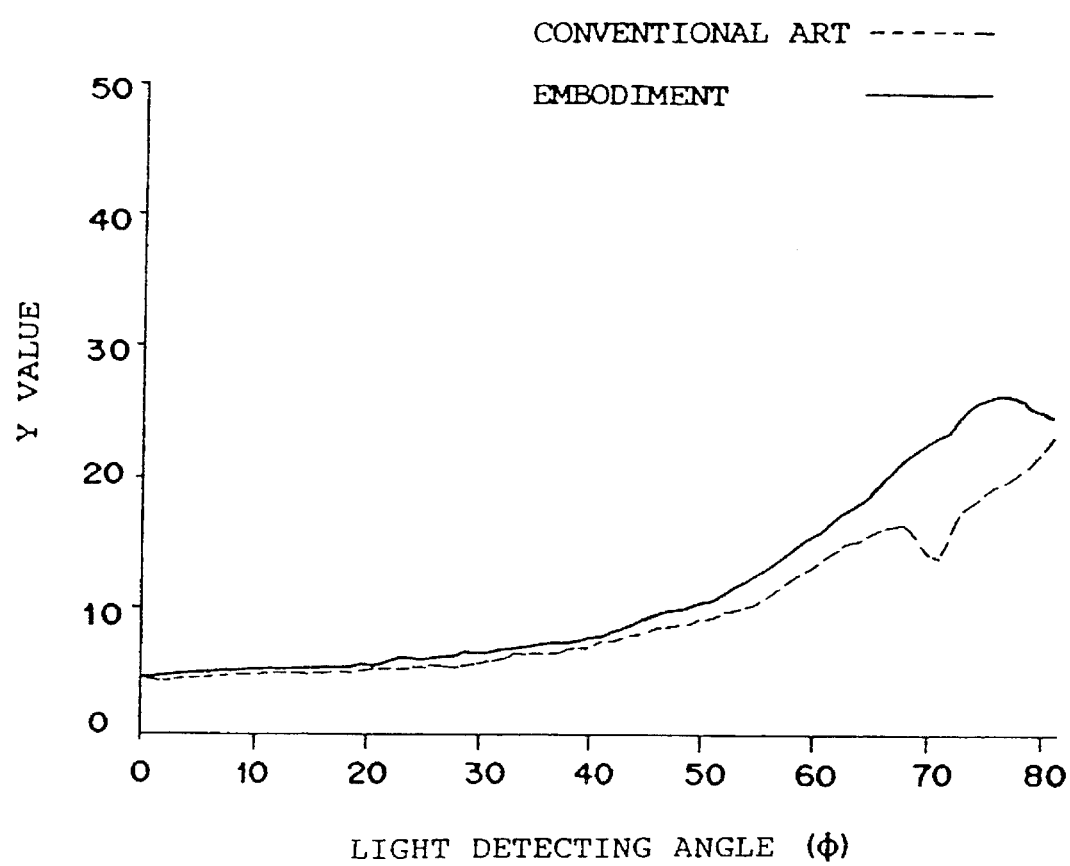
FIG. 26 is a characteristic diagram illustrating the relationship between a light-detecting angle and a Y value (a tristimulus value)

This spectral reflectance factor R(λ) is used in the rendering apparatus described above. After completion of the calculation of the spectral reflectance factor R('), the operation proceeds to Step 540 to determine tristimulus values X, Y and Z in accordance with Formulae (22), (23) and (24) below and perform colorimetric calculation. After completion of this calculation, the values thus obtained may be displayed or outputted.

$$X = \int R(\lambda) \cdot I(\lambda) \cdot \bar{x}(\lambda) d\lambda \quad (22)$$
$$Y = \int R(\lambda) \cdot I(\lambda) \cdot \bar{y}(\lambda) d\lambda \quad (23)$$
$$Z = \int R(\lambda) \cdot I(\lambda) \cdot \bar{z}(\lambda) d\lambda \quad (24)$$

where, $\bar{x}(\lambda)$, $\bar{y}(\lambda)$, and $\bar{z}(\lambda)$: tristimulus values of a spectrum R(λ): spectral reflectance factor I(λ): spectral distribution of the light source The results of measurement of spectral reflectance factor and color specification obtained as described above are shown below. FIG. 26 shows the relationship between the Y value of the tristimulus values and the light-detecting angle φ when the incident angle θ was 70°, the azimuth angle Ψ was 180°, and the azimuth angle $\Psi_o$ of the sample was 0°. At an angle in which the uniform diffusion of the reference white plate is undermined due to the sheen, the reflectance is measured to be lower than its intrinsic value in accordance with a conventional method. Hence, the Y value of the tristimulus values conventionally exhibited a trough in the angle range in the direction of regular reflection. In this embodiment, the white-coated W in which the angle range where the uniform diffusion is undermined is smaller than the reference white plate S is used, and the measured value of the angle range where the sheen occurs (regular reflection range) is corrected by the measured value in the uniformly diffusive angle range. Therefore, the spectral reflectance factor obtained does not vary due to the strong reflected light in the direction of regular reflection, and it is possible to effect the measurement of optimum spectral reflectance factors.

Figure 31:
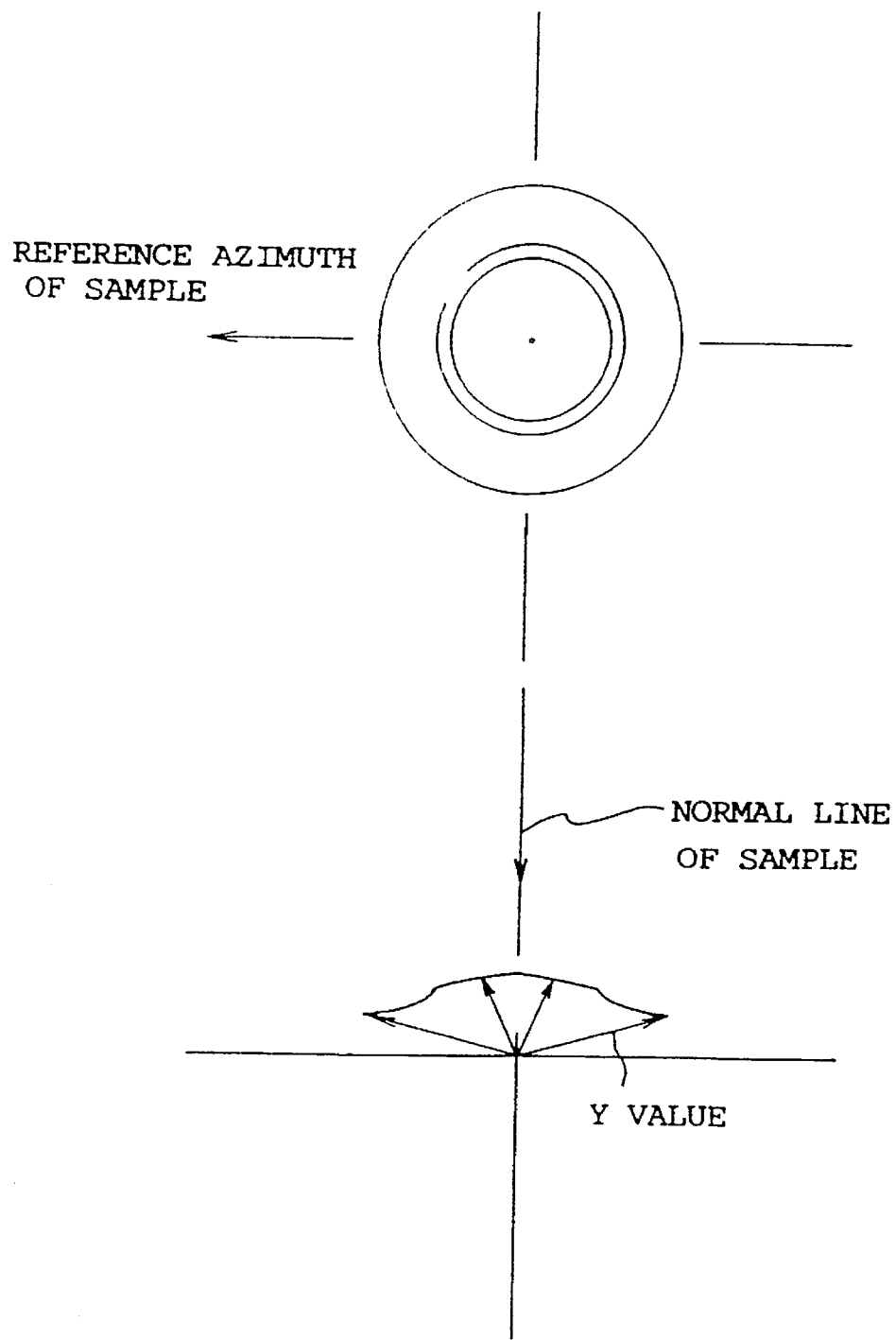
FIG. 31 is a top plan view and a front elevational view of a three-dimensional distribution of the Y value.
Figure 32:
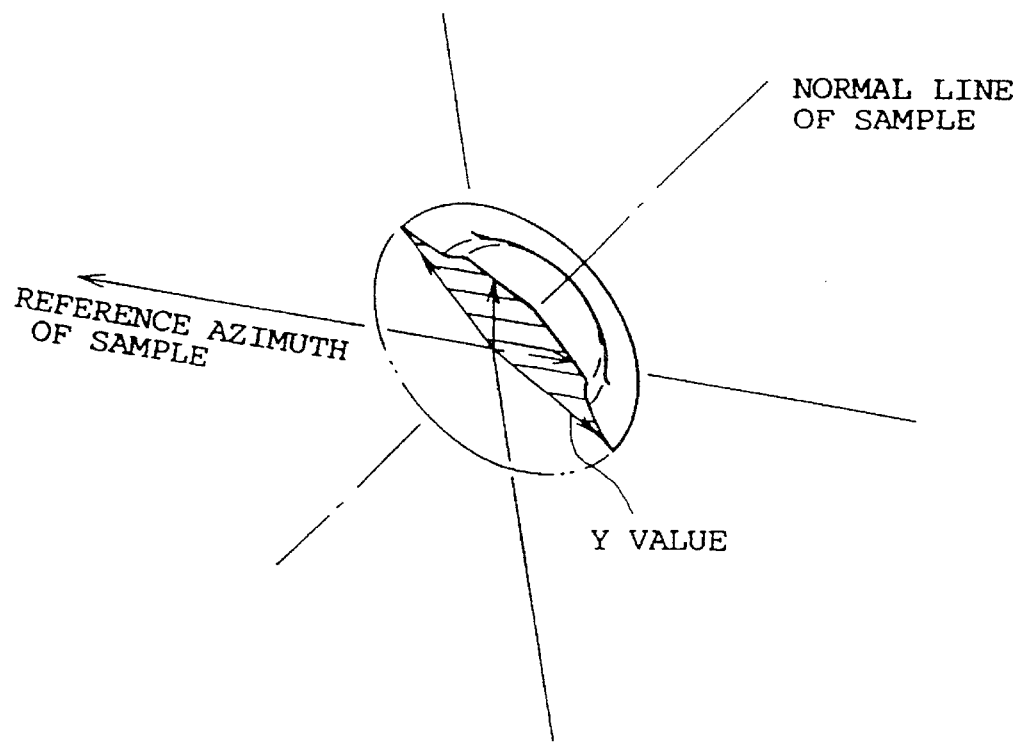
FIG. 32 is a perspective view of FIG. 31.
Figure 33:
FIG. 33 is a front elevational view and a side elevational view of the three-dimensional distribution of the Y value.
Figure 34:
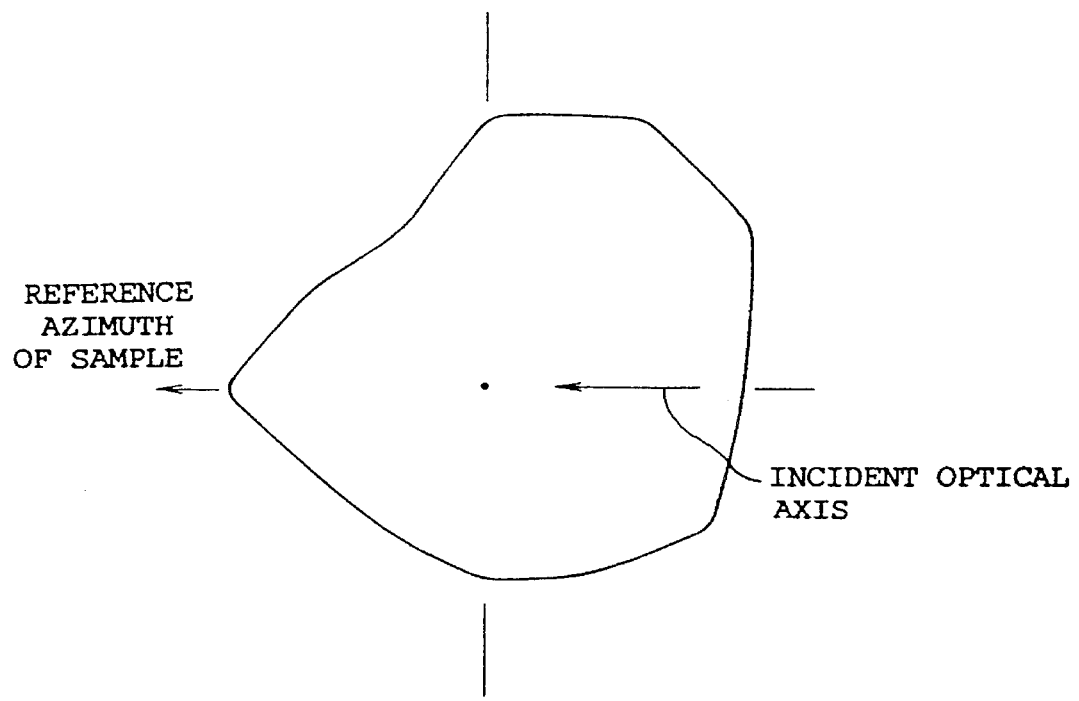
FIG. 34 ms a top plan view of FIG. 33.
Figure 35A:
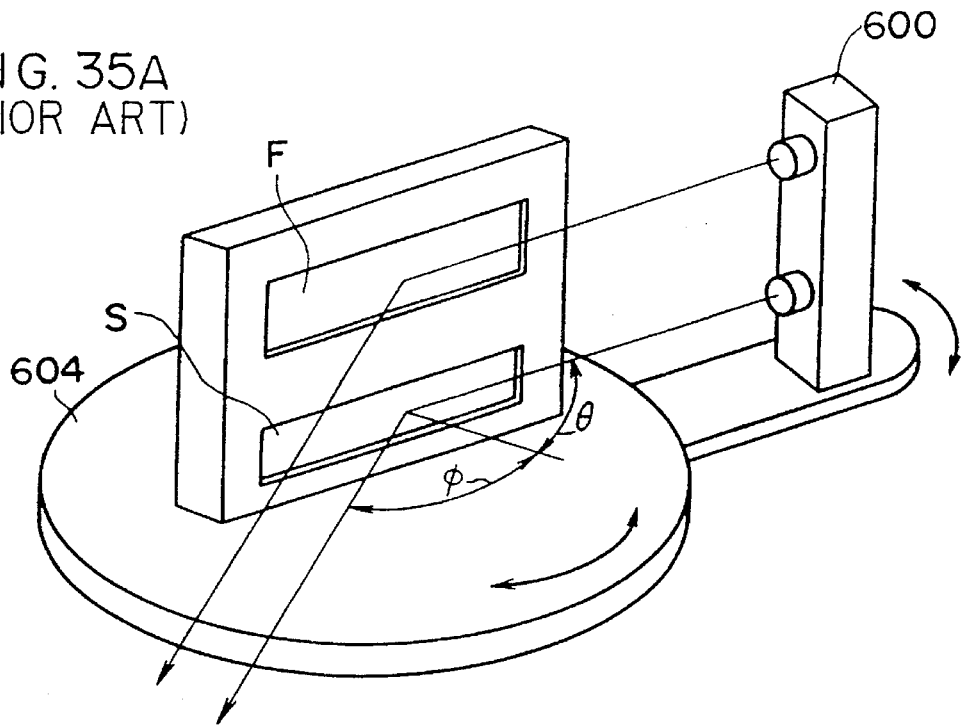
FIG. 35A is a perspective view illustrating a conventional two-dimensional automatic gonio-photometer.
Figure 35B:
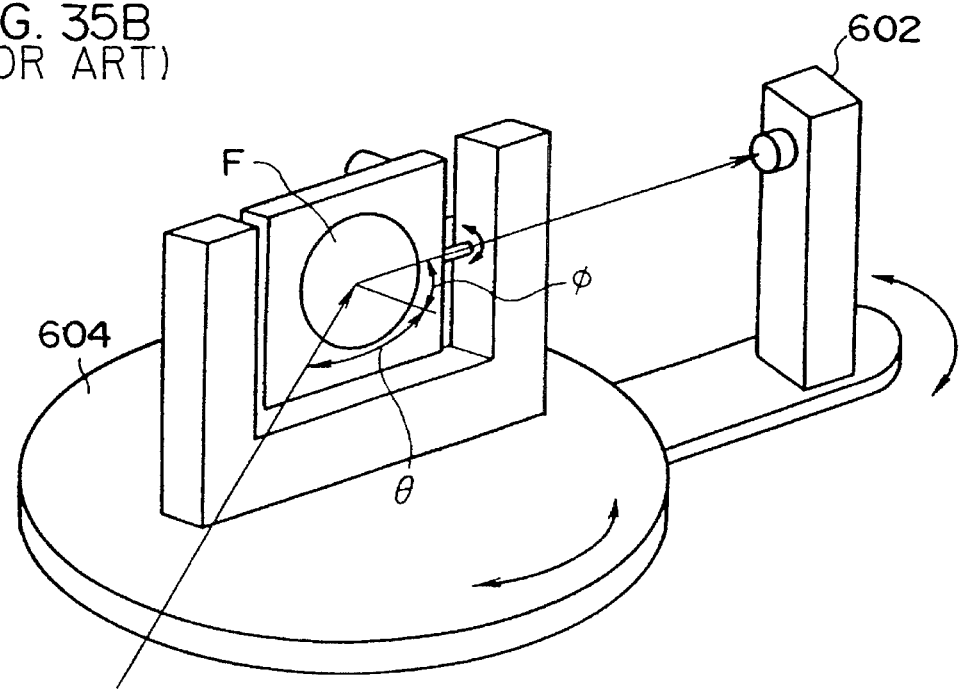
FIG. 35B is a perspective view illustrating a conventional three-dimensional automatic gonio-photometer.

FIGS. 31 and 32 show three-dimensional distributions of the Y value of the tristimulus values when the incident angle θ was 0°, and the azimuth angle Ψ of the sample was 0°. In addition, FIGS. 33 and 34 show three-dimensional distributions of the Y value of the tristimulus values when the incident angle θ was set to 60°, and the azimuth angle Ψ of the sample to 0°. Thus, it can be appreciated that when the incident angle θ is 0°, uniform diffusion is noted even if the azimuth angle Ψ is changed, but if the incident angle θ is changed to 60°, the light is nonuniformly reflected in conjunction with the change in the azimuth angle Ψ.

Figure 27:
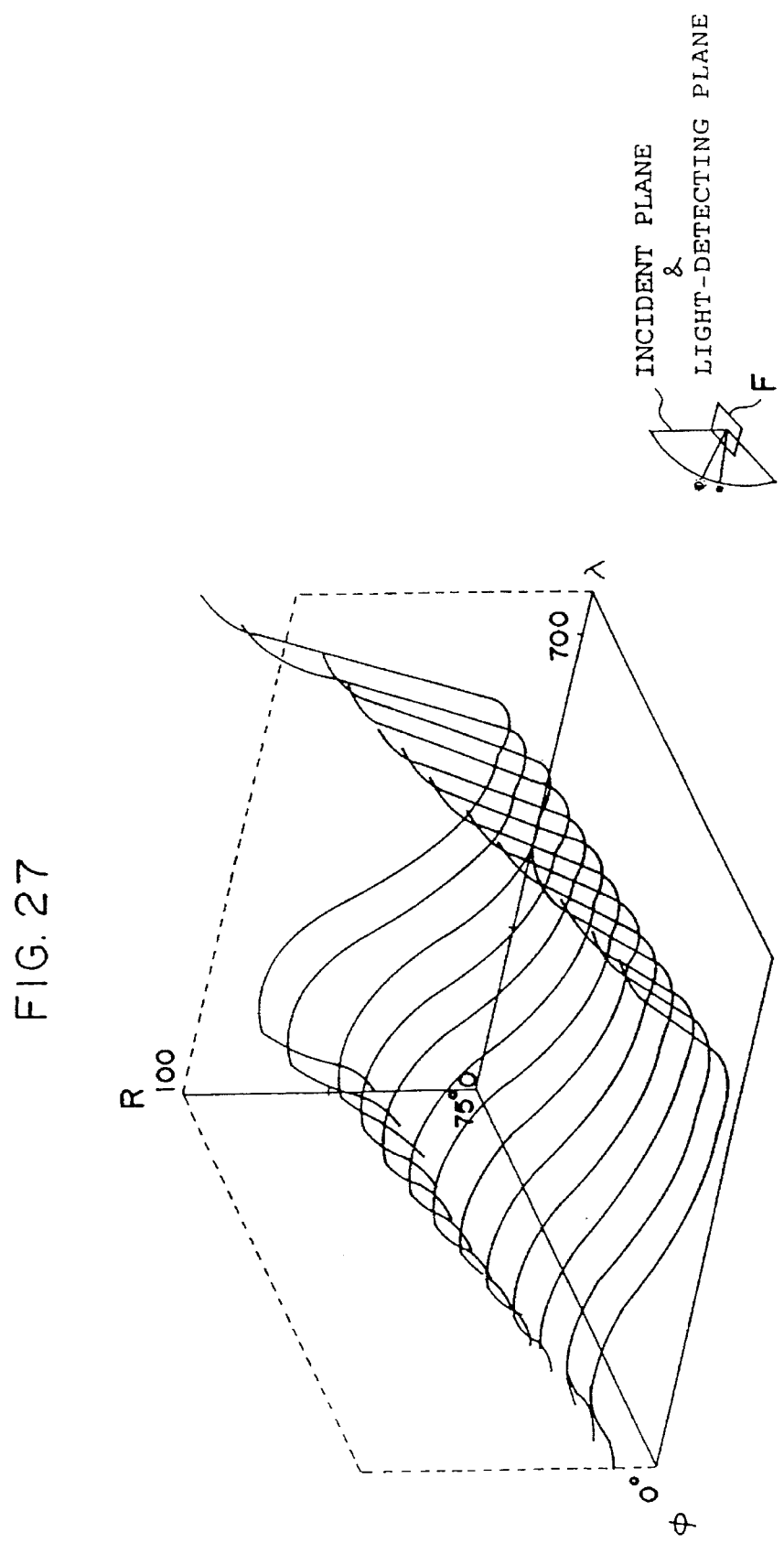
FIG. 27 is a characteristic diagram illustrating spectral reflectance factors when the light-detecting angle is changed.
Figure 28:
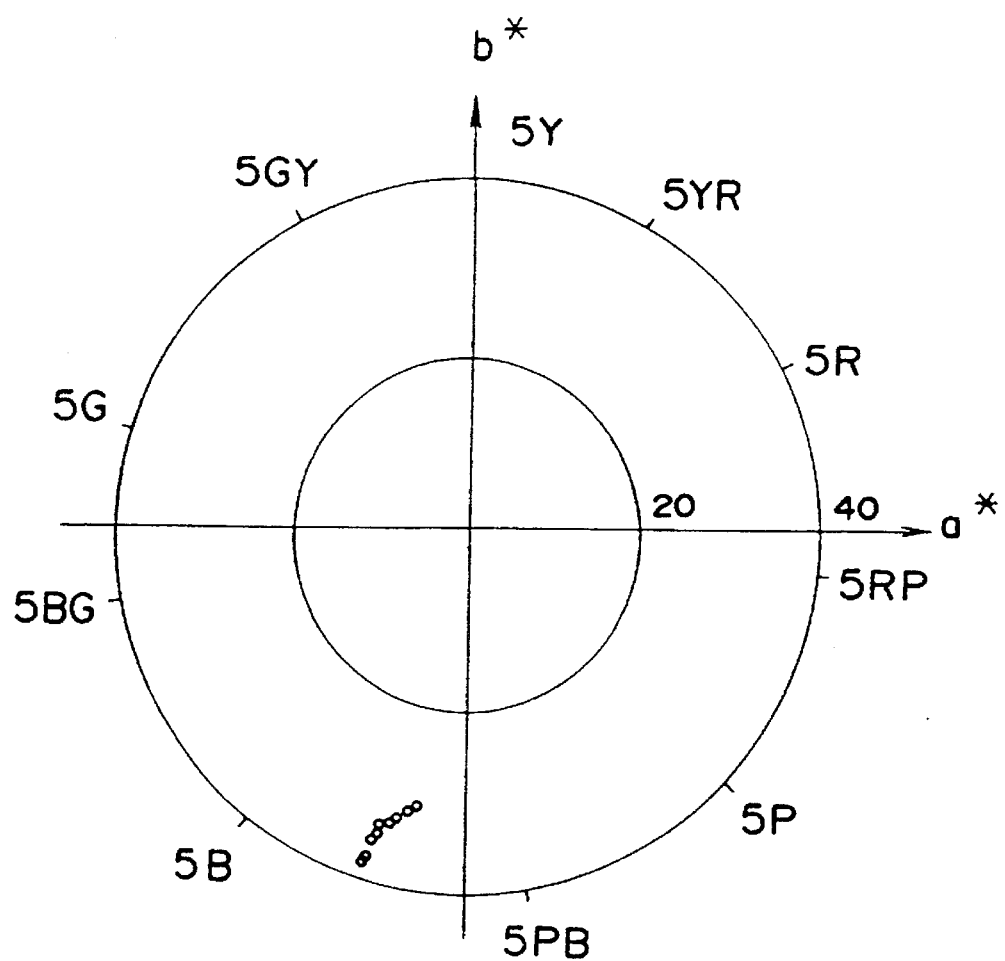
FIG. 28 is a hue circle diagram of FIG. 27.
Figure 29:
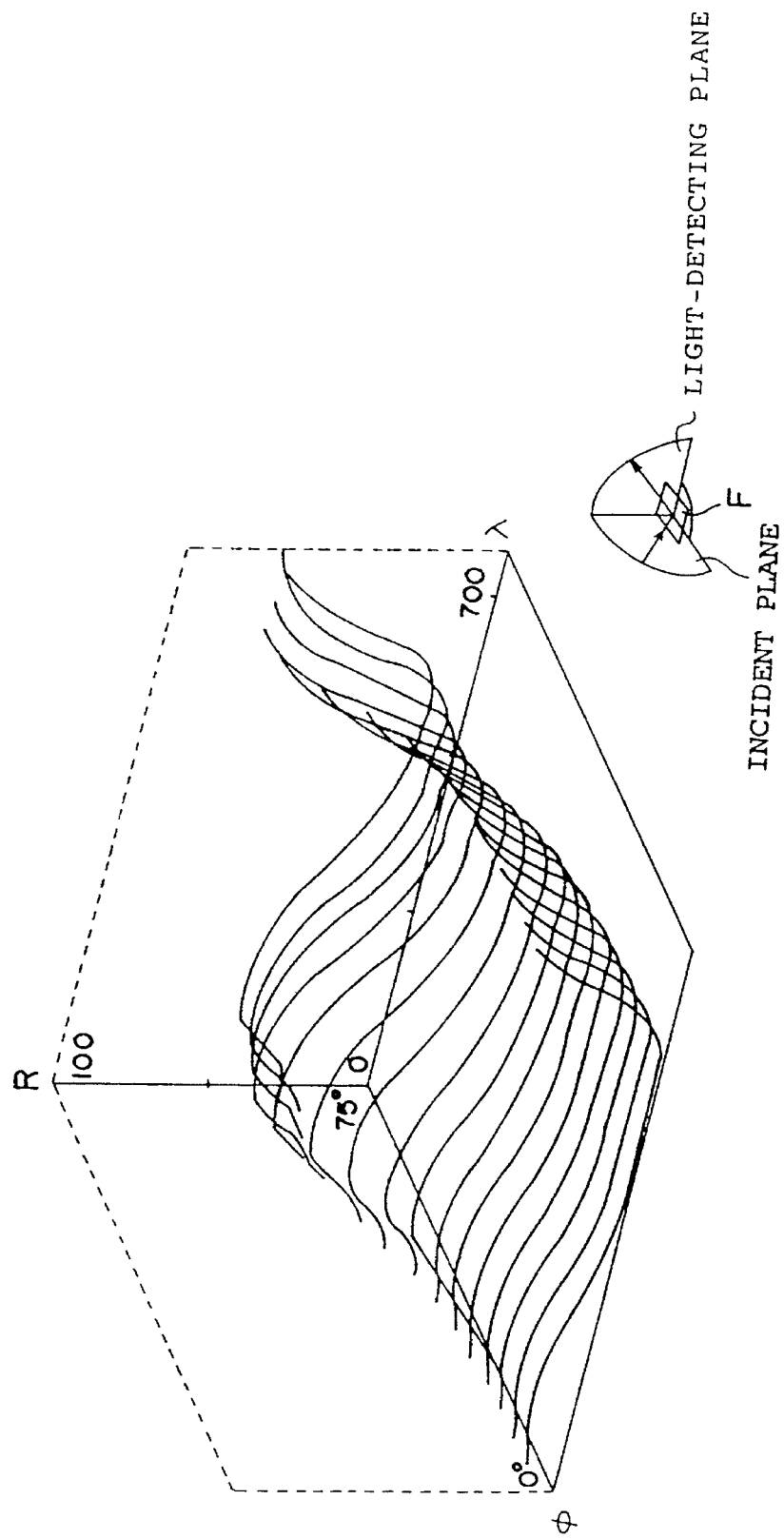
FIG. 29 is a characteristic diagram illustrating spectral reflectance factors when the light-detecting angle is changed.
Figure 30:
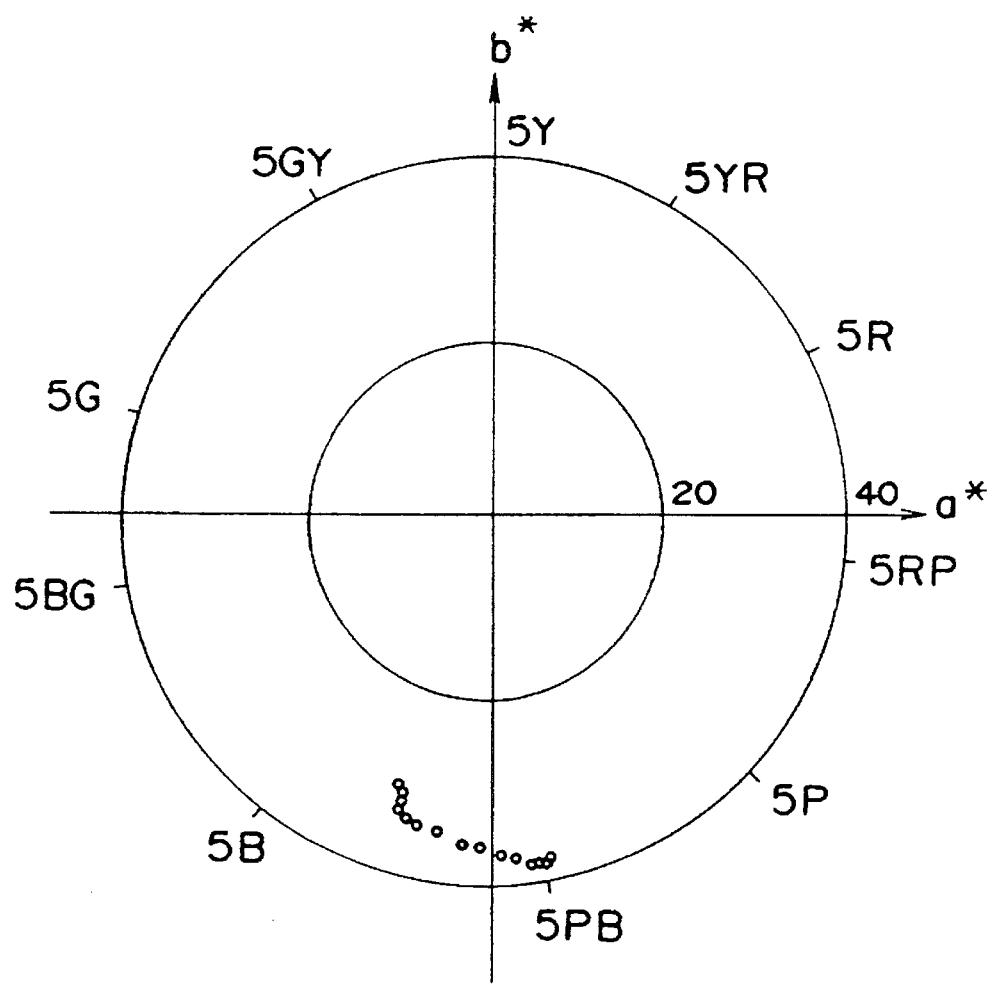
FIG. 30 is a hue circle diagram of FIG. 29.

FIG. 27 shows the manner of change of the spectral reflectance factor R when the incident angle θ, the azimuth angle Ψ, and the azimuth angle $\Psi_o$ of the sample were fixed at 60°, 0°, and 0°, respectively, and the light-detecting angle φ was changed in the range from 0° to 75°. Color differences were displayed under this angular condition. This is shown in FIG. 28. In this color-difference display, the L*a*b* colorimetric system (CIELAB) was used, and points were formed by transforming the values into concentric coordinates to facilitate viewing. FIG. 29 shows the manner of change of the spectral reflectance factor R when the incident angle θ, the azimuth angle Ψ, and the azimuth angle $Ψ_o$ of the sample were fixed at 60°, 90°, and 0°, respectively, and the light-detecting angle φ was changed in the range from 0° to 75°. In the same way as described above, color differences were displayed under this angular condition. This is shown in FIG. 30.

Thus, it can be appreciated that when the azimuth angle Ψ is 0°, the change in the result of color specification is small even if the light-detecting angle φ is changed, but when the azimuth angle Ψ is 90°, the hue changes from B (customarily blue) to PB (customarily bluish violet) in conjunction with the change in the light-detecting angle φ.

As described above, the three-dimensional distribution of the spectral reflectance factors which was unobtainable by the conventional two-dimensional spectrocolorimeter and the three-dimensional gonio-photometer can be automatically obtained by changing the angles (θ', φ', ξ, δ) of the three-dimensional gonio-spectrophotometer 410. Furthermore, even with respect to the regular reflection range where the sheen occurs, since the data interpolated by the measured values of the diffusive reflection range are used, it is possible to obtain spectral reflectance factors accurately.

In this embodiment, to effect the calculation processing of a large amount of measurement data in the above-described manner, grouping is carried out in which the incident angle θ' and the light-detecting angle φ' in the three-dimensional gonio-spectrophotometer 410 are respectively subdivided in units of a predetermined angle (e.g., 10°), a measuring condition table in which the angular conditions are rearranged is prepared, and automatic measurement is effected on the basis of it, thereby effecting high-speed processing. The present inventors confirmed that when automatic measurement was conducted by using the measuring condition table, it was possible to effect measurement in a period (about 48 hours) approximately half the conventional period.

What is claimed is:

1. A rendering apparatus comprising:

radiant-energy calculating means for determining a spectral radiance for each infinitesimal area of an object by using a spectral radiance of a light source irradiating the object, a spectral reflectance in the infinitesimal area of the object at a predetermined angular condition, and a three-dimensional spectral reflectance factor in a wide area of the object;

color-specification-value calculating means for calculating color specification values of a colorimetric system on the basis of the spectral radiance obtained for said each infinitesimal area;

transforming means for transforming the color specification values into image data for displaying an image of the object; and display means for displaying the image of the object on the basis of the image data.

2. The rendering apparatus according to claim 1, wherein the spectral reflectance in the infinitesimal area of the object is the spectral reflectance when an incident angle, a reflection angle, and an azimuth angle are at predetermined values, and the three-dimensional spectral reflectance factor in the wide area of the object is normalized by the three-dimensional spectral reflectance factor in the wide area at a time when the incident angle, the reflection angle, and the azimuth angle are at reference values.

3. The rendering apparatus according to claim 1, wherein the spectral reflectance in the infinitesimal area of the object is normalized by a mean spectral reflectance of the infinitesimal area.

4. The rendering apparatus according to claim 1, wherein said color-specification-value calculating means calculates the color specification values of an XYZ colorimetric system on the basis of the spectral radiance of the respective infinitesimal area obtained, and said transforming means transforms the color specification values of the XYZ colorimetric system into color specification values of an RGB colorimetric system and transforms the transformed color specification values into RGB gradients by using respective γ correction curves of RGB.

5. The rendering apparatus according to claim 1, further comprising:

a multispectral image scanner for measuring said spectral reflectance in the infinitesimal area and including:

measuring means for measuring a quantity of light reflected by the object to which the light is radiated from said light source for each of a plurality of wavelengths or a plurality of wavelength bands;

calibrating means for calibrating for each wavelength or wavelength band a measurement value of a sample for each wavelength or wavelength band measured by said measuring means, by using a measurement value of a reference plate measured by said measuring means as a reference; and estimating means for estimating said spectral reflectance on the basis of the value calibrated for each wavelength or wavelength band.

6. The rendering apparatus according to claim 1, further comprising:

a three-dimensional automatic gonio-spectrophotometer for measuring said three-dimensional spectral reflectance factor in the wide area and including:

disposing means for disposing a sample and a reference plate in such a manner as to allow the sample and said reference plate to form a predetermined angle;

radiating means for radiating the light from a single light source to the sample and said reference plate;

measuring means for measuring respective quantities of the light reflected by the sample and said reference plate by spectrally separating the light into predetermined wavelengths or predetermined wavelength bands;

angle-changing means for changing angles including the incident angle at which the light from the single light source is radiated to the sample, a light-detecting angle at which said measuring means detects the light from the sample, a rotational angle of the sample rotated about a normal line of the sample, and an azimuth angle formed by a light-detecting plane including the normal line of the sample and a light-detecting optical axis leading to said measuring means, with respect to an incident plane including the normal line of the sample and the incident optical axis leading to the sample;

correction-value calculating means in which a plate having a diffusively reflecting surface is disposed at a position where the sample is disposed, for determining a correction value in an angular range other than a regular reflection range on the basis of a reference value measured under a reference angular condition of said plate, and a measurement value of said plate measured under a predetermined angular condition different from the reference angular condition, and for determining a correction value in the regular reflection range by interpolation on the basis of a measurement value in a vicinity of the regular reflection range of said plate under the predetermined angular condition or a correction value in the vicinity of the regular reflection range; and spectral-reflectance-factor calculating means for calculating the spectral reflectance factor of the sample on the basis of the measurement values of the sample and said reference plate measured by said measuring means and the correction value determined by said correction-value calculating means.

7. The rendering apparatus according to claim 5, further comprising:

a three-dimensional automatic gonio-spectrophotometer for measuring said three-dimensional spectral reflectance factor in the wide area and including:

disposing means for disposing a sample and a reference plate in such a manner as to allow the sample and said reference plate to form a predetermined angle;

radiating means for radiating the light from a single light source to the sample and said reference plate;

measuring means for measuring respective quantities of the light reflected by the sample and said reference plate by spectrally separating the light into predetermined wavelengths or predetermined wavelength bands;

angle-changing means for changing angles including the incident angle at which the light from the single light source is radiated to the sample, a light-detecting angle at which said measuring means detects the light from the sample, a rotational angle of the sample rotated about a normal line of the sample, and an azimuth angle formed by a light-detecting plane including the normal line of the sample and a light-detecting optical axis leading to said measuring means, with respect to an incident plane including the normal line of the sample and the incident optical axis leading to the sample;

correction-value calculating means in which a plate having a diffusively reflecting surface is disposed at a position where the sample is disposed, for determining a correction value in an angular range other than a regular reflection range on the basis of a reference value measured under a reference angular condition of said plate, and a measurement value of said plate measured under a predetermined angular condition different from the reference angular condition, and for determining a correction value of the regular reflection range by interpolation on the basis of a measurement value in a vicinity of the regular reflection range of said plate under the predetermined angular condition or a correction value in the vicinity of the regular reflection range; and spectral-reflectance-factor calculating means for calculating the spectral reflectance factor of the sample on the basis of the measurement values of the sample and said reference plate measured by said measuring means and the correction value determined by said correction-value calculating means.

8. The rendering apparatus according to claim 5, wherein said measuring means of said multispectral image scanner includes:

said light source;

a plurality of optical filters for selecting the light in a plurality of wavelength bands which do not overlap from the light reflected from the object to which the light is radiated from said incident light source, by means of reflection or transmission;

light-detecting means for detecting for each of said optical filters a quantity of the light selected by said plurality of optical filters; and correcting means for determining a central wavelength of each of the plurality of wavelength bands corrected on the basis of a spectral distribution obtained by a combination of a spectral distribution of said incident light source, one of a spectral reflectance and a spectral transmittance of each of said optical filters, and a spectral sensitivity distribution of said light-detecting means, thereby effecting measurement for each central wavelength.

9. The rendering apparatus according to claim 5, wherein said calibrating means of said multispectral image scanner determines a correction value on the basis of a reference spectral reflectance predetermined for each of a plurality of color chips of mutually different colors and a measurement value measured for each of said color chips by said measuring means, and calibrates a measurement value of the sample on the basis of the correction value in such a manner that the measurement value of the sample becomes a spectral reflectance of said reference plate.

10. A multispectral image scanner comprising:

optical means including a light source, a plurality of optical filters for selecting light in a plurality of wavelength bands which do not overlap from the light reflected from an object to which the light is radiated from said incident light source, by means of reflection or transmission, and light-detecting means for detecting for each of said optical filters a quantity of the light selected by said plurality of optical filters;

correcting means for determining a central wavelength of each of the plurality of wavelength bands corrected on the basis of a spectral distribution obtained by a combination of a spectral distribution of said incident light source, a spectral transmittance of each of said optical filters, and a spectral sensitivity distribution of said light-detecting means;

calibrating means for calibrating for each predetermined wavelength band a measurement value of a sample with respect to the central wavelength determined by said correcting means, by using a measurement value of a reference plate measured by said optical means as a reference; and estimating means for estimating a spectral reflectance on the basis of the value calibrated for said each central wavelength.

11. The multispectral image scanner according to claim 10, wherein said calibrating means determines a correction value on the basis of a reference spectral reflectance predetermined for each of a plurality of color chips of mutually different colors and a measurement value measured for each of said color chips by said optical means, and calibrates a measurement value of the sample on the basis of the correction value in such a manner that the measurement value of the sample becomes a spectral reflectance of said reference plate.

12. A three-dimensional automatic gonio-spectrophotometer, comprising:

disposing means for disposing a sample and a reference plate in such a manner as to allow the sample and said reference plate to form a predetermined angle;

radiating means for radiating light from a single light source to the sample and said reference plate;

measuring means for measuring respective quantities of the light reflected by the sample and said reference plate for each of predetermined wavelengths or predetermined wavelength bands;

angle-changing means for changing angles including an incident angle at which the light from the single light source is radiated to the sample, a light-detecting angle at which said measuring means detects the light from the sample, a rotational angle of the sample rotated about a normal line of the sample, and an azimuth angle formed by a light-detecting plane including the normal line of the sample and a light-detecting optical axis leading to said measuring means, with respect to an incident plane including the normal line of the sample and the incident optical axis leading to the sample;

correction-value calculating means in which a plate having a diffusively reflecting surface is disposed at a position where the sample is disposed, for determining a correction value in an angular range other than a regular reflection range on the basis of a reference value measured under a reference angular condition of said plate, and a measurement value of said plate measured under a predetermined angular condition different from the reference angular condition, and for determining a correction value in the regular reflection range by interpolation on the basis of a measurement value in a vicinity of the regular reflection range of said plate under the predetermined angular condition or a correction value in the vicinity of the regular reflection range; and spectral-reflectance-factor calculating means for calculating a spectral reflectance factor of the sample on the basis of measurement values of the sample and said reference plate measured by said measuring means and the correction value determined by said correction-value calculating means.

13. A rendering apparatus comprising:

radiant-energy calculating means for determining a spectral radiance for each infinitesimal area of an object using a product of a spectral radiance of a light source, a spectral reflectance in the infinitesimal area of the object, and one of a reflectance ratio and a radiance ratio respectively standardized by a value corresponding to a three-dimensional spectral reflectance factor in a wide area of the object;

color-specification-value calculating means for calculating color specification values of a colorimetric system on the basis of the spectral radiance obtained for said each infinitesimal area;

transforming means for transforming the color specification values into image data for displaying an image of the object; and display means for displaying the image of the object on the basis of the image data.

14. A rendering apparatus comprising:

radiant-energy calculating means for determining a spectral radiance for each infinitesimal area of an object using a product of a spectral radiance of a light source, one of a reflectance ratio and a radiance ratio of the infinitesimal area, said ratios are respectively standardized by a value corresponding to an average spectral reflectance of the infinitesimal area of the object, and a three-dimensional spectral reflectance factor in a wide area of the object;

color-specification-value calculating means for calculating color specification values of a colorimetric system on the basis of a spectral radiance obtained for said each infinitesimal area;

transforming means for transforming the color specification values into image data for displaying an image of the object; and display means for displaying the image of the object on the basis of the image data.

* * * * *

UNITED STATES PATENT AND TRADEMARK OFFICE
CERTIFICATE OF CORRECTION

PATENT NO. : 5,502,799
DATED : March 26, 1996
INVENTOR(S) : Hiroyoshi TSUJI, et al.

It is certified that error appears in the above-indentified patent and that said Letters Patent is hereby corrected as shown below:

On the title page, Item [73], the Assignees, should read:

--Kabushiki Kaisha Toyota Chuo Kenkyusho, Aichi;
Toyota Jidosha Kabushiki Kaisha, Toyota,
both of Japan--

Signed and Sealed this

Thirteenth Day of August, 1996

Attest:

BRUCE LEHMAN

*Attesting Officer*   *Commissioner of Patents and Trademarks*